United States Patent [19]

Miller et al.

[11] Patent Number: 5,201,933
[45] Date of Patent: Apr. 13, 1993

[54] SAFENING HERBICIDAL BENZOIC ACID DERIVATIVES

[75] Inventors: Knudt J. Miller, Milton, Wis.; Brett H. Bussler, St. Louis Park, Minn.

[73] Assignee: Monsanto Company, St. Louis, Mo.

[21] Appl. No.: 596,453

[22] Filed: Oct. 12, 1990

Related U.S. Application Data

[63] Continuation-in-part of Ser. No. 486,470, Feb. 28, 1990, abandoned, which is a continuation-in-part of Ser. No. 462,197, Jan. 9, 1990, abandoned, which is a continuation-in-part of Ser. No. 369,461, Jun. 26, 1989, abandoned, which is a continuation-in-part of Ser. No. 226,928, Aug. 1, 1988, abandoned.

[51] Int. Cl.$^5$ ............... B21D 17/04; B21D 15/04; B21D 3/02; B21D 19/00
[52] U.S. Cl. ................ 504/104; 71/DIG. 1; 504/105; 504/107; 504/108; 504/109; 504/110; 504/111; 504/112; 504/106
[58] Field of Search .......... 71/88, 90, 92, 94, 95, 71/105, 106, 107, 111, 112, 113, 114, 118, DIG. 1

[56] References Cited

U.S. PATENT DOCUMENTS

| | | | |
|---|---|---|---|
| 3,473,913 | 10/1969 | Zick | 71/115 |
| 3,702,759 | 11/1972 | Hoffman | 71/77 |
| 4,033,756 | 7/1977 | Hoffman | 71/118 |
| 4,070,389 | 1/1978 | Martin | 71/77 |
| 4,152,137 | 5/1979 | Martin | 71/108 |
| 4,237,302 | 12/1980 | Hoffman et al. | 71/90 |
| 4,269,775 | 5/1981 | Szczepanski et al. | 71/76 |
| 4,279,636 | 7/1981 | Hoffman et al. | 71/90 |
| 4,299,616 | 11/1981 | Hyzak | 71/100 |
| 4,330,323 | 5/1982 | Gothy et al. | 71/118 |
| 4,331,466 | 5/1982 | Rodebush | 71/88 |
| 4,332,614 | 6/1982 | Alt | 71/94 |
| 4,345,938 | 8/1982 | Alt | 71/118 |
| 4,381,936 | 5/1983 | Hyzak | 71/100 |
| 4,394,152 | 7/1983 | Sturm et al. | 71/77 |
| 4,398,941 | 8/1983 | Howe et al. | 71/118 |
| 4,433,999 | 2/1984 | Hyzak | 71/100 |
| 4,451,285 | 5/1984 | Alt | 71/90 |
| 4,461,642 | 7/1984 | Howe et al. | 71/105 |
| 4,468,242 | 8/1984 | Szczepanski | 71/88 |
| 4,483,707 | 11/1984 | Breitenstein et al. | 71/94 |
| 4,493,726 | 1/1985 | Burdeska et al. | 71/89 |
| 4,530,716 | 7/1985 | Martin et al. | 71/88 |
| 4,532,732 | 8/1985 | Szczepanski | 71/88 |
| 4,534,783 | 8/1985 | Beestman | 71/27 |
| 4,566,901 | 1/1986 | Martin et al. | 71/108 |
| 4,567,299 | 1/1986 | Alt et al. | 71/95 |
| 4,579,691 | 4/1986 | Maier et al. | 558/159 |
| 4,600,433 | 7/1986 | Alt | 71/118 |
| 4,601,745 | 7/1986 | Moser | 71/88 |
| 4,605,764 | 8/1986 | Matolosy et al. | 564/209 |
| 4,606,759 | 8/1986 | Alt | 71/118 |
| 4,618,361 | 10/1986 | Moser | 71/88 |
| 4,622,061 | 11/1986 | Alt | 71/118 |
| 4,623,383 | 11/1986 | Toth et al. | 71/88 |
| 4,623,727 | 11/1986 | Hubele | 71/92 |
| 4,648,895 | 3/1987 | Martin et al. | 71/88 |
| 4,648,896 | 3/1987 | Brunner | 71/90 |
| 4,674,229 | 6/1987 | Burdeska et al. | 71/92 |
| 4,676,823 | 6/1987 | Maier et al. | 71/86 |
| 4,698,091 | 10/1987 | Brunner et al. | 71/88 |
| 4,731,109 | 3/1988 | Chupp | 71/118 |
| 4,731,451 | 3/1988 | Chupp | 71/88 |
| 4,740,236 | 4/1988 | Töpfl | 71/103 |
| 4,749,406 | 6/1988 | Martin | 71/94 |
| 4,759,789 | 7/1988 | Martin | 71/90 |
| 4,761,176 | 8/1988 | Alt | 71/88 |
| 4,851,033 | 7/1989 | Hubele | 71/94 |

OTHER PUBLICATIONS

"Summary of Conservation Tillage Corn Herbicide Practices in Northeast Iowa" Proceedings of NCWCC, vol. 33, pp. 87-91, 1978.

(List continued on next page.)

Primary Examiner—Alan L. Rotman
Assistant Examiner—Raymond Covington
Attorney, Agent, or Firm—William I. Andress

[57] ABSTRACT

The disclosure herein relates to the use of certain amides of dichloroacetic acid and other compounds as safener/antidotal compounds to reduce the phytotoxicity to crop plants, especially corn, of benzoic acid-type herbicides alone or in admixture with other co-herbicidal compounds, e.g., α-haloacetamides.

83 Claims, No Drawings

OTHER PUBLICATIONS

"Herbicides for Velvetleaf Control in Corn" Proceedings of Northeast Weed Science Society, vol. 32, pp. 2-3, 1978.

"Field Corn Inbreds and Popcorn Tolerance to Several Corn Herbicides" Proceedings of North Central Weed Control Conference (NCWCC), vol. 28, pp. 84-85, 1973.

"Corn Herbicide Evaluations Across Iowa, 1977" Proceedings of NCWCC, vol. 32, pp. 71-78, 1977.

"Triazine Resistant Redroot Pigweed Control" Proceedings of Northeast Weed Science Society, vol. 33, pp. 8-9, 1979.

"A Three Year Summary of Velvetleaf Control in Corn" Proceedings of Northeast Weed Science Society, vol. 33, pp. 2-3, 1979.

"Effect of a Combined Application of Experimental Granular Dicamba with Granular Alachlor and Butylate and Weed Control in Corn" NCWCC Report, vol. 36, pp. 138-140, 1981.

"Herbicide Peformance on Corn at Waseca MN in 1982" NCWCC Research Report, vol. 39, 1982.

"Sequential use of Dicamba in Corn Following Acetanilide Herbicides" (No Date).

SAFENING HERBICIDAL BENZOIC ACID DERIVATIVES

RELATED APPLICATIONS

This application is a Continuation-in-part of copending U.S. Ser. No. 07/486,470 filed Feb. 28, 1990, abandoned, which is a Continuation-in-part of copending U.S. Ser. No. 07/462,197 filed Jan. 9, 1990 now abandoned, which is a Continuation-in-part of U.S. Ser. No. 07/369,461 filed Jun. 26, 1989, now abandoned which is a Continuation-in-part of U.S. Ser. No. 07/226,928 Aug. 1, 1985 now abandoned; and of copending U.S. Ser. 07/212,621, now U.S. Pat. No. 4,904,560 which is a Continuation-in-part of U.S. Ser. No. 07/084,785, now abandoned.

FIELD OF THE INVENTION

The field of the invention contemplated herein pertains to the safening of herbicidal compounds with antidotal or safener compounds. Particular herbicides involved are those of the benzoic acid derivatives with or without co-herbicidal compounds, e.g., α-haloacetamides and α-haloacetanilides.

BACKGROUND OF THE INVENTION

Many herbicides injure crop plants at herbicide application rates necessary to control weed growth. Accordingly, many herbicides cannot be used for controlling weeds in the presence of certain crops. Uncontrolled weed growth, however, results in lower crop yield and reduced crop quality inasmuch as weeds compete with crops for light, water and soil nutrients. Reduction of herbicidal injury to crops without an unacceptable corresponding reduction of herbicidal action on the weeds can be accomplished by use of crop protectants known as herbicide "antagonists", "antidotes" or "safeners".

Weed control for crops, especially corn crops, is one of the oldest and most highly developed areas in weed science. For a herbicide product to be accepted commercially for corn crops, such herbicide product must provide a relatively high level of control of both grassy and broadleaf weeds in corn, in addition to meeting several other criteria. For example, the herbicide should possess relatively high unit activity so that lower rates of herbicide application are feasible. Lower application rates are desirable in order to minimize exposure of the environment to the herbicide. At the same time, such herbicide must be selective in herbicidal effect so as not to injure the crops. Herbicidal selectivity can be enhanced by use of an appropriate antidote in combination with the herbicide. But identification of an antidote which safens a herbicide in crops is a highly complicated task. Whether a compound or class of compounds provides efficacious antidote or safening activity is not a theoretical determination but must be done empirically. Safening activity is determined empirically by observing the complex interaction of several biological and chemical factors, namely: the type of herbicide compound; the type of weed to be controlled; the type of crop to be protected from weed competition and herbicidal injury; and the antidote compound itself. Moreover, the herbicide and antidote must each possess chemical and physical properties enabling preparation of a stable formulation which is environmentally safe and easy to apply to the field.

Among the various classes of compounds found to be suitable for various herbicidal purposes are the α-haloacetanilides and benzoic acid derivatives. The former herbicides, e.g., alachlor, acetochlor, metollachlor, etc., are excellent preemergence or early post emergence herbicides for controlling annual grasses and many broadleaved weeds in corn, peanuts, soybeans and other crops, while some of the latter herbicides, exemplified by dicamba and its salts, may be used as a foliar—or soil-applied herbicide suitable for the control of many annual and perennial broadleaved species in asparagus, cereals, grain, corn, sorghum, sugarcane and other crops and woody brush and vine control in pasture, rangeland and cropland. Other members of the latter class, e.g., amiben (chloramben) can be used in preplant or preemergence applications.

It is a common agronomic practice to use various antidotal compounds to reduce the phytotoxicity of some herbicides to various crops. For example, fluorazole (active ingredient in SCREEN ® safener) is used as a seed dressing to protect sorghum seed from alachlor (active ingredient in LASSO ® herbicide). Similarly, cyometrinil (active ingredient in CONCEP ®. safener) is a corn seed safener for use with metolachlor and oxabetrinil (active ingredient in CONCEP II safener) is used to safen sorghum seed from injury by metolachlor. The compound N,N-diallyl dichloroacetamide (common name R-25788) is used to safen corn from injury by the thiocarbamate 5-ethyl-N,N-dipropylthiocarbamate (active ingredient in ERADICANE ® herbicide) and acetochlor (active ingredient in HARNESS ® herbicide).

It is an object of this invention to provide compositions of benzoic acid and substituted-benzoic acid herbicides in combination with antidotes therefor, optionally containing a co-herbicide, which compositions are useful to reduce injury to crops, especially corn, due to phytotoxicity of said herbicides.

SUMMARY OF THE INVENTION

The present invention relates to herbicidal compositions comprising benzoic acid derivatives and antidotal compounds therefor to reduce injury to various crops, particularly corn, from the phytotoxic effects of said herbicide when used alone or in combination with other compounds, particularly α-haloacetamides and α-haloacetanilides, as co-herbicides. Except where noted herein the term "α-haloacetamides" generically includes α-haloacetanilides as a subgroup (which require a phenyl or substituted phenyl attached to the acetamide nitrogen atom) and acetamides which have substituents other than a (un)substituted phenyl.

In more particular, in a major aspect, this invention relates to a composition comprising:

(a) a herbicidal compound having the formula

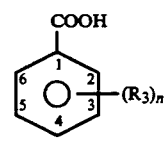

I and agriculturally-acceptable salts thereof wherein
R$_3$ is halogen, C$_{1-5}$ alkoxy or C$_{1-4}$ alkyl-substituted amino and
n is 0–5
alone or in admixture with other known herbicidal compounds as co-herbicides, preferably an α-haloacetamide of the formula

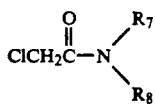

wherein $R_7$ and $R_8$ are independently hydrogen; $C_{1-8}$ alkyl, alkoxy, alkoxyalkyl, acylaminomethyl, acyl-lower alkyl-substituted aminomethyl; cycloalkyl, cycloalkylmethyl, mono- or polyunsaturated alkenyl, alkynyl, cycloalkenyl, cycloalkenylmethyl having up to 8 carbon atoms; phenyl; or $C_{4-10}$ heterocyclyl or heterocyclylmethyl containing from 1 to 4 ring hetero atoms selected independently from N, S or O; and wherein said $R_7$ and $R_8$ members may be substituted with alkyl, alkenyl, alkynyl, alkenyloxy, alkynyloxy, alkoxy, alkoxyalkyl, alkoxycarbomethyl or ethyl having up to 8 carbon atoms; nitro; halogen; cyano; amino or $C_{1-4}$ alkyl-substituted amino; and wherein $R_7$ and $R_8$ may be combined together with the N atom to which attached to form one of said heterocyclyl or substituted-heterocyclyl members; provided that:

(a) $R_7$ and $R_8$ are not simultaneously hydrogen;

(b) when $R_7$ is substituted-phenyl, the positions on the phenyl ring ortho to the N atom are other than alkoxy or trifluoromethyl and when the ortho positions contain an alkyl radical, $R_8$ is other than alkyl or acylaminomethyl;

(c) when $R_7$ is cycloalkenyl or substituted cycloalkenyl or phenyl, $R_8$ is other than an (un)substituted (2-oxo-3(2H)benzothiazolyl) methyl radical;

(d) when $R_7$ is an alkenyl or substituted alkenyl radical, $R_8$ is other than a substituted-alkylene radical and (b) an antidotally-effective amount of (i) a compound of the formula

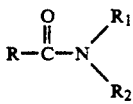

wherein R can be selected from the group consisting of haloalkyl; haloalkenyl; alkyl; alkenyl; cycloalkyl; cycloalkylalkyl; halogen; hydrogen; carboalkoxy; N-alkenylcarbamylalkyl; N-alkenylcarbamyl; N-alkyl-N-alkynylcarbamyl; N-alkyl-N-alkynylcarbamylalkyl; N-alkenylcarbamylalkoxyalkyl; N-alkyl-N-alkynylcarbamylalkoxyalkyl; alkynoxy; haloalkoxy; thiocyanatoalkyl; alkenylaminoalkyl; alkylcarboalkyl; cyanoalkyl; cyanatoalkyl; alkenylaminosulfonalkyl; alkylthioalkyl; haloalkylcarbonyloxyalkyl, alkoxycarboalkyl; haloalkenylcarbonyloxyalkyl; hydroxyhaloalkyloxyalkyl; hydroxyalkylcarboalkyoxyalkyl; hydroxyalkyl; alkoxysulfonoalkyl; furyl; thienyl; alkyldithiolenyl; thienalkyl; phenyl and substituted phenyl wherein said substituents can be selected from halogen, alkyl, haloalkyl, alkoxy, carbamyl, nitro, carboxylic acids and their salts, haloalkylcarbamyl; phenylalkyl; phenylhaloalkyl; phenylalkenyl; substituted phenylalkenyl wherein said substituents can be selected from halogen, alkyl, alkoxy, halophenoxy, phenylalkoxy; phenylalkylcarboxyalkyl; phenylcycloalkyl; halophenylalkenoxy; halothiophenylalkyl; halophenoxyalkyl; bicycloalkyl; alkenylcarbamylpyridinyl; alkynylcarbamylpyridinyl; dialkenylcarbamylbicycloalkenyl; alkynylcarbamylbicycloalkenyl;

$R_1$ and $R_2$ can be the same or different and can be selected from the group consisting of alkenyl; haloalkenyl; hydrogen; alkyl; haloalkyl; alkynyl; cyanoalkyl; hydroxyalkyl; hydroxyhaloalkyl; haloalkylcarboxyalkyl; alkylcarboxyalkyl; alkoxycarboxyalkyl; thioalkylcarboxyalkyl; alkoxycarboalkyl; alkylcarbamyloxyalkyl; amino; formyl; haloalkyl-N-alkylamido; haloalkylamido; haloalkylamidoalkyl; haloalkyl-N-alkylamidoalkyl; haloalkylamidoalkenyl; alkylimino; cycloalkyl; alkylcycloalkyl; alkoxyalkyl; alkylsulfonyloxyalkyl; mercaptoalkyl; alkylaminoalkyl; alkoxycarboalkenyl; haloalkylcarbonyl; alkylcarbonyl; alkenylcarbamyloxyalkyl; cycloalkylcarbamyloxyalkyl; alkoxycarbonyl; haloalkoxycarbonyl; halophenylcarbamyloxyalkyl; cycloalkenyl; phenyl; substituted phenyl wherein said substituents can be selected from alkyl, halogen, haloalkyl, lkoxy, haloalkylamido, phthalamido, hydroxy, alkylcarbamyloxy, alkenylcarbamyloxy, alkylamido, haloalkylamido or alkylcarboalkenyl; phenylsulfonyl; substituted phenylalkyl wherein said substituents can be selected from halogen or alkyl; dioxyalkylene, halophenoxyalkylamidoalkyl; alkylthiodiazolyl; piperidyl; piperidylalkyl; dioxolanylalkyl, thiazolyl; alkylthiazolyl; benzothiazolyl; halobenzothiazolyl; furyl; alkyl-substituted furyl; furylalkyl; pyridyl; alkylpyridyl; alkyloxazolyl; tetrahydrofurylalkyl; 3-cyano, thienyl; alkyl-substituted thienyl; 4,5-polyalkylene-thienyl; α-haloalkylacetamidophenylalkyl; α-haloalkylacetamidonitrophenylalkyl; α-haloalkylacetamidohalophenylalkyl; cyanoalkenyl;

$R_1$ and $R_2$ when taken together can form a structure consisting of piperidinyl; alkylpiperidinyl; pyridyl; di- or tetrahydropyridinyl; alkyltetrahydropyridyl; morpholyl; alkylmorpholyl; azabicyclononyl; diazacycloalkanyl; benzoalkylpyrrolidinyl; oxazolidinyl; perhydrooxazolidinyl; alkyloxazolidyl; furyloxazolidinyl; thienyloxazolidinyl; pyridyloxazolidinyl; pyrimidinyloxazolidinyl; benzooxazolidinyl; $C_{3-7}$ spirooycloalkyloxazolidinyl; alkylaminoalkenyl; alkylideneimino; pyrrolidinyl; piperidonyl; perhydroazepinyl; perhydroazocinyl; pyrazolyl; dihydropyrazolyl; piperazinyl; perhydro- 1,4-diazepinyl; quinolinyl; isoquinolinyl; dihydro-, tetrahydro- and perhydroquinolyl- or -isoquinolyl; indolyl and di- and perhydroindolyl and said combined $R_1$ and $R_2$ members substituted with those independent $R_1$ and $R_2$ radicals enumerated above; or (ii) one of the following compounds α-[(Cyanomethoxy)imino]benzeneacetonitrile, α-[(1,3-Dioxolan-2-yl-methoxy)-imino]-benzeneacetonitrile, O-[3-Dioxolan-2-ylmethyl]-2,2,2-trifluoromethyl-4'-chloroacetophenone oxime, Benzenemethamine, N-[4-(dichloromethylene]- 1,3-diotholan-2-ylidene]-α-methyl, hydrochloride, Diphenylmethoxy acetic acid, methyl ester, 1,8-Naphthalic anhydride, 4,6-Dichloro-2-phenyl-pyrimidine, 2-Chloro-N-[1-(2, 4, 6-trimethylphenyl)-ethenyl]acetamide, Ethylene glycol acetal of 1, 1-dichloroacetone.

Preferred herbicidal compounds according to Formula I are those wherein n is 3 or 4 and the $R_3$ members are halogen, $C_{1-4}$ alkoxy and/or $C_{1-4}$ alkyl-substituted amino. In particular, the preferred $R_3$ members are halogen members, preferably chlorine atoms, and/or a $C_{1-4}$ alkoxy (preferably methoxy) radical in the 2 position. The preferred species are 3,6-dichloro-2-methoxybenzoic acid (common name "dicamba"), 3,5,6-trichloro-2-methoxybenzoic acid (common name "tricamba"), 2,3,6-trichlorobenzoic acid, 2,3,5,6-tetrachlorobenzoic acid and an alkali metal (especially sodium or potassium) salt, or dimethyl- or diethylamine, morpholinyl or ammonium salts of those acids.

Preferred herbicidal compounds according to Formula IV are those wherein the $R_7$ member is an alkoxyalkyl radical of the structure —(A)—O—B, wherein A and B are linear or branched-chain alkyl residues having a combined total of up to 8 carbon atoms; or a substituted or unsubstituted $C_{4-10}$ heterocyclyl or heterocyclylmethyl radical containing from 1 to 4 ring hetero atoms selected independently from N, S or O atoms and the $R_8$ member is also one of said heterocyclyl or heterocyclylmethyl radicals or an optionally-substituted phenyl radical. Preferably the phenyl radical is substituted with alkyl groups, especially in the ortho positions. Similarly, some preferred heterocyclic members are substituted with alkyl or alkoxy radicals.

Among the more important heterocyclic $R_1$ and/or $R_8$ members of Formula IV are mentioned independently, the furanyl, thienyl, pyrazolyl, pyrrolyl, isoxazolyl, isothiazolyl, triazolyl, imidazolyl, and pyrimidinyl radicals and their analogs having a methylene (—CH$_2$—) moiety connecting the heterocyclic radical to the acetamide nitrogen atom, e.g., pyrazol- 1-ylmethyl. When the heterocyclic radical is attached directly to the amide nitrogen (with no intervening methylene moiety), the attachment may be through a ring carbon atom or a ring hetero atom as appropriate.

Other important $R_7$ and/or $R_8$ members include the following: propynyl, alkoxycarbomethyl or -ethyl, alkoxyiminoalkyl, benzyl, hydroxyalkyl, haloalkoxy and -alkoxyalkyl, cyanoalkoxy and -alkoxyalkyl, methyl, ethyl, propyl, butyl and their isomers, and the like.

Among preferred species of Formula IV are mentioned N-(2,4-dimethylthien-3-yl)-N-(1-methoxyprop2-yl)- 2-chloroacetamide, N-(1H-pyrazol-1-ylmethyl)-N-(2,4-dimethylthien-3-yl)-2-chloroacetamide and N-( 1-pyrazol-1-ylmethyl)-N-(4,6-dimethoxypyrimidin-5-yl)-2-chloroacetamide.

Another important subgenus of preferred α-haloacetamide compounds useful as co-herbicides are the α-chloroacetanilides according to Formula V

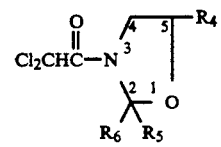

wherein
$R_9$ is hydrogen, $C_{1-6}$ alkyl, haloalkyl, alkoxy or alkoxyalkyl, alkenyl, haloalkenyl, alkynyl or haloalkynyl having up to 6 carbon atoms, $C_{5-10}$ heterocyclyl or heterocyclylmethyl having O,S and/or N atoms and which may be substituted with halogen, $C_{1-4}$ alkyl, carbonylalkyl or carbonylalkoxyalkyl, nitro, amino or cyano groups;
$R_{10}$ is hydrogen, halogen, nitro, amino, $C_{1-6}$ alkyl, alkoxy or alkoxyalkyl, and
m is 0-5; provided that when m is O, $R_9$ is not an (un)substituted (2-oxo-3(2H)benzothiazolyl)methyl radical; when m is other than O, $R_{10}$ is not an alkoxy or trifluoromethyl radical in an ortho position and when $R_{10}$ is an alkyl radical in the ortho positions, $R_9$ is not an alkyl or acylaminomethyl radical.

The most preferred species of Formula V are 2-chloro-2'-ethyl-6'-methyl-N-(ethoxymethyl)acetanilide (common name "acetochlor"), 2-chloro-2',6'-diethyl-N-(methoxymethyl)acetanilide (common name "alachlor"), 2-chloro-2',6'-diethyl-N-(butoxymethyl)acetanilide (common name "butachlor"), 2-chloro-2'-ethyl-6'-methyl-N-(1-methyl-2-methoxyethyl)acetanilide (common name "metolachlor"), 2-chloro-2',6'-diethyl-N-(2-n-propoxyethyl)acetanilide (common name "pretilachlor") and 2-chloro-2',6'-dimethyl-N-(pyrazolylmethyl)acetanilide (common name "metazachlor").

A larger group of preferred co-herbicides includes the particular preferred species of Formulae IV and V identified above.

One group of preferred antidotal compounds includes those according to Formula II wherein R is $C_{1-3}$ haloalkyl, $R_1$ and $R_2$ are independently $C_{2-4}$ alkenyl or haloalkenyl or 2,3-dioxolan-2-yl-methyl and $R_1$ and $R_2$ when combined form a $C_{4-10}$ saturated or unsaturated heterocyclic ring containing O, S and/or N atoms and which may be substituted with $C_{1-5}$ alkyl, haloalkyl, alkoxy, or alkoxyalkyl or haloacyl groups. The preferred haloalkyl R member in formula II is dichloromethyl. Preferred species in this group of antidotal compounds are N,N-diallyl-dichloroacetamide and N-(2-propenyl)-N-(1,3-dioxolanylmethyl)dichloroacetamide.

Still more preferred antidotal compounds according to Formula II is a group of substituted 1,3-oxazolidinyl dichloroacetamide having the formula

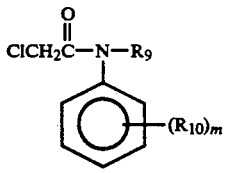

wherein
$R_4$ is hydrogen, $C_{1-4}$ alkyl, alkylol, haloalkyl or alkoxy, $C_{2-6}$ alkoxyalkyl, a bicyclic hydrocarbon radical having up to 10 carbon atoms, phenyl or a saturated or unsaturated heterocyclic radical having $C_{4-10}$ ring atoms and containing O, S and/or N atoms, or said phenyl and heterocyclic radical substituted with one or more $C_{1-4}$ alkyl, haloalkyl, alkoxy, alkoxyalkyl, halogen or nitro radicals, and
$R_5$ and $R_6$ are independently hydrogen, $C_{1-4}$ alkyl or haloalkyl, phenyl or a heterocyclic $R_4$ member or together with the carbon atom to which they are attached may form a $C_3$-$C_7$ spirocycloalkyl group.

Preferred members according to Formula III are those wherein $R_4$ is one of said heterocyclic members and $R_5$ and $R_6$ are independently methyl, trifluoromethyl or when combined with the carbon atom to which attached form a $C_5$ or $C_6$ cycloalkyl radical.

Preferred antidotal compounds according to Formula III are the following compounds:
Oxazolidine, 3-(dichloroacetyl)-2,2,5-trimethyl-,
Oxazolidine, 3-(dichloroacetyl)-2,2-dimethyl-5-phenyl-,
Oxazolidine, 3-(dichloroacetyl)-2,2-dimethyl-5-(2-furanyl)-,
Oxazolidine, 3-(dichloroacetyl)-2,2-dimethyl-5-(2-thienyl)-, Pyridine,3-[3-(dichloroacetyl)-2,2-dimethyl-5-oxazolidinyl]-,
4-(dichloroacetyl)-1-oxa-4-azaspiro-(4,5)-decane.

Another group of dichloroacetamide antidotal compounds according to Formula II are the following compounds:
4-(Dichloroacetyl)-3,4-dihydro-3-methyl-2H-2,4-benzoxazine,
Ethanone, 2,2-dichloro-1-(1,2,3,4-tetra-hydro-1-methyl-2-isoquinolinyl)-,
Cis/trans-piperazine, 1,4-bis(dichloroacetyl)-2,5-dimethyl-,
N-(Dichloroacetyl)-1,2,3,4-tetrahydroquinaldine,
1,5-Diazacyclononane, 1,5-bis(dichloroacetyl,
1-Azaspiro[4,4]nonane, 1-(dichloroacetyl).

Still another preferred group of antidotal compounds are the following which have a structure not according to Formula II:
α-[(Cyanomethoxy)imino]benzeneacetonitrile,
α-[(1,3-Dioxolan-2-yl-methoxy)imino]benzeneacetonitrile,
O-[1,3-Dioxolan-2-ylmethyl]-2,2,2-trifluoromethyl-4'-chloroacetophenone oxime,
Benzenemethamine, N-[4-(dichloromethylene)-1,3-ditholan-2-ylidene]-α-methyl, hydrochloride,
Diphenylmethoxy acetic acid, methyl ester,
1,8-Naphthalic anhydride,
4,6-Dichloro-2-phenyl-pyrimidine,
2-Chloro-N-[1-(2,4,6-trimethylphenyl)ethenyl]-acetamide, and
Ethylene glycol acetal of 1, 1-dichloroacetone.

The herbicidal and antidotal compounds of Formulae I–V are known in the art. The sub-group of 1,3-oxazolidine dichloroacetamides of Formula III are the subject of copending application, Ser. No. 07/212,621, of common assignment herewith, priority application for EP 304409 published Feb. 22, 1989.

The term "haloalkyl" embraces radicals wherein any one or more of the carbon atoms, preferably from 1 to 4 in number, is substituted with one or more halo groups, preferably selected from bromo, chloro and fluoro. Specifically embraced by the term "haloalkyl" are monohaloalkyl, dihaloalkyl and polyhaloalkyl groups. A monohaloalkyl group, for example, may have either a bromo, a chloro, or a fluoro atom within the group. Dihaloalkyl and polyhaloalkyl groups may be substituted with two or more of the same halo groups, or may have a combination of different halo groups. A dihaloalkyl group, for example, may have two bromo atoms, such as a dibromomethyl group, or two chloro atoms, such as a dichloromethyl group, or one bromo atom and one chloro atom, such as a bromochloromethyl group. Examples of a polyhaloalkyl are perhaloalkyl groups such as trifluoromethyl and perfluoroethyl groups.

Where in Formulae III–V the halogen attached to the acetyl radical is the chlorine ion, it is contemplated that the other halogens, i.e., bromo, iodo or fluoro may be substituted for the chloro.

Preferred haloalkyl R members of Formula II are dihalomethyl, particularly dichloromethyl, while the preferred haloalkyl $R_1$ member is a tri-halogenated methyl radical, preferably trifluoromethyl.

Where the term "alkyl" is used either alone or in compound form (as in "haloalkyl"), it is intended to embrace linear or branched radicals having up to four carbon atoms, the preferred members being methyl and ethyl.

By "agriculturally-acceptable salts" of the compounds defined by the above formula is meant a salt or salts which readily ionize in aqueous media to form a cation of said compounds and a salt anion, which salts have no deleterious effect on the antidotal properties of said compounds or of the herbicidal properties of a given herbicide and which permit formulation of the herbicide-antidote composition without undue problems of mixing, suspension, stability, applicator equipment use, packaging, etc.

By "antidotally-effective" is meant the amount of antidote required to reduce the phytotoxicity level or effect of a herbicide, preferably by at least 10% or 5%, but naturally the greater the reduction in herbicidal injury the better.

By "herbicidally-effective" is meant the amount of herbicide required to effect a meaningful injury or destruction to a significant portion of affected undesirable plants or weeds. Although of no hard and fast rule, it is desirable from a commercial viewpoint that 80–85% or more of the weeds be destroyed, although commercially significant suppression of weed growth can occur at much lower levels, particularly with some very noxious, herbicide-resistant plants.

The terms "antidote", "safening agent", "safener", "antagonistic agent", "interferant", "crop protectant" and "crop protective", are often-used terms denoting a compound capable of reducing the phytotoxicity of a herbicide to a crop plant or crop seed. The terms "crop protectant" and "crop protective" are sometimes used to denote a composition containing as the active ingredients, a herbicide-antidote combination which provides protection from competitive weed growth by reducing herbicidal injury to a valuable crop plant while at the same time controlling or suppressing weed growth occurring in the presence of the crop plant. Antidotes protect crop plants by interfering with the herbicidal action of a herbicide on the crop plants so as to render the herbicide selective to weed plants emerging or growing in the presence of crop plants.

Herbicides which may be used as co-herbicides with the benzoic acid derivatives of Formula I with benefit in combination with an antidote as described herein include, preferably, thiocarbamates (including dithiocarbamates), α-haloacetamides, heterocyclyl phenyl ethers (especially phenoxypyrazoles), imidazolinones, pyridines and sulfonylureas. It is within the purview of this invention that other classes of herbicides, e.g., triazines, ureas, diphenyl ethers, nitroanilines, thiazoles, isoxazoles, pyrrolidinones, aromatic and heterocyclic di- and triketones, etc., the individual members of which classes may be derivatives having one or more substituents selected from a wide variety of radicals may suitably be used as co-herbicides. Such combinations can be used to obtain selective weed control with low crop injury in several varieties of monocotyledonous crop plants such as corn, grain sorghum (milo), and cereals such as wheat, rice, barley, oats, and rye, as well as several varieties of dicotyledonous crop plants including oil-seed crops such as soybeans and cotton. Particular utility for the antidotal compounds of this invention has been experienced with various herbicides in corn, sorghum and soybeans.

Examples of important thiocarbamate herbicides are the following:
cis-/trans-2,3-dichloroallyl-diisopropylthiolcarbamate (common name "diallate");

Ethyl dipropylthiocarbamate (common name "EPTC");
S-ethyl diisobutyl (thiocarbamate) (common name "butylate");
S-propyl dipropyl(thiocarbamate) (common name "vernolate");
2,3,3-trichloroallyl-diisopropylthiolcarbamate (common name "triallate").

Examples of important acetamide herbicides are the following:
2-chloro-N-isopropylacetanilide (common name "propachlor");
2-chloro-1',6'-diethyl-N-(methoxymethyl)acetanilide (common name "alachlor");
2-chloro-2',6'-diethyl-N-(butoxymethyl)acetanilide (common name "butachlor");
2-chloro-N-(ethoxymethyl)-6'-ethyl-o-acetotoluidide (common name "acetochlor");
ethyl ester of N-chloroacetyl-N-(2,6-diethylphenyl)glycine (common name "diethatylethyl");
2-chloro-N-(2,6-dimethylphenyl)-N-(2-methoxyethyl)acetamide (common name "dimethachlor");
2-chloro-N-(2-n-propoxyethyl)-2',6'-diethylacetanilide (common name "pretilachlor");
2-chloro-N-(2-methoxy-1-methylethyl)-6'-ethylo-acetotoluidide (common name "metolachlor");
2-chloro-2',6'-dimethyl-N-(1-pyrazol-1-ylmethyl)acetanilide (common name "metazachlor");
2-chloro-N-(2,6-dimethyl-1-cyclohexen-1-yl)-N-(1H-pyrazol-1-ylmethyl)acetamide;
2-chloro-N-isopropyl-1- (3,5,5-trimethylcyclohexen-1-yl)acetamide (common name "trimexachlor");
2-Chloro-2'-methyl-6'-trifluoromethyl-N-(ethoxymethyl)acetanilide.

Examples of important pyridine herbicides include:
3-pyridinecarboxylic acid, 2-(difluoromethyl)-5-4,5-dihydro-2-thiazolyl-4-(2-methylpropyl)-6-(trifluoromethyl)-, methyl ester;
3-pyridinecarboxylic acid, 2-(difluoromethyl)4-(2-methylpropyl)-5-(1H-pyrazol- 1-ylcarbonyl)-6-(trifluoromethyl)-, methyl ester;
3,5-pyridinedicarboxylic acid, 2-(difluoromethyl)-4-(2-methylpropyl)-6-trifluoromethyl, dimethyl ester.
3,5-pyridine dicarbothioic acid, 2-(difluoromethyl)-4-(2-methylpropyl)-6-(trifluoromethyl)-, S,S-dimethyl ester.

Examples of important heterocyclyl phenyl ethers include:
5-(trifluoromethyl)-4-chloro-3-(3 -[1-ethoxycarbonyl]-ethoxy-4'-nitrophenoxy)-1-methylpyrazol;
5-(trifluoromethyl)-4-chloro-3-(3'-methoxy4'-nitrophenoxy)-1-methylpyrazole;
5-(trifluoromethyl)-4-chloro-3-(3'-[1-butoxycarbonyl]-ethoxy-4'-nitrophenoxy)-4-methylpyrazol;
5-(trifluoromethyl)-4-chloro-3-(3'-methylsulfamoylcarbonyl propoxy-4'-nitrophenoxy)-4methylpyrazol;
5-(trifluoromethyl)-4-chloro-3-(3'-propoxycarbonylmethyloxime-4'-nitrophenoxy)-1-methylpyrazole;
(±)-2-[4-[[5-(trifluoromethyl)-2-pyridinyl]-oxy]phenoxy]propanoic acid (9CI).

Examples of important sulfonylureas include:
Benezenesulfonamide, 2-chloro-N-[[(4-methoxy-6methyl-1,3,5-triazin-2yl)amino]carbonyl];
Benzoic acid, 2[[[[(4-chloro-6-methoxy-2-pyrimidinyl)amino]caronyl]amino]sulfonyl]-ethyl ester;
2-Thiophenecarboxylic acid, 3-[[[[(4,6-dimethoxy-1,3,5-triazin-2-yl)amino]carbonyl]amino]sulfonyl]-, methyl ester;
Benzoic acid, 2-[[[[(4,6-dimethyl-2-pyrimidinyl)amino]-carbonyl]amino]sulfonyl]methyl ester;
Benzenesulfonamide, 2-(2-chloroethoxy)-N-[[(4-methoxy-6-methyl- 1,3,5-triazin-2-yl)amino]-carbonyl];
Benzoic acid , 2-[[[[(4-methoxy-6-methyl- 1,3,5-triazin-2-yl)amino]carbonyl ]amino]sulfonyl]-methyl ester;

Examples of important imidazolinone herbicides include:
3-Quinolinecarboxylic acid, 2-[4,5-dihydro-4-methyl-4-(1-methylethyl)-5-oxo-1H-imidazol2-yl]-;
3-Pyridinecarboxylic acid, 2-4,5-dihydro-4-methyl-4-(1-methylethyl)-5-oxo-1H-imidazol-2-yl]-;
Benzoic Acid, 2-[4,5-dihydro-4-methyl-4-(1-methylethyl)-5-oxo-1H-imidazol-2-yl]-4(or 5)-methyl;
3-pyridinecarboxylic acid, 5-ethyl-2-[4-methyl-4-(1-methylethyl)-5-oxo-1H-imidazol-2-yl]-;
3-pyridinecarboxylic acid, 2-[4,5-dihydro-4-methyl-4-(1-methylethyl)-5-oxo-1H-imidazol-2-yl]-5-methyl-, ammonium salt;
2-(5-Methyl-5-trifluoromethyl-1-H-imidazol-4-on-2-yl)-pyridin-3-carboxylic acid;
2-(5-Methyl-5-trifluoromethyl-1H-imidazol-4-on-2-yl)5-(m)ethyl isonicotinic acid;
2-[5-(1-Fluoroethyl)-5-(m)ethy 1H-imidazol-4-on-2-yl isonicotinic acid;
2-(5- (Difluoromethyl-5-(m)ethyl-1H-imidazol-4-on-2-yl]-5-(m)ethyl-isonicotinic acid;
2-(5-(1-Fluoroethyl)-5-(m)ethyl)-imidazol-4-on-2-yl]isonicotinic (m)ethyl ester;

Examples of other important herbicides include:
2-Chloro-4-(ethylamino)-6-(isopropylamino)symtriazine;
4-Amino-6-tertbutyl-3-(methylthio)AS-triazine-5(4H)one;
Trifluoro-2,6-dinitro-N,N-dipropyl-p-toluidine;
Benzeneamine, N-(1-ethylpropyl)-3,4-dimethyl-2,6-dinitro-;
2-Pyrrolidinone, 3-chloro-4-(chloromethyl)-[3-(trifluoromethyl)phenyl], trans-;
3-Isoxazolidinone, 2-[(2-chlorophenyl)methyl]-4,4-dimethyl-;
2-Imidazolidinone, 3-[5-(1,1-dimethylethyl)-3-isoxazolyl]-4-hydroxy-1-methyl-;
2-Chloro-4-(1-cyano-1-methylethylamino)-6-ethylamino-1,3,5-triazine;
Methyl 5-(2,4-dichlorophenoxy)-2-nitrobenzoate;
1'-(Carboethoxy)ethyl-5-[2-chloro-4-(trifluoromethyl)-phenoxy]-2-nitrobenzoate;
Ammonium-DL-homoalanin-4-yl(methyl)phosphinate;
2-(3,4-Dichlorophenyl)-4-methyl-1,2,4-oxadiazolidine-3,5-dione.

The herbicides of particular and preferred interest as co-herbicides with the benzoic acid derivatives of Formula I in compositions with antidotes according to this invention include each of the abovementioned species from different chemical classes of compounds exemplified as important herbicides, particularly those of current commercial interest and use and those which may be determined of commercial utility. Co-herbicidal compounds of preference include the following:
alachlor,
acetochlor,
butachlor,
metolachlor,
pretilachlor
metazachlor, and 2-chloro-2',6'-dimethyl-N-(2-methoxyethyl)-acetanilide.

All of the above specifically-named herbicides are known in the art.

As further detailed infra, while not necessary, the composition containing the herbicideantidote combination may also contain other additaments, e.g., biocides such as insecticides, fungicides, nematocides, miticides, etc., fertilizers, inert formulation aids, e.g., surfactants, emulsifiers, defoamers, dyes, etc.

Combinations may be made of any one or more of the described antidote compounds with any one or more of the herbicide compounds of Formula I and co-herbicides mentioned herein.

It will be recognized by those skilled in the art that all herbicides have varying degrees of phytotoxicity to various plants because of the sensitivity of the plant to the herbicide. Thus, e.g., although certain crops such as corn and soybeans have a high level of tolerance (i.e., low sensitivity) to the phytotoxic effect of alachlor, other crops, e.g., milo (grain sorghum), rice and wheat, have a low level of tolerance (i.e., high sensitivity) to the phytotoxic effects of alachlor. The same type of sensitivity to herbicides as shown by crop plants is also exhibited by weeds, some of which are very sensitive, others very resistant to the phytotoxic effects of the herbicide.

When the sensitivity of a crop plant to a herbicide is low, whereas the sensitivity of a weed to that herbicide is high, the "selectivity factor" of the herbicide for preferentially injuring the weed while not injuring the crop is high.

In an analogous manner, but more complex, an antidotal compound may, and commonly does, have varying degrees of crop protective effect against different herbicides in different crops. Accordingly, as will be appreciated by those skilled in the art, the various antidotes of this invention, as with all classes of antidotal compounds, will have greater or lesser crop safening effects against various herbicides in various crops than in others. Thus, while a given antidotal compound may have no crop protective ability against a given herbicide in a given crop, that same antidotal compound may have a very high crop protective ability against the same given herbicide in a different crop or against a different herbicide in the same crop. This is an expected phenomenon.

DETAILED DESCRIPTION OF THE INVENTION

Antidote Compounds

As mentioned earlier, the antidotal compounds used in the practice of this invention are known compounds. The preferred compounds used herein are the 1,3-oxazolidine dichloroacetamides according to Formula III wherein the $R_4$ member is a heterocyclic radical. Those compounds are separately disclosed and claimed in the assignee's said copending application, Ser. No. 07/212,621 and its corresponding EP 304409, published Feb. 22, 1989. The synthesis methods of said EP 304409 for said 1,3-oxazolidine dichloroacetamide antidotes are also disclosed in U.S. Ser. No. 07/226,928, an ancestor in the continuity chain of this application, and the foregoing documents are hereby incorporated by reference.

Biological Evaluation

Effective weed control coupled with low crop injury is a result of treatment of a plant locus with a combination of herbicide compound and antidote compound. By application to the "plant locus" is meant application to the plant growing medium, such as soil, as well as to the seeds, emerging seedlings, roots, stems, leaves, or other plant parts.

The phrase "combination of herbicide compound and antidote compound" embraces various methods of treatment. For example, the soil of a plant locus may be treated with a "tank-mix" composition containing a mixture of the herbicide and the antidote which is "in combination". Or, the soil may be treated with the herbicide and antidote compounds separately so that the "combination" is made on, or in, the soil. After such treatments of the soil with a mixture of herbicide and antidote or by separate or sequential application of the herbicide and antidote to the soil, the herbicide and antidote may be mixed into or incorporated into the soil either by mechanical mixing of the soil with implements or by "watering in" by rainfall or irrigation. The soil of a plant locus may also be treated with antidote by application of the antidote in a dispersible-concentrate form such as a granule. The granule may be applied to a furrow which is prepared for receipt of the crop seed and the herbicide may be applied to the plant locus either before or after in-furrow placement of the antidote-containing granule so that the herbicide and antidote form a "combination". Crop seed may be treated or coated with the antidote compound either while the crop seed is in-furrow just after seeding or, more commonly, the crop seed may be treated or coated with antidote prior to seeding into a furrow. The herbicide may be applied to the soil plant locus before or after seeding and a "combination" is made when both herbicide and antidote-coated seed are in the sol. Also contemplated as a "combination" is a commercially-convenient association or presentation of herbicide and antidote. For example, the herbicide and antidote components in concentrated form may be contained in separate containers, but such containers may be presented for sale or sold together as a "combination". Or, the herbicide and antidote components in concentrated form may be in a mixture in a single container as a "combination". Either such "combination" may be diluted or mixed with adjuvants suitable for soil applications. Another example of a commercially-presented combination is a container of antidote-coated crop seed sold, or presented for sale, along with a container of herbicide material. These containers may, or may not, be physically attached to each other, but nonetheless constitute a "combination of herbicide and antidote" when intended for use ultimately in the same plant locus.

In the foregoing description of various modes of application of the herbicide-antidote combinations, it is inherent that each form of application requires that in some manner, the herbicide and antidote will physically combine to form a "composition" of those agents.

The amount of antidote employed in the methods and compositions of the invention will vary depending upon the particular herbicide with which the antidote is employed, the rate of application of the herbicide, the particular crop to be protected, and the manner of application to the plant locus. In each instance the amount of antidote employed is a safening-effective amount, that is, the amount which reduces, or protects against, crop injury that otherwise would result from the presence of the herbicide. The amount of antidote employed will be less than an amount that will substantially injure the crop plant.

The antidote can be applied to the crop plant locus in a mixture with the selected herbicide. For example, where the crop seed is first planted, a suitable mixture of antidote and herbicide, whether in a homogeneous liquid, emulsion, suspension or solid form, can be applied to the surface of, or incorporated in, the soil in which the seed has been planted. Or, the herbicide-antidote mixture may be applied to the soil, and then the seed thereafter "drilled" into the soil below the soil layer containing the herbicide-antidote mixture. The herbicide will reduce or eliminate the presence of undesirable weed plants. Where the herbicide would by itself injure the crop seedlings, the presence of the antidote will reduce or eliminate the injury to the crop seed caused by the herbicide. It is not essential that the application of herbicide and the antidote to the plant locus be made using the selected herbicide and antidote in the form of a mixture or composition. The herbicide and the antidote may be applied to the plant locus in a sequential manner. For example, the antidote may be first applied to the plant locus and thereafter the herbicide is applied. Or, the herbicide may be first applied to the plant locus and thereafter the antidote is applied.

The ratio of herbicide to antidote may vary depending upon the crop to be protected, weed to be inhibited, herbicide used, etc., but normally a herbicide-to-antidote ratio ranging from 1:25-to-60:1 (preferably 1:5-to-30:1) parts by weight may be employed, although much higher rates of antidote may be used, e.g., 1:100–1:300 parts by weight of herbicide-to-antidote. As indicated above, the antidote may be applied to the plant locus in a mixture, i.e., a mixture of a herbicidally-effective amount of herbicide and a safening-effective amount of an antidote, or sequentially, i.e., the plant locus may be treated with an effective amount of the herbicide followed by a treatment with the antidote or vice versa. In general, effective herbicidal amounts are in the range of about 0.03 to about 12 kilograms/hectare, but rates as low as 0.004 kg/ha may be used effectively. The preferred range of rate of application is from about 0.1 to about 10 kg/ha. Preferably, antidote application rates range from about 0.5 kg/ha down to about 0.05 kg/ha. It will be appreciated that at times amounts either below or above these ranges will be necessary to obtain the best results. The selection of the herbicide to inhibit the emergence and growth of weeds depends upon the species of weeds to be controlled and the crop to be protected.

The application of the antidote can be made directly to the seed before planting. In this practice, a quantity of crop seed is first coated with the antidote. The coated seed is thereafter planted. The herbicide may be applied to the soil before or after the coated seed is planted.

In field applications, the herbicide, antidote, or a mixture thereof, may be applied to the plant locus without any adjuvants other than a solvent. Usually, the herbicide, antidote, or a mixture thereof, is applied in conjunction with one or more adjuvants in liquid or solid form. Compositions or formulations containing mixtures of an appropriate herbicide and antidote usually are prepared by admixing the herbicide and antidote with one or more adjuvants such as diluents, solvents, extenders, carriers, conditioning agents, water, wetting agents, dispersing agents, or emulsifying agents, or any suitable combination of these adjuvants. These mixtures may be in the form of particulate solids, granules, pellets, wettable powders, dusts, solutions, aqueous dispersions, or emulsions.

Application of the herbicide, antidote, or mixture thereof, can be carried out by conventional techniques utilizing, for example, hand-carried or tractor-mounted spreaders, power dusters, boom and hand sprayers, spray dusters, and granular applicators. If desired, application of the compositions of the invention to plants can be accomplished by incorporating the compositions in the soil or other media.

The following examples describe preparation of exemplary formulations of herbicide and antidote and mixtures thereof.

EXAMPLE 1

An emulsifiable concentrate type formulation containing acetochlor was prepared containing the following components:

|  | % by wt. |
|---|---|
| Acetochlor (93.1% technical) | 87.13 |
| Epoxy soybean oil | 0.91 |
| Witco C-5438 emulsifier (blend of anionic/non-ionic emulsifiers in ethylene glycol); Witco Chemical Co., New York, N.Y. | 9.00 |
| Orchex 796 (a spray oil filter) | 2.93 |
| GE AG-78 antifoaming agent (polysiloxane); General Electric Co., Waterford, N.Y. | 0.02 |
| Methyl violet dye; Dye Specialties Co., Jersey city, N.J. | 0.01 |

These components were mixed together at room temperature until a uniform blend was obtained. The formulation had a specific gravity of 1.1101 observed at 20° C. and calculated against water at 15.6° C., and had a flash point above 200° C. (tag closed-cup method). The formulation showed fair emulsion bloom at water hardness concentrations of 114 ppm, 342 ppm and 1000 ppm. The emulsions had 1 ml cream after one hour at each water hardness concentration. The formulation was a purple viscous liquid and contained 87.13% by weight of acetochlor.

EXAMPLE 2

An emulsifiable concentrate formulation containing 4-(dichloroacetyl) 1-oxa-4-azaspiro (4,5) decane, having the common name "AD-67" as the antidote compound was prepared for use in various tests. AD-67 is also named oxazolidine, 3-(dichloroacetyl)-2,2-spirocyclohexyl-. The formulation contained the following ingredients:

|  | % by wt. |
|---|---|
| AD-67 (93.5% tech) | 11.44 |
| Sterox NJ | 0.77 |
| FLOMO 54C | 5.96 |
| FLOMO 50H emulsifier | 3.27 |
| Monochlorobenzene | 78.55 |

These components were mixed together at room temperature until a uniform blend was obtained. The formulation had a specific gravity of 1.222 observed at 20° C. calculated against water at 15.6° C., a solution point of $<0°$ C., and a flash point less than 32° C. The formulation showed good bloom at a concentration in water of 1000 ppm, and perfect bloom at 100 and 342 ppm. Emulsions containing 5% of the formulation were observed one hour after preparation as having a trace cream layer at 114 ppm, and 2 ml layer at 342 ppm and at 1000 ppm water-hardness concentrations.

EXAMPLE 3

An emulsifiable concentrate formulation containing oxazolidine, 3-(dichloroacetyl)-2,2-dimethyl-(5-furanyl)-, was prepared for use in field tests as described later herein. This EC contained the following ingredients:

|  | % by wt. |
|---|---|
| Active ingredient (the above compound) | 10.77 |
| Monochlorobenzene | 79.23 |
| Witconate P 1220 | 4.19 |
| Witconol CO-360 | 5.45 |
| Witconol NP-330 | 0.36 |

The above formulation had a specific gravity of 1.1220 at 20° C. calculated against water at 15.6° C. and a flash point of 37.8° C. (100° F.). The formulation exhibited poor bloom in water at concentrations of 114, 342 and 1000 ppm. Emulsions containing 5% of this formulation exhibited a 1 ml layer at the 114 and 342 ppm concentrations and a 10 ml layer at the 1000 ppm concentration.

EXAMPLE 4

Commercially-available formulations of two other herbicides were used in tests herein. An alachlor formulation contained 45.1% by wt. of active ingredient and 54.9% by wt. of inerts. A formulation of dicamba containing 60.2% by wt. of active ingredient and 39.8% by wt. of inerts was used in the tests of Examples 6–9

Where not expressly stated in the tables of data herein, it is to be understood that all application rates of herbicides and antidotes are to be read in kg/ha.

EXAMPLE 5

Formulations as prepared above for testing to determine the comparative effects of herbicide alone, herbicide and antidote in combination, and antidote alone. The herbicide and/or antidote formulations were applied by tank-mix spraying. For the formulations used in Examples 6–8, a tractor-mounted tank was used. For the herbicide formulations containing no antidote, an appropriate amount of a water-soluble salt (dicamba) or emulsifiable concentrate (EC) was added directly to a tank containing the appropriate amount of water. For the antidote-containing tank-mix formulations, the antidote in emulsifiable form was added to a water-containing tank. Then for the herbicide + antidote formulation, antidote emulsifable concentrate was added to a tank containing one or more herbicides and an appropriate amount of water. Each tank-mix formulation was agitated sufficiently to ensure a uniform suspension. The relative amounts of water, herbicide soluble salt, emulsifiable concentrate, or antidote, added to the tank were calculated for each formulation based upon a formulation spraying rate of 281 l/ha (30 gal/acre) for tractor spraying and 187 l/ha (20 gal/ac) for backpack spraying in order to achieve various field application rates of herbicide and antidote, as appropriate, for the rates shown in tables I–IV. Each formulation was sprayed on three replicate plots, with a small-plot tractor-mounted sprayer with a 3 meter (10 ft) boom delivering 281 l/ha (30 gal/ac) at 2 atm pressure (30 psi), or a back-pack sprayer delivering 187 l/ha (20 gal/ac). The treatments were made to the surface of the topsoil or, in some cases, incorporated to a depth of about 5–10 cm (2–4 in.) and were selected in a random manner in order to normalize variations in plot soil conditions.

Three control plots were established which were not treated with herbicide or antidote formulations.

Evaluations of safening activity of the antidotal compounds were carried out using the procedures described in Example 6–9 below. Evaluations of biological response as reported in Tables I–V were made by visual comparison of crop and weed plants treated with and without herbicide and/or antidotes. Values were assigned to this visual comparison in terms of percent injury or inhibition to the plants. In Tables I–IVA the data shown are for the herbicides alone or mixtures thereof with other herbicides and/or antidotes.

The degree of reduction of herbicide injury provided by an antidote compound is indicated by the magnitude of the difference between plant injury without the safener and plant injury with the safener. From these plant injury values, one can evaluate the "safening effect" provided by the antidote. The safening effect is determined by dividing the percentage difference between herbicidal injury without the antidote and the injury with the antidote present by the percent injury without the antidote multiplied by 100.

EXAMPLE 6

This example describes a field test in Janeville, Wis. in which were used emulsifiable concentrates of two herbicides (alachlor and acetochlor) and the antidotal compound AD-67, while another herbicide, dicamba, was formulated as a water-soluble salt. Combinations of these formulations were used wherein the herbicides were tested separately and in mixtures thereof without the antidote and formulations of those herbicides with the antidote.

The above formulations were applied in both surface application (PRE) and preplant incorporated (PPI) modes in side-by-side rows in a plot size of 4.25 m² (150 ft²) to determine their relative inhibition of grassy (narrow leaf) and broadleaf plants. Four rows of DeKalb corn were seeded at a depth of about 1 to 2 inches (2.54–5.08 cm) in silt loam soil having an organic matter content of 4.1%. The test plots were sprayed with a tractor as described in Example 5.

Field conditions at time of treatment
Wind speed: 9.7 km/hr (6 mph)
Air temperature: 21.1° C. (70° F.)
Soil temperature: 16.1° C. (61° F.)
Relative humidity: 29%
Soil condition: Dry surface; moisture at 3.8 cm (1.5 in.)

Evaluations of herbicidal activity were made 21 days after treatment (DAT). Results are shown in Tables I (PPI treatment) and IA (surface application treatment) in which the following symbols are used:
Test Formulation.
I Alachlor EC
II Acetochlor EC
III Dicamba Sol. Salt
IV AD-67 EC
Test Plants
C Corn
GF Giant foxtail—Setaria viridis
VL Velvetleaf—Abutilon theophrasti RP Redroot pigweed—*Amaranthus retroflexus*

TABLE I

| Formulation | Rate[1] (Kg/Ha) | % Inhibition - 21 DAT (Avg. 3 reps) | | | |
|---|---|---|---|---|---|
| | | C | GF | VL | RP |
| check | — | 0 | 0 | 0 | 0 |
| I | 2.8 | 0 | 92 | 63 | 98 |
| II | 2.24 | 0 | 88 | 90 | 100 |
| III | 0.56 | 3 | 75 | 82 | 96 |
| I<br>III | 2.8<br>0.56 | 0 | 93 | 97 | 100 |
| III<br>II | 0.56<br>2.24 | 22 | 98 | 98 | 100 |
| I<br>IV | 2.8<br>0.28 | 0 | 87 | 80 | 67 |
| III<br>IV | 0.56<br>0.056 | 0 | 88 | 89 | 95 |
| II<br>IV | 2.24<br>0.34 | 0 | 93 | 88 | 95 |
| III<br>IV<br>I | 0.56<br>0.28<br>2.8 | 15 | 95 | 100 | 100 |
| III<br>II<br>IV | 0.56<br>2.24<br>0.28 | 0 | 100 | 99 | 100 |

[1]PPI application

TABLE IA

| Formulation | Rate[2] (Kg/Ha) | % Inhibition - 21 DAT (Avg. 3 reps) | | | |
|---|---|---|---|---|---|
| | | C | GF | VL | RP |
| check | — | 0 | 0 | 0 | 0 |
| I | 2.8 | 0 | 75 | 0 | 100 |
| II | 2.24 | 0 | 85 | 58 | 98 |
| III | 0.56 | 0 | 67 | 95 | 95 |
| I<br>III | 2.8<br>0.56 | 0 | 67 | 77 | 100 |
| III<br>II | 0.56<br>2.25 | 0 | 98 | 100 | 100 |
| I<br>IV | 2.8<br>0.28 | 0 | 87 | 0 | 82 |
| III<br>IV | 0.56<br>0.056 | 0 | 75 | 90 | 100 |
| II<br>IV | 2.24<br>0.34 | 0 | 88 | 25 | 93 |
| III<br>IV<br>I | 0.56<br>0.28<br>2.8 | 0 | 92 | 89 | 100 |
| III<br>II<br>IV | 0.56<br>2.24<br>0.28 | 0 | 96 | 97 | 97 |

[2]Surface application

An important point to note in Table I is the reduction in corn injury by the combination of dicamba (III) and acetochlor (II) herbicides from 22% to 0 when 0.28 kg/ha of AD-67 (IV) antidote is added, with no reduction in control of the weed species.

EXAMPLE 7

In another field test at a test site in Hancock, Wis., the above formulations were evaluated for their biological performance against the broadleaved plants common ragweed (*Ambrosia artemisiifolia*) and common lambsquarters (*Chenopodium album*) in the presence of corn.

The general test procedure and plot size described in Example 6 was followed with certain modifications. In this test the corn was of the variety PI-3475; seeding depth for the PPI and surface application tests was 2 in. (5.08 cm); soil texture was sandy and having an organic matter content of 1.0%. The test formulations were applied with a tractor-mounted sprayer at a rate of 281 l/ha (30 gal/ac).

Field conditions for this test at treatment:

Wind speed: 16.1 km/hr (10 mph)
Air temperature: 21.1° C. (70° F.)
Soil temperature: 16.7° C. (62° F.)
Relative humidity: 46%
Soil condition: moist
Irrigation: sprinkler Results of the test in this example are shown in Tables II (PPI treatment) and IIA (surface application). The formulation symbols used in Example 44 are used in these tables. The weed symbols are CR for Common ragweed and CL for Common lambsquarters; again C represents corn.

TABLE II

| Formulation | Rate[1] (Kg/Ha) | % Inhibition (Avg. 3 reps) | | |
|---|---|---|---|---|
| | | C (21 DAT) | CL (22 DAT) | CR (22 DAT) |
| check | — | 0 | 0 | 0 |
| I | 2.8 | 10 | 88 | 62 |
| III | 0.56 | 17 | 82 | 67 |
| II | 2.24 | 22 | 80 | 88 |
| I<br>III | 2.8<br>0.56 | 8 | 93 | 80 |
| III<br>II | 0.56<br>2.24 | 33 | 93 | 92 |
| I<br>IV | 2.8<br>0.28 | 0 | 87 | 17 |
| III<br>IV | 0.56<br>0.056 | 0 | 42 | 73 |
| II<br>IV | 2.24<br>0.34 | 0 | 88 | 85 |
| III<br>IV | 0.56<br>0.28 | 0 | 92 | 92 |
| I<br>III<br>II<br>IV | 2.8<br>0.56<br>2.24<br>0.28 | 10 | 95 | 88 |

[1]PPI Treatment

TABLE IIA

| Formulation | Rate[2] (Kg/Ha) | % Inhibition (Avg. 3 reps) | | |
|---|---|---|---|---|
| | | C (21 DAT) | CL (22 DAT) | CR (22 DAT) |
| check | — | 0 | 0 | 0 |
| I | 2.8 | 0 | 93 | 77 |
| III | 0.56 | 42 | 90 | 93 |
| II | 2.24 | 20 | 100 | 98 |
| I<br>III | 2.8<br>0.56 | 50 | 100 | 100 |
| III<br>II | 0.56<br>2.24 | 50 | 100 | 100 |
| I<br>IV | 2.8<br>0.28 | 0 | 95 | 70 |
| III<br>IV | 0.56<br>0.056 | 20 | 95 | 92 |
| II<br>IV | 2.24<br>0.34 | 0 | 100 | 100 |
| III<br>IV | 0.56<br>0.28 | 12 | 100 | 97 |
| I<br>III<br>II<br>IV | 2.8<br>0.56<br>2.24<br>0.28 | 38 | 100 | 100 |

[2]Surface application

Noteworthy results are particularly shown in Table II where dicamba injury to corn is reduced from 17% to 0% when AD-67 is present in as little as 0.056 kg/ha (0.05 lb/ac.). Another significant reduction in corn injury is shown where the herbicidal combination of dicamba and acetochlor caused 33% injury without the safener, but when 0.28 kg/ha (0.25 lb/ac) AD-67 was added, corn injury was reduced to 10%, well within acceptable range of 15% maximum injury.

EXAMPLE 8

Still another field test was conducted with the above formulations at a site in Stratford, Wis. to determine the biological response of those formulations against green foxtail (GF) in the presence of corn under yet other test conditions. This test was parallel in procedure to the surface application test described in Example 6 using a tractor to apply the formulations to the soil. Again, the plot size was 4.25 m² (150 ft²) and here the soil texture was a loamy clay having an organic matter content of 3%.

Field conditions for the test at treatment.
Wind speed: 19 km/hr (12 mph)
Air temperature: 7.8° C. (46° F.)
Soil temperature: 12.2° C. (54° F.)
Relative humitidy: 58%
Soil condition: Wet; rained preceding night
Irrigation: None Test results are shown in Table III.

In this test, corn stand counts were made based on the number of plants per 4.9 m (16 ft.), i.e., "Plts/4.9m" in the table.

TABLE III

| Formu-lation | Rate² (Kg/Ha) | Corn Plts/4.9 m (21 DAT) | % Inhibition (Avg. 3 reps) (21 DAT) Corn | Green Foxtail |
|---|---|---|---|---|
| check | — | 17 | 0 | 0 |
| I | 2.8 | 16 | 4 | 85 |
| III | 0.56 | 18 | 0 | 8 |
| II | 2.24 | 13 | 6 | 88 |
| I | 2.8 | 17 | 7 | 93 |
| III | 0.56 | | | |
| III | 0.56 | 11 | 5 | 93 |
| II | 2.24 | | | |
| I | 2.8 | 15 | 0 | 90 |
| IV | 0.28 | | | |
| III | 0.56 | 13 | 0 | 42 |
| IV | 0.056 | | | |
| II | 2.24 | 19 | 9 | 97 |
| IV | 0.34 | | | |
| III | 0.56 | 17 | 3 | 90 |
| IV | 0.28 | | | |
| I | 2.8 | | | |
| III | 0.56 | 19 | 5 | 87 |
| II | 2.24 | | | |
| IV | 0.28 | | | |

²Surface application

The salient point to note in the data of Table III is that the herbicidal combination of dicamba and acetochlor resulted in a corn stand count of only 11 plants/4.9 m, but the addition of a small amount (0.28 kg/ha) of AD-67 resulted in an improved stand count of 19 corn plants/4.9 m, a decided advantage from an agronomic standpoint.

EXAMPLE 9

This example describes a field test conducted at Troy, Mo. to determine the biological response of corn and velvetleaf when treated with the above herbicidal formulations without and with two safeners, viz., AD-67 and oxazolidine, 3-(dichloroacetyl)-2,2-dimethyl-(5-furanyl)-, which latter compound will be designated as formulation V in Table IV A.

In this test the corn variety 3320 and velvetleaf were treated under PPI conditions, the seed being incorporated into the soil at a depth of 3.81 cm (1.5 in.). The various formulations were applied from a back-pack sprayer at a rate of 187 l/ha (20 gal/ac.).

Field conditions at time of treatment
Wind speed: 4.8 km/ha (3 mph)
Air temperature: 28.9° C. (84° F.)
Soil temperature: 23.9° C. (75° F.)
Relative humidity: 60–65%
Soil condition: dry, with moisture at 5.08 cm (2 in.)

The formulation symbols used in the preceding examples will be used in this example together with the added antidote formulation V. The composition of the acetochlor formulation II was modified to comprise the following composition:

| | Wt. % |
|---|---|
| Acetochlor (96%) | 89.35 |
| Witco C-5438 | 10.61 |
| Silicone defoamer | 0.02 |
| Methyl violet dye | 0.17 |

The test results from the Example 9 are shown in Table IV, which includes data for the AD-67 antidote, and in Table IV A, which includes data for the antidotal formulation V.

TABLE IV

| Formu-lation | Rate¹ (Kg/Ha) | % Inhibition (Avg. 3 reps) | | | |
|---|---|---|---|---|---|
| | | Corn DAT | | Velvetleaf DAT | |
| | | 19 | 34 | 19 | 34 |
| check | — | 0 | 0 | 0 | 0 |
| II | 2.24 | 38 | 18 | 100 | 100 |
| III | 0.56 | 10 | 0 | 85 | 73 |
| III | 1.12 | 32 | 18 | 95 | 93 |
| III | 0.56 | 35 | 30 | 98 | 100 |
| II | 2.24 | | | | |
| III | 1.12 | 60 | 60 | 100 | 100 |
| II | 2.24 | | | | |
| IV | 0.22 | 2 | 3 | 13 | 30 |
| IV | 0.11 | 10 | 5 | 100 | 100 |
| II | 2.24 | | | | |
| IV | 0.22 | 12 | 5 | 100 | 98 |
| II | 2.24 | | | | |
| IV | 0.22 | 5 | 5 | 92 | 88 |
| III | 0.56 | | | | |
| IV | 0.11 | 13 | 10 | 93 | 90 |
| III | 1.12 | | | | |
| IV | 0.22 | 5 | 0 | 95 | 88 |
| III | 0.56 | | | | |
| IV | 0.22 | 13 | 8 | 97 | 90 |
| III | 1.12 | | | | |
| IV | 0.11 | 13 | 10 | 98 | 100 |
| III | 0.56 | | | | |
| II | 2.24 | | | | |
| IV | 0.22 | 13 | 13 | 100 | 100 |
| III | 0.56 | | | | |
| II | 2.24 | | | | |
| IV | 0.11 | 43 | 25 | 67 | 50 |
| III | 1.12 | | | | |
| II | 2.0 | | | | |
| IV | 0.22 | 50 | 58 | 100 | 100 |
| III | 1.12 | | | | |
| II | 2.24 | | | | |

¹PPI

Reference to the data in Table IV shows that corn injury by 1.12 kg/ha of dicamba (III) of 32% and 18% at the 19 and 34 DAT observations, respectively, was reduced to 13% and 10%, respectively, when 0.11 kg/ha of AD-67 (IV) was added to the dicamba formulation, without reduction of injury to velvetleaf. A similar reduction in corn injury occurred when 0.22 kg/ha of AD-67 was mixed with the same rate of dicamba. When the dicamba rate was reduced from 1.12 kg/ha to 0.56 kg/ha, corn injury was even more reduced by antidotal action of AD-67 at 0.22 kg/ha without significant reduction in weed control at either 19 or 34 DAT.

Similarly the data in Table IV shows that the herbicidal combination of dicamba and acetochlor caused 60% injury to corn at both the 19 and 34 DAT observations. When 0.11 kg/ha of AD-67 added to the dicamba/acetochlor combination (at the same rates) corn injury was reduced to 43% and 25%, respectively, at 19 and 34 DAT readings.

TABLE IVA

| Formulation | Rate[1] (Kg/Ha) | % Inhibition (Avg. 3 reps) | | | |
|---|---|---|---|---|---|
| | | Corn DAT | | Velvetleaf DAT | |
| | | 19 | 34 | 19 | 34 |
| check | — | 0 | 0 | 0 | 0 |
| II | 2.24 | 38 | 18 | 100 | 100 |
| III | 0.56 | 10 | 0 | 85 | 73 |
| III | 1.12 | 32 | 18 | 95 | 93 |
| V | 0.22 | 0 | 3 | 40 | 25 |
| V | 0.11 | 12 | 5 | 100 | 100 |
| II | 2.24 | | | | |
| V | 0.22 | 12 | 0 | 100 | 98 |
| II | 2.24 | | | | |
| V | 0.11 | 8 | 3 | 98 | 90 |
| III | 0.56 | | | | |
| V | 0.11 | 12 | 10 | 100 | 93 |
| III | 1.12 | | | | |
| V | 0.22 | 13 | 5 | 95 | 88 |
| III | 0.56 | | | | |
| V | 0.22 | 8 | 5 | 98 | 95 |
| III | 1.12 | | | | |
| V | 0.11 | 20 | 13 | 100 | 100 |
| III | 0.56 | | | | |
| II | 2.24 | | | | |
| V | 0.22 | 10 | 8 | 100 | 100 |
| III | 0.56 | | | | |
| II | 2.24 | | | | |
| V | 0.11 | 32 | 15 | 100 | 100 |
| III | 1.12 | | | | |
| II | 2.24 | | | | |
| V | 0.22 | 23 | 20 | 100 | 100 |
| III | 1.12 | | | | |
| II | 2.24 | | | | |

[1]PPI

A number of salient features are apparent from the data in Table IV A. For example, the addition of 0.11 kg/ha of antidote V to 2.24 kg/ha of acetochlor (II) reduced corn injury from 38% to 12% after 19 days and from 18% to 5% 34 DAT. Similarly, injury to corn by 1.12 kg/ha dicamba (III) was reduced from 32% to 8% at 19 DAT and from 18% to 5% at 34 DAT, while slightly increasing the degree of injury to velvetleaf. In like manner, the herbicidal combination of dicamba and acetochlor (0.56:2.24 kg/ha ratio) caused 35% injury to corn 19 DAT and 30% at 34 DAT. The addition of merely 0.11 kg/ha reduced those corn injuries to 20% and 13% respectively at 19 and 34 DAT, while maintaining complete control of velvetleaf. Even when the dicamba rate is increased to 1.12 kg/ha, resulting (in combination with 2.24 kg/ha acetochlor) in 60% injury to corn at both observation dates, the same low concentration of 0.11 kg/ha of antidotal formulation V reduced corn injury to 32% and 15% at the 19 and 34 DAT readings without reducing weed injury.

Other evaluations of safening activity of a wide variety of representative antidote compounds of this invention were carried out using the specific procedures of Examples 10-15 below in greenhouse testing. Measurements of biological response as reported in Tables V-X were made in the following manner. A visual comparison was made between a crop plant treated with a herbicide alone and crop plant having no herbicide or antidote treatment. A number was assigned to this visual comparison indicating the percent injury or inhibition to the herbicide-alone treated crop plant (column "WO" in Table V indicating herbicide "without" antidote). Also, a visual comparison was made between the crop plant treated with herbicide+antidote combination and the crop plant having no herbicide or antidote treatment. A number was assigned to this visual comparison indicating the percent injury or inhibition to the herbicide+antidote treated crop plant (column "W" in Table V indicating herbicide "with" antidote). Observations of response by the weed species to herbicide or herbicide+antidote were similarly recorded. The degree of reduction of herbicide injury provided by an antidote compound is indicated by the magnitude that the plant inhibition number of column "WO" exceeds the corresponding number of column "W". Also reported in Table V are data in parenthesis showing "safening effect" (defined below) for the herbicide+antidote combinations calculated from the plant inhibition numbers. These tables show crop or weed column headings under which there are no data. The lack of such data is not an indication of a failed test; rather it is merely an indication that the particular herbicide+antidote rate combination was not tested with that crop or weed. Listed below are the names of the antidotal compounds for which data reported in Tables V-XXI.

| Antidote No. | Nomenclature |
|---|---|
| 1 | ACETAMIDE, N,N-BIS(2-PROPENYL)-ALPHA,ALPHA-DICHLORO- |
| 2 | -PARA CHLOROPHENYLTHIO-ACETONITRILE |
| 3 | PIPERAZINE,1,4-BIS(DICHLOROACETYL)- |
| 4 | BENZENEMETHANAMINE, N-<4-(DICHLOROMETHYLENE)-1,3-DITHIOLAN-1-YLIDENE>-ALPHA-METHYL-, HYDROCHLORIDE |
| 5 | 1H,3H-NAPHTHO(1,8-cd)PYRAN-1,3-DIONE |
| 6 | PHOSPHONIC ACID, [ALPHA-(DICHLOROACETAMIDO)METHYL]-, DIPHENYL ESTER, |
| 7 | CIS/TRANS-PIPERAZINE, 1,4-BIS(DICHLOROACETYL)-2,5-DIMETHYL-, |
| 8 | PIPERAZINE, 1,4-BIS(DICHLOROACETYL)-2,6-DIMETHYL-, |
| 9 | 5-THIAZOLECARBOXYLIC ACID, 2-CHLORO-4-(TRIFLUOROMETHYL)-, (PHENYLMETHYL) ESTER |
| 10 | 5-THIAZOLECARBOXYLIC ACID, 2-CHLORO-2-CHLORETHYL ESTER, 4-(TRIFLUOROMETHYL)- |
| 11 | OXAZOLIDINE, 3-(DICHLOROACETYL)-2,2,5-TRIMETHYL-, |
| 12 | BENZENEACETONITRILE, ALPHA [(CYANOMETHOXY)IMINO]- |
| 13 | OXAZOLIDINE, 3-(DICHLOROACETYL)-2,2-DIMETHYL-5-PHENYL)- |
| 14 | 5-OXAZOLECARBOXYLIC ACID, 2-[(1,1-DIMETHYLETHYL)AMINO]-4-(TRIFLUOROMETHYL)-, ETHYL ESTER |
| 15 | ACETIC ACID, (DIPHENYLMETHOXY)-, METHYL ESTER |
| 16 | 5-THIAZOLECARBOTHIOIC ACID, 2-CHLORO-4-(TRIFLUOROMETHYL)-S-(PHENYLMETHYL) ESTER |
| 17 | ACETAMIDE, 2,2-DICHLORO-N-[3,5-BIS-(TRIFLUOROMETHYL)PHENYL]- |
| 18 | QUINOLINE, 1-(DICHLOROACETYL)-1,2,3,4-TETRAHYDRO-2-METHYL- |
| 19 | ISOQUINOLINE, 2-(DICHLOROACETYL)-1,2,3,4-TETRAHYDRO- |
| 20 | QUINOLINE, 1-(DICHLOROACETYL)-1,2,3,4-TETRAHYDRO- |
| 21 | QUINOLINE, 1-(DICHLOROACETYL)-1,2-DIHYDRO-2,2,4-TRIMETHYL- |

-continued

| Antidote No. | Nomenclature |
|---|---|
| 22 | ACETAMIDE, 2,2-DICHLORO-N-[2-NITRO-4-(TRIFLUOROMETHYL)PHENYL]- |
| 23 | ACETAMIDE, 2,2-DICHLORO-N-(3-FLUOROPHENYL)- |
| 24 | ACETAMIDE, 2,2-DICHLORO-N-(2,5-DIFLUOROPHENYL)- |
| 25 | 1,4-DIOXA-8-AZASPIRO-(4,5)-DECANE, 8-(DICHLOROACETYL)- |
| 26 | THIAZOLIDINE, 3-(DICHLOROACETYL)- |
| 27 | ACETAMIDE, N-[(1,1'-BIPHENYL)-2-YL]-2,2-DICHLORO- |
| 28 | ACETAMIDE, 2,2-DICHLORO-N-{2-[2-[(DICHLOROACETYL)AMINO]PHENYL}PHENYL]- |
| 29 | BENZENEACETONITRILE, ALPHA-{[(1,3-DIOXOLAN-2-YL)METHOXY]IMINO}-, (AVAILABLE ONLY AS CONCEP II (TM) SORGHUM SEED) |
| 30 | 1-AZASPIRO(4,4)NONAME, 1-BROMOCHLOROACETYL- |
| 31 | ACETAMIDE, 2,2-DICHLORO-N-[(3-METHOXYPHENYL)METHYL]-N-(2-PROPENYL)- |
| 32 | 1-OXA-4-AZASPIRO(4.5)DECANE, 4-(DICHLOROACETYL)- |
| 33 | 1,5-DIAZACYCLONONANE, 1,5-BIS(DICHLOROACETYL)- |
| 34 | ACETAMIDE, N-(1,1'-BIPHENYL)-3-YL-2,2-DICHLORO- |
| 35 | ACETAMIDE, 2-CHLORO-N-[1-(2,6-DICHLOROPHENYL)ETHENYL]- |
| 36 | 1-AZASPIRO(4.4)NONANE, 1-(DICHLOROACETYL)- |
| 37 | ACETAMIDE, 2,2-DICHLORO-N-(1,3-DIOXOLAN-2-YLMETHYL)-N-2-PROPENYL- |
| 38 | 1-OXA-4-AZASPIRO(4.5)DECANE, 4-BROMOCHLOROACETYL- |
| 39 | 1-AZASPIRO(4.5)DECANE, 1-BROMOCHLOROACETYL- |
| 40 | OXAZOLIDINE, 3-(DICHLOROACETYL)-2,2-DIMETHYL-5-(2-THIENYL)- |
| 41 | ACETAMIDE, 2,2-DIBROMO-N,N-DI-2-PROPENYL- |
| 42 | ACETAMIDE, N,N-BIS[(3-BUTYNYLOXY)-METHYL]-2,2-DICHLORO- |
| 43 | ACETAMIDE, N,N-BIS[(3-PENTYNYLOXY)-METHYL]-2-CHLORO- |
| 44 | ACETAMIDE, 2,2-DICHLORO-N,N-BIS[(3-PENTYNYLOXY)METHYL]- |
| 45 | ETHANONE, 2,2-DICHLORO-1-(1,2,3,4-TETRAHYDRO-1-METHYL-2-ISOQUINOLINYL)- |
| 46 | 1,3-DIOXOLANE, 2-(DICHLOROMETHYL)-2-METHYL- |
| 47 | ISOQUINOLINE, 2-(DICHLOROACETYL)-1,2,3,4-TETRAHYDRO-1-PROPYL- |
| 48 | 1H-ISOINDOLE, 2-(DICHLOROACETYL)-2,3-DIHYDRO- |
| 49 | ISOQUINOLINE, 2-(DICHLOROACETYL)-1,2,3,4-TETRAHYDRO-1-(1-METHYLETHYL)- |
| 50 | ACETAMIDE, 2-CHLORO-N-[1-(2,4,6-TRIMETHYLPHENYL)ETHENYL]- |
| 51 | ACETAMIDE, 2,2-DICHLORO-N-[1-(2,4,6-TRIMETHYLPHENYL)ETHENYL]- |
| 52 | ACETAMIDE, 2,2-DICHLORO-N-ETHYL-N-(METHOXYMETHYL)- |
| 53 | ACETAMIDE, 2,2-DICHLORO-N-2-PROPENYL-N-[3-(TRIFLUOROMETHYL)PHENYL]- |
| 54 | ACETAMIDE, N,N'-1,2-ETHANEDIYLBIS[2,2-DICHLORO-N-(2-METHYL-1-PROPENYL)]- |
| 55 | 5-DICHLOROACETYL-3,3,6-TRIMETHYL-9-OXO-1,5-DIAZABICYCLO[4.3.0]NONANE |
| 56 | QUINOXALINE, 1,4-BIS(DICHLOROACETYL)-1,2,3,4-TETRAHYDRO- |
| 57 | 1H-1,4-DIAZONINE, 1,4-BIS(DICHLOROACETYL)OCTAHYDRO- |
| 58 | 1H-1,5-DIAZONINE, 1,5-BIS(BROMOCHLOROACETYL)OCTAHYDRO- |
| 59 | 1H-1,5-DIAZONINE, 1,5-BIS(DIBROMOACETYL)OCTAHYDRO- |
| 60 | 1H-1,5-DIAZONINE, 1,5-BIS(DICHLOROACETYL)OCTAHYDRO-3-METHYL- |
| 61 | 1H-1,5-DIAZONINE, 1,5-BIS(DICHLOROACETYL)OCTAHYDRO-2-METHYL- |
| 62 | 7-AZASPIRO(4.5)DECANE, 7-(DICHLOROACETYL)-8,8-DIMETHYL- |
| 63 | QUINOXLAINE, 1,4-BIS(DICHLOROACETYL)-1,2,3,4-TETRAHYDRO-2-METHYL- |
| 64 | ISOQUINOLINE, 2-(DICHLOROACETYL)-1,2,3,4-TETRAHYDRO-1-(TRIFLUOROMETHYL)- |
| 65 | ACETAMIDE, 2,2-DICHLORO-N-ETHYL-N-(2-PHENYLETHYL)- |
| 66 | ACETAMIDE, 2,2-DICHLORO-N-(ETHOXYMETHYL)-N-(2-PHENYLETHYL)- |
| 67 | ISOQUINOLINE, 2-(DICHLOROACETYL)-1,2,3,4-TETRAHYDRO-1,3-DIMETHYL- |
| 68 | ISOQUINOLINE, 2-(DICHLOROACETYL)-1-ETHYL-1,2,3,4-TETRAHYDRO-3-METHYL- |
| 69 | ISOQUINOLINE, 2-(DICHLOROACETYL)-1,2,3,4-TETRAHYDRO-1,7-DIMETHYL- |
| 70 | 1,5-DIAZOCINE, 1,5-BIS(DICHLOROACETYL)-OCTAHYDRO- |
| 71 | PIPERAZINE, 1,4-BIS(DICHLOROACETYL)-2-METHYL-5-(1-METHYLETHYL)-, (2S,5R-TRANS)- |
| 72 | PIPERAZINE, 1,4-[BIS(DICHLOROACETYL)]-2-PHENYL- |
| 73 | OXAZOLIDINE, 3-(DICHLOROACETYL)-5-(3-FURANYL)-2,2-DIMETHYL- |
| 74 | OXAZOLIDINE, 3-(DICHLOROACETYL)-5-(2-FURANYL)-2,2-DIMETHYL- |
| 75 | PYRIDINE, 3-[3-(DICHLOROACETYL)-2,2-DIMETHYL-5-OXAZOLIDINYL]- |
| 76 | PROPANAMIDE, N-[5-BROMO-4-(2,2,3,3,3-PENTAFLUOROETHYL)-2-THIAZOLYL]-2,2-DICHLORO- |
| 77 | PROPANENITRILE, 2-{[4-(1,1-DIMETHYLETHYL)PHENYL]THIO}- |
| 78 | 4-(DICHLOROACETYL)-3,4-DIHYDRO-3-METHYL-2H-1,4-BENZOXAZINE |

In Table V the herbicide dicamba was used for evaluating the relative antidotal properties of the above-listed compounds. The symbols in this table have the following meanings:

W = % Plant Inhibition caused by combination of herbicide and antidote.

WO = % Plant Inhibition caused by herbicide alone.

Data reported in parentheses = % Safening Effect.

$$(-) = \frac{WO - W}{WO} \times 100$$

As in the preceding (and all tables herein) application rates are given in kilograms per hectare (kg/ha).

Commercially-available or in-house formulations of the herbicides used in Examples 10–15 and Tables V–X had the following compositions (in weight percent):

| Herbicide | Active Ingredient | Inerts |
|---|---|---|
| Dicamba | 60.2 | 39.8 |
| Acetochlor | 87.3 | 12.7 |
| Alachlor | 45.1 | 54.9 |
| Metolachlor | 86.4 | 13.6 |

EXAMPLE 10

The following procedure shows interaction between a herbicide (dicamba in this example) and antidote when the antidote is applied in a soil furrow containing crop seed and the herbicide is incorporated in a soil cover layer. Containers were filled and compacted with fumigated silt loam soil to a depth of 1.3 cm from the top of the container. A first container was designated as an untreated control, a second container was designated as a herbicide control, and a third container was designated as a herbicide+antidote test container. Each container was seeded with crop seed in marked furrows. Antidote compound, dissolved in acetone, was applied directly to the seeded furrows of the third container. Antidote application rate was 0.55 mg active compound per inch of furrow (0.22 mg/cm). This rate was comparable to a plot application rate of 0.28 kilogram per hectare (kg/ha), based on 76 cm (30") spaced-apart furrows. Then, each of the second and third containers was filled and leveled with a cover layer of soil having incorporated therein the selected herbicide at a predetermined concentration. The first container was filled and leveled with soil containing no herbicide. Pots were overhead irrigated with 0.6 cm ($\frac{1}{4}$"), then placed on a bench in a greenhouse and sub-irrigated as required for the duration of the test. Plant response was observed about three weeks after initial treatment. Results are reported in Table V.

TABLE V

| | | | | CORN | | VELVET-LEAF | |
|---|---|---|---|---|---|---|---|
| | | ANTIDOTE | | | | | |
| HERBICIDE | RATE | NO | RATE | W | WO | W | WO |
| DICAMBA | 1.12 | 1 | 0.28 | 5 | 23 | 100 | 99 |
| | | | | (79) | | | |
| DICAMBA | 1.12 | 2 | 0.28 | 10 | 13 | 98 | 99 |
| | | | | (57) | | (2) | |
| DICAMBA | 1.12 | 3 | 0.28 | 0 | 23 | 98 | 99 |
| | | | | (100) | | (2) | |
| DICAMBA | 1.12 | 4 | 0.28 | 10 | 23 | 100 | 99 |
| | | | | (57) | | | |
| DICAMBA | 1.12 | 5 | 0.28 | 10 | 23 | 98 | 99 |
| | | | | (57) | | (2) | |
| DICAMBA | 1.12 | 6 | 0.28 | 15 | 23 | 95 | 99 |
| | | | | (35) | | (5) | |
| DICAMBA | 1.12 | 7 | 0.28 | 20 | 23 | 90 | 99 |
| | | | | (14) | | (10) | |
| DICAMBA | 1.12 | 8 | 0.28 | 10 | 23 | 100 | 99 |
| | | | | (57) | | | |
| DICAMBA | 1.12 | 9 | 0.28 | 10 | 23 | 85 | 99 |
| | | | | (57) | | (15) | |
| DICAMBA | 1.12 | 10 | 0.28 | 10 | 23 | 95 | 99 |
| | | | | (57) | | (5) | |
| DICAMBA | 1.12 | 11 | 0.28 | 5 | 23 | 90 | 99 |
| | | | | (79) | | (10) | |
| DICAMBA | 1.12 | 12 | 0.28 | 15 | 23 | 100 | 99 |
| | | | | (35) | | | |
| DICAMBA | 1.12 | 13 | 0.28 | 10 | 23 | 100 | 99 |
| | | | | (57) | | | |
| DICAMBA | 1.12 | 14 | 0.28 | 10 | 23 | 100 | 99 |
| | | | | (57) | | | |
| DICAMBA | 1.12 | 15 | 0.28 | 15 | 23 | 100 | 99 |
| | | | | (35) | | | |
| DICAMBA | 1.12 | 16 | 0.28 | 20 | 23 | 90 | 99 |
| | | | | (14) | | (10) | |
| DICAMBA | 1.12 | 17 | 0.28 | 20 | 23 | 85 | 99 |
| | | | | (14) | | (15) | |
| DICAMBA | 1.12 | 18 | 0.28 | 10 | 23 | 100 | 99 |
| | | | | (57) | | | |
| DICAMBA | 1.12 | 19 | 0.28 | 10 | 23 | 100 | 99 |
| | | | | (57) | | | |
| DICAMBA | 1.12 | 20 | 0.28 | 15 | 23 | 100 | 99 |
| | | | | (35) | | | |
| DICAMBA | 1.12 | 21 | 0.28 | 10 | 23 | 95 | 99 |
| | | | | (57) | | (5) | |
| DICAMBA | 1.12 | 22 | 0.28 | 0 | 23 | 100 | 99 |
| | | | | (100) | | | |
| DICAMBA | 1.12 | 23 | 0.28 | 20 | 23 | 100 | 99 |
| | | | | (14) | | | |
| DICAMBA | 1.12 | 24 | 0.28 | 20 | 23 | 100 | 99 |
| | | | | (14) | | | |
| DICAMBA | 1.12 | 25 | 0.28 | 10 | 23 | 65 | 99 |
| | | | | (57) | | (35) | |
| DICAMBA | 1.12 | 26 | 0.28 | 5 | 23 | 100 | 99 |
| | | | | (79) | | | |
| DICAMBA | 1.12 | 27 | 0.28 | 10 | 23 | 80 | 99 |
| | | | | (57) | | (20) | |
| DICAMBA | 1.12 | 28 | 0.28 | 15 | 23 | 90 | 99 |
| | | | | (35) | | (10) | |
| DICAMBA | 1.12 | 29 | 0.28 | 10 | 23 | 100 | 99 |
| | | | | (57) | | | |
| DICAMBA | 1.12 | 30 | 0.28 | 10 | 23 | 100 | 99 |
| | | | | (57) | | | |
| DICAMBA | 1.12 | 31 | 0.28 | 10 | 23 | 95 | 99 |
| | | | | (57) | | (5) | |
| DICAMBA | 1.12 | 32 | 0.28 | 20 | 23 | 100 | 99 |
| | | | | (14) | | | |
| DICAMBA | 1.12 | 33 | 0.28 | 20 | 23 | 95 | 99 |
| | | | | (14) | | (5) | |
| DICAMBA | 1.12 | 34 | 0.28 | 20 | 23 | 100 | 99 |
| | | | | (14) | | | |
| DICAMBA | 1.12 | 35 | 0.28 | 50 | 23 | 100 | 99 |
| DICAMBA | 1.12 | 36 | 0.28 | 10 | 23 | 100 | 99 |
| | | | | (57) | | | |
| DICAMBA | 1.12 | 37 | 0.28 | 15 | 23 | 100 | 99 |
| | | | | (35) | | | |
| DICAMBA | 1.12 | 38 | 0.28 | 10 | 23 | 100 | 99 |
| | | | | (57) | | | |
| DICAMBA | 1.12 | 39 | 0.28 | 10 | 23 | 95 | 99 |
| | | | | (57) | | (5) | |
| DICAMBA | 1.12 | 40 | 0.28 | 10 | 23 | 100 | 99 |
| | | | | (57) | | | |
| DICAMBA | 1.12 | 41 | 0.28 | 10 | 23 | 95 | 99 |
| | | | | (57) | | (5) | |
| DICAMBA | 1.12 | 42 | 0.28 | 25 | 23 | 100 | 99 |
| DICAMBA | 1.12 | 43 | 0.28 | 20 | 23 | 100 | 99 |
| | | | | (14) | | | |
| DICAMBA | 1.12 | 44 | 0.28 | 10 | 23 | 90 | 99 |
| | | | | (57) | | (10) | |
| DICAMBA | 1.12 | 45 | 0.28 | 40 | 23 | 100 | 99 |
| DICAMBA | 1.12 | 46 | 0.28 | 10 | 23 | 90 | 99 |
| | | | | (57) | | (10) | |
| DICAMBA | 1.12 | 47 | 0.28 | 20 | 23 | 100 | 99 |
| | | | | (14) | | | |
| DICAMBA | 1.12 | 48 | 0.28 | 15 | 23 | 100 | 99 |
| | | | | (35) | | | |
| DICAMBA | 1.12 | 49 | 0.28 | 15 | 23 | 100 | 99 |
| | | | | (35) | | | |
| DICAMBA | 1.12 | 50 | 0.28 | 15 | 23 | 100 | 99 |
| | | | | (35) | | | |
| DICAMBA | 1.12 | 51 | 0.28 | 5 | 23 | 95 | 99 |
| | | | | (79) | | (5) | |
| DICAMBA | 1.12 | 52 | 0.28 | 15 | 23 | 100 | 99 |
| | | | | (35) | | | |
| DICAMBA | 1.12 | 53 | 0.28 | 15 | 23 | 100 | 99 |
| | | | | (35) | | | |
| DICAMBA | 1.12 | 54 | 0.28 | 25 | 23 | 100 | 99 |
| DICAMBA | 1.12 | 55 | 0.28 | 20 | 23 | 60 | 99 |
| | | | | (14) | | (40) | |
| DICAMBA | 1.12 | 56 | 0.28 | 15 | 23 | 70 | 99 |
| | | | | (35) | | (30) | |
| DICAMBA | 1.12 | 57 | 0.28 | 10 | 23 | 100 | 99 |
| | | | | (57) | | | |
| DICAMBA | 1.12 | 58 | 0.28 | 10 | 23 | 95 | 99 |
| | | | | (57) | | (5) | |
| DICAMBA | 1.12 | 59 | 0.28 | 5 | 23 | 95 | 99 |
| | | | | (79) | | (5) | |
| DICAMBA | 1.12 | 60 | 0.28 | 10 | 23 | 100 | 99 |
| | | | | (57) | | | |
| DICAMBA | 1.12 | 61 | 0.28 | 15 | 23 | 100 | 99 |
| | | | | (35) | | | |
| DICAMBA | 1.12 | 62 | 0.28 | 15 | 23 | 100 | 99 |
| | | | | (35) | | | |
| DICAMBA | 1.12 | 63 | 0.28 | 10 | 23 | 80 | 99 |
| | | | | (57) | | (20) | |
| DICAMBA | 1.12 | 64 | 0.28 | 10 | 23 | 90 | 99 |
| | | | | (57) | | (10) | |
| DICAMBA | 1.12 | 65 | 0.28 | 10 | 23 | 85 | 99 |
| | | | | (57) | | (15) | |
| DICAMBA | 1.12 | 66 | 0.28 | 15 | 23 | 95 | 99 |
| | | | | (35) | | (5) | |
| DICAMBA | 1.12 | 67 | 0.28 | 5 | 23 | 95 | 99 |
| | | | | (79) | | (5) | |
| DICAMBA | 1.12 | 68 | 0.28 | 10 | 23 | 90 | 99 |
| | | | | (57) | | (10) | |

TABLE V-continued

% PLANT INHIBITION

| HERBICIDE | RATE | ANTIDOTE NO | RATE | SORGHUM (GRAIN) W | WO | VELVET-LEAF W | WO |
|---|---|---|---|---|---|---|---|
| DICAMBA | 1.12 | 69 | 0.28 | 5 | 23 (79) | 90 | 99 (10) |
| DICAMBA | 1.12 | 70 | 0.28 | 10 | 23 (57) | 100 | 99 |
| DICAMBA | 1.12 | 71 | 0.28 | 10 | 23 (57) | 90 | 99 (10) |
| DICAMBA | 1.12 | 72 | 0.28 | 5 | 23 (79) | 70 | 99 (30) |
| DICAMBA | 1.12 | 73 | 0.28 | 5 | 23 (79) | 80 | 99 (20) |
| DICAMBA | 0.56 | 7 | 0.56 | 35 | 30 | 100 | 80 |
| DICAMBA | 2.24 | 7 | 0.56 | 85 | 95 (11) | 95 | 100 (5) |
| DICAMBA | 0.56 | 7 | 2.24 | 10 | 30 (67) | 100 | 80 |
| DICAMBA | 2.24 | 7 | 2.24 | 85 | 95 (11) | 60 | 100 (40) |
| DICAMBA | 0.56 | 7 | 8.96 | 15 | 30 (50) | 95 | 80 |
| DICAMBA | 2.24 | 7 | 8.96 | 90 | 95 (6) | 100 | 100 (0) |
| DICAMBA | 0.56 | 8 | 0.56 | 15 | 30 (50) | 95 | 80 |
| DICAMBA | 2.24 | 8 | 0.56 | 45 | 95 (53) | 100 | 100 (0) |
| DICAMBA | 0.56 | 8 | 2.24 | 20 | 30 (34) | 35 | 80 (57) |
| DICAMBA | 2.24 | 8 | 2.24 | 90 | 95 (6) | 45 | 100 (55) |
| DICAMBA | 0.56 | 8 | 8.96 | 10 | 30 (67) | 95 | 80 |
| DICAMBA | 2.24 | 8 | 8.96 | 95 | 95 (0) | 100 | 100 (0) |
| DICAMBA | 0.56 | 9 | 0.56 | 20 | 30 (34) | 100 | 80 |
| DICAMBA | 2.24 | 9 | 0.56 | 85 | 95 (11) | 100 | 100 (0) |
| DICAMBA | 0.56 | 9 | 2.24 | 10 | 30 (67) | 90 | 80 |
| DICAMBA | 2.24 | 9 | 2.24 | 25 | 95 (74) | 100 | 100 (0) |
| DICAMBA | 0.56 | 9 | 8.96 | 0 | 30 (100) | 70 | 80 (13) |
| DICAMBA | 2.24 | 9 | 8.96 | 10 | 95 (90) | 100 | 100 (0) |
| DICAMBA | 0.56 | 11 | 0.56 | 10 | 30 (67) | 90 | 80 |
| DICAMBA | 2.24 | 11 | 0.56 | 80 | 95 (16) | 100 | 100 (0) |
| DICAMBA | 0.56 | 11 | 2.24 | 5 | 30 (84) | 100 | 80 |
| DICAMBA | 2.24 | 11 | 2.24 | 75 | 95 (22) | 95 | 100 (5) |
| DICAMBA | 0.56 | 11 | 8.96 | 5 | 30 (84) | 10 | 80 (88) |
| DICAMBA | 2.24 | 11 | 8.96 | 45 | 95 (53) | 100 | 100 (0) |
| DICAMBA | 0.56 | 12 | 0.56 | 10 | 30 (67) | 100 | 80 |
| DICAMBA | 2.24 | 12 | 0.56 | 85 | 95 (11) | 100 | 100 (0) |
| DICAMBA | 0.56 | 12 | 2.24 | 20 | 30 (34) | 55 | 80 (32) |
| DICAMBA | 2.24 | 12 | 2.24 | 85 | 95 (11) | 100 | 100 (0) |
| DICAMBA | 0.56 | 12 | 8.96 | 25 | 30 (17) | 100 | 80 |
| DICAMBA | 2.24 | 12 | 8.96 | 80 | 95 (16) | 100 | 100 (0) |
| DICAMBA | 0.56 | 13 | 0.56 | 10 | 30 (67) | 100 | 80 |
| DICAMBA | 2.24 | 13 | 0.56 | 80 | 95 (16) | 95 | 100 (5) |
| DICAMBA | 0.56 | 13 | 2.24 | 30 | 30 (0) | 95 | 80 |
| DICAMBA | 2.24 | 13 | 2.24 | 80 | 95 (16) | 100 | 100 (0) |
| DICAMBA | 0.56 | 13 | 8.96 | 5 | 30 (84) | 90 | 80 |
| DICAMBA | 2.24 | 13 | 8.96 | 25 | 95 (74) | 100 | 100 (0) |
| DICAMBA | 0.56 | 17 | 0.56 | 15 | 30 (50) | 50 | 80 (38) |
| DICAMBA | 1.13 | 17 | 0.56 | 75 | 95 (22) | 100 | 100 (0) |
| DICAMBA | 0.56 | 17 | 2.24 | 10 | 30 (67) | 80 | 80 (0) |
| DICAMBA | 2.24 | 17 | 2.24 | 50 | 95 (48) | 100 | 100 (0) |
| DICAMBA | 0.56 | 17 | 8.96 | 25 | 30 (17) | 90 | 80 |
| DICAMBA | 2.24 | 17 | 8.96 | 85 | 95 (11) | 100 | 100 (0) |
| DICAMBA | 0.56 | 25 | 0.56 | 30 | 30 (0) | 75 | 80 (7) |
| DICAMBA | 2.24 | 25 | 0.56 | 90 | 95 (6) | 100 | 100 (0) |
| DICAMBA | 0.56 | 25 | 2.24 | 60 | 30 | 100 | 80 |
| DICAMBA | 2.24 | 25 | 2.24 | 40 | 95 (58) | 100 | 100 (0) |
| DICAMBA | 2.24 | 25 | 8.96 | 0 | 30 (100) | 80 | 80 (0) |
| DICAMBA | 2.24 | 25 | 8.96 | 80 | 95 (16) | 100 | 100 (0) |
| DICAMBA | 0.56 | 29 | 0.56 | 0 | 30 (100) | 70 | 80 (13) |
| DICAMBA | 2.24 | 29 | 0.56 | 65 | 95 (32) | 100 | 100 (0) |
| DICAMBA | 0.56 | 29 | 2.24 | 35 | 30 | 100 | 80 |
| DICAMBA | 2.24 | 29 | 2.24 | 80 | 95 (16) | 100 | 100 (0) |
| DICAMBA | 0.56 | 29 | 8.96 | 5 | 30 (84) | 90 | 80 |
| DICAMBA | 2.24 | 29 | 8.96 | 85 | 95 (11) | 90 | 100 (10) |
| DICAMBA | 0.56 | 32 | 0.56 | 0 | 30 (100) | 55 | 80 (32) |
| DICAMBA | 2.24 | 32 | 0.56 | 75 | 95 (22) | 100 | 100 (0) |
| DICAMBA | 0.56 | 32 | 2.24 | 20 | 30 (34) | 70 | 80 (13) |
| DICAMBA | 2.24 | 32 | 2.24 | 45 | 95 (53) | 100 | 100 (0) |
| DICAMBA | 0.56 | 32 | 8.96 | 0 | 30 (100) | 55 | 80 (32) |
| DICAMBA | 2.24 | 32 | 8.96 | 30 | 95 (69) | 50 | 100 (50) |
| DICAMBA | 0.56 | 33 | 0.56 | 40 | 30 | 60 | 80 (25) |
| DICAMBA | 2.24 | 33 | 0.56 | 80 | 95 (16) | 100 | 100 (0) |
| DICAMBA | 0.56 | 33 | 2.24 | 30 | 30 (0) | 10 | 80 (88) |
| DICAMBA | 2.24 | 33 | 2.24 | 80 | 95 (16) | 95 | 100 (5) |
| DICAMBA | 0.56 | 33 | 8.96 | 25 | 30 (17) | 40 | 80 (50) |
| DICAMBA | 2.24 | 33 | 8.96 | 70 | 95 (27) | 100 | 100 (0) |
| DICAMBA | 0.56 | 38 | 0.56 | 80 | 30 | 70 | 80 (13) |
| DICAMBA | 2.24 | 38 | 0.56 | 60 | 95 (37) | 100 | 100 (0) |
| DICAMBA | 0.56 | 38 | 2.24 | 15 | 30 (50) | 95 | 80 |
| DICAMBA | 2.24 | 38 | 2.24 | 60 | 95 (37) | 100 | 100 (0) |
| DICAMBA | 0.56 | 38 | 8.96 | 15 | 30 (50) | 20 | 80 (75) |
| DICAMBA | 2.24 | 38 | 8.96 | 40 | 95 (58) | 100 | 100 (0) |
| DICAMBA | 0.56 | 45 | 0.56 | 40 | 30 | 70 | 80 (13) |
| DICAMBA | 2.24 | 45 | 0.56 | 95 | 95 (0) | 100 | 100 (0) |
| DICAMBA | 0.56 | 45 | 2.24 | 5 | 30 | 100 | 80 |

TABLE V-continued

% PLANT INHIBITION

| | | | | | | | |
|---|---|---|---|---|---|---|---|
| | | | | (84) | | (0) | |
| DICAMBA | 2.24 | 45 | 2.24 | 95 | 95 | 100 | 100 |
| | | | | (0) | | (0) | |
| DICAMBA | 0.56 | 45 | 8.96 | 5 | 30 | 95 | 80 |
| | | | | (84) | | (0) | |
| DICAMBA | 2.24 | 45 | 8.96 | 85 | 95 | 100 | 100 |
| | | | | (11) | | (0) | |
| DICAMBA | 0.56 | 52 | 0.56 | 0 | 30 | 100 | 80 |
| | | | | (100) | | (0) | |
| DICAMBA | 2.24 | 52 | 0.56 | 80 | 95 | 100 | 100 |
| | | | | (16) | | (0) | |
| DICAMBA | 0.56 | 52 | 2.24 | 30 | 30 | 90 | 80 |
| | | | | (0) | | | |
| DICAMBA | 2.24 | 52 | 2.24 | 45 | 95 | 100 | 100 |
| | | | | (53) | | (0) | |
| DICAMBA | 0.56 | 52 | 8.96 | 20 | 30 | 100 | 80 |
| | | | | (34) | | | |
| DICAMBA | 2.24 | 52 | 8.96 | 85 | 95 | 100 | 100 |
| | | | | (11) | | (0) | |
| DICAMBA | 0.56 | 54 | 0.56 | 30 | 30 | 90 | 80 |
| | | | | (0) | | | |
| DICAMBA | 2.24 | 54 | 0.56 | 65 | 95 | 100 | 100 |
| | | | | (32) | | (0) | |
| DICAMBA | 0.56 | 54 | 2.24 | 0 | 30 | 100 | 80 |
| | | | | (100) | | | |
| DICAMBA | 2.24 | 54 | 2.24 | 80 | 95 | 100 | 100 |
| | | | | (16) | | (0) | |
| DICAMBA | 0.56 | 54 | 8.96 | 30 | 30 | 10 | 80 |
| | | | | (0) | | (88) | |
| DICAMBA | 2.24 | 54 | 8.96 | 70 | 95 | 100 | 100 |
| | | | | (27) | | (0) | |
| DICAMBA | 0.56 | 56 | 0.56 | 50 | 30 | 100 | 80 |
| DICAMBA | 2.24 | 56 | 0.56 | 90 | 95 | 100 | 100 |
| | | | | (6) | | (0) | |
| DICAMBA | 0.56 | 56 | 2.24 | 20 | 30 | 90 | 80 |
| | | | | (34) | | | |
| DICAMBA | 2.24 | 56 | 2.24 | 75 | 95 | 100 | 100 |
| | | | | (22) | | (0) | |
| DICAMBA | 0.56 | 56 | 8.96 | 5 | 30 | 80 | 80 |
| | | | | (84) | | (0) | |
| DICAMBA | 2.24 | 56 | 8.96 | 85 | 95 | 100 | 100 |
| | | | | (11) | | (0) | |
| DICAMBA | 0.56 | 58 | 0.56 | 20 | 30 | 90 | 80 |
| | | | | (34) | | | |
| DICAMBA | 2.24 | 58 | 0.56 | 85 | 95 | 100 | 100 |
| | | | | (11) | | (0) | |
| DICAMBA | 0.56 | 58 | 2.24 | 55 | 30 | 100 | 80 |
| DICAMBA | 2.24 | 58 | 2.24 | 95 | 95 | 100 | 100 |
| | | | | (0) | | (0) | |
| DICAMBA | 0.56 | 58 | 8.96 | 30 | 30 | 50 | 80 |
| | | | | (0) | | (38) | |
| DICAMBA | 2.24 | 58 | 8.96 | 75 | 95 | 100 | 100 |
| | | | | (22) | | (0) | |
| DICAMBA | 0.56 | 61 | 0.56 | 10 | 30 | 15 | 80 |
| | | | | (67) | | (82) | |
| DICAMBA | 2.24 | 61 | 0.56 | 85 | 95 | 100 | 100 |
| | | | | (11) | | (0) | |
| DICAMBA | 0.56 | 61 | 2.24 | 50 | 30 | 100 | 80 |
| DICAMBA | 2.24 | 61 | 2.24 | 75 | 95 | 100 | 100 |
| | | | | (22) | | (0) | |
| DICAMBA | 0.56 | 61 | 8.96 | 30 | 30 | 100 | 80 |
| | | | | (0) | | | |
| DICAMBA | 2.24 | 61 | 8.96 | 55 | 95 | 100 | 100 |
| | | | | (43) | | (0) | |
| DICAMBA | 0.56 | 67 | 0.56 | 10 | 30 | 95 | 80 |
| | | | | (67) | | | |
| DICAMBA | 2.24 | 67 | 0.56 | 85 | 95 | 100 | 100 |
| | | | | (11) | | (0) | |
| DICAMBA | 0.56 | 67 | 2.24 | 25 | 30 | 100 | 80 |
| | | | | (17) | | | |
| DICAMBA | 2.24 | 67 | 2.24 | 90 | 95 | 100 | 100 |
| | | | | (6) | | (0) | |
| DICAMBA | 0.56 | 67 | 8.96 | 25 | 30 | 100 | 80 |
| | | | | (17) | | | |
| DICAMBA | 2.24 | 67 | 8.96 | 95 | 95 | 100 | 100 |
| | | | | (0) | | (0) | |
| DICAMBA | 0.56 | 70 | 0.56 | 55 | 30 | 95 | 80 |
| DICAMBA | 2.24 | 70 | 0.56 | 80 | 95 | 100 | 100 |
| | | | | (16) | | (0) | |
| DICAMBA | 0.56 | 70 | 2.24 | 40 | 30 | 95 | 80 |
| DICAMBA | 2.24 | 70 | 2.24 | 95 | 95 | 100 | 100 |
| | | | | (0) | | (0) | |
| DICAMBA | 0.56 | 70 | 8.96 | 10 | 30 | 95 | 80 |
| | | | | (67) | | | |
| DICAMBA | 2.24 | 70 | 8.96 | 80 | 95 | 100 | 100 |
| | | | | (16) | | (0) | |
| DICAMBA | 0.56 | 71 | 0.56 | 5 | 30 | 75 | 80 |
| | | | | (84) | | (7) | |
| DICAMBA | 2.24 | 71 | 0.56 | 80 | 95 | 100 | 100 |
| | | | | (16) | | (0) | |
| DICAMBA | 0.56 | 71 | 2.24 | 10 | 30 | 100 | 80 |
| | | | | (67) | | | |
| DICAMBA | 2.24 | 71 | 2.24 | 80 | 95 | 100 | 100 |
| | | | | (16) | | (0) | |
| DICAMBA | 0.56 | 71 | 8.96 | 25 | 30 | 95 | 80 |
| | | | | (17) | | | |
| DICAMBA | 2.24 | 71 | 8.96 | 100 | 95 | 100 | 100 |
| | | | | | | (0) | |
| DICAMBA | 0.56 | 74 | 0.56 | 15 | 30 | 95 | 80 |
| | | | | (50) | | | |
| DICAMBA | 2.24 | 74 | 0.56 | 75 | 95 | 100 | 100 |
| | | | | (22) | | (0) | |
| DICAMBA | 0.56 | 74 | 2.24 | 25 | 30 | 95 | 80 |
| | | | | (17) | | | |
| DICAMBA | 2.24 | 74 | 2.24 | 90 | 95 | 100 | 100 |
| | | | | (6) | | (0) | |
| DICAMBA | 0.56 | 74 | 8.96 | 0 | 30 | 20 | 80 |
| | | | | (100) | | (75) | |
| DICAMBA | 2.24 | 74 | 8.96 | 45 | 95 | 100 | 100 |
| | | | | (53) | | (0) | |
| DICAMBA | 0.56 | 73 | 0.56 | 30 | 30 | 40 | 80 |
| | | | | (0) | | (50) | |
| DICAMBA | 2.24 | 73 | 0.56 | 90 | 95 | 100 | 100 |
| | | | | (6) | | (0) | |
| DICAMBA | 0.56 | 73 | 2.24 | 15 | 30 | 100 | 80 |
| | | | | (50) | | | |
| DICAMBA | 2.24 | 73 | 2.24 | 80 | 95 | 100 | 100 |
| | | | | (16) | | (0) | |
| DICAMBA | 0.56 | 73 | 8.96 | 0 | 30 | 90 | 80 |
| | | | | (100) | | | |
| DICAMBA | 2.24 | 73 | 8.96 | 85 | 95 | 100 | 100 |
| | | | | (11) | | (0) | |

EXAMPLE 11

The following procedure shows interaction between herbicide and antidote when both are incorporated in a soil cover layer before emergence of crop and weed species. Containers were filled and compacted with a fumigated silt loam top soil to a depth of about 1.3 cm from the top of the container. A first container was designated as an untreated control, a second container was designated as a herbicide control, and a third container was designated as a herbicide + antidote test container. Each of the containers was seeded with a crop species. A measured amount of each herbicide dispersed or dissolved in acetone or water was applied to a measured quantity of soil. To this same quantity of soil treated with herbicide, there was added a measured amount of antidote dispersed or dissolved in acetone or water. The quantity of soil treated with the herbicide and antidote was thoroughly mixed to incorporate the herbicide and antidote in the soil uniformly. The seed bed in the third container of soil was covered with the soil treated with the herbicide and antidote and the container was leveled. For each test series, the seed beds of the first and second containers were likewise covered by soil layers. The cover layer of the first container was not treated with herbicide or antidote. The cover layer of the second container had a measured quantity of both herbicides alone incorporated therein. The containers were then placed on a bench in a greenhouse and sub-irrigated as required for the duration of the test. Plant response was observed about three weeks after initial treatment. Results are reported in Table VI, wherein the weeds in the test, velvetleaf and barnyardgrass have the symbols "VL" and "BYG", respectively.

TABLE VI

| Herbicide | | Antidote | | % Injury | | |
|---|---|---|---|---|---|---|
| Acetochlor Rate | Dicamba Rate | No. | Rate | Corn | VL | BYG |
| 4.48 | — | — | — | 32 | 7 | 100 |
| 8.96 | — | — | — | 68 | 43 | 100 |
| — | 1.12 | — | — | 28 | 97 | 95 |
| — | 2.24 | — | — | 48 | 98 | 100 |
| 4.48 | 1.12 | — | — | 75 | 98 | 100 |
| 4.48 | 2.24 | — | — | 90 | 100 | 100 |
| 8.96 | 1.12 | — | — | 87 | 98 | 100 |
| 8.96 | 2.24 | — | — | 95 | 100 | 100 |
| — | — | 8 | 8.96 | 10 | 50 | 90 |
| 4.48 | — | " | " | 5 | 10 | 100 |
| 4.48 | — | " | 2.24 | 20 | 30 | 100 |
| 8.96 | — | " | 8.96 | 5 | 90 | 100 |
| 8.96 | — | " | 2.24 | 15 | 90 | 100 |
| — | 1.12 | " | 8.96 | 0 | 85 | 95 |
| — | 1.12 | " | 2.24 | 20 | 100 | 90 |
| — | 2.24 | " | 8.96 | 5 | 90 | 95 |
| — | 2.24 | " | 2.24 | 0 | 100 | 100 |
| 4.48 | 1.12 | " | 8.96 | 30 | 100 | 100 |
| 4.48 | 2.24 | " | 8.96 | 60 | 95 | 100 |
| 8.96 | 1.12 | " | 8.96 | 50 | 100 | 100 |
| 8.96 | 2.24 | " | 8.96 | 85 | 100 | 100 |
| 4.48 | 1.12 | " | 2.24 | 55 | 100 | 100 |
| 4.48 | 2.24 | " | 2.24 | 75 | 100 | 100 |
| 8.96 | — | " | 2.24 | 75 | 100 | 100 |
| 8.96 | — | " | 2.24 | 85 | 100 | 100 |
| — | — | 32 | 8.96 | 0 | 0 | 85 |
| 4.48 | — | " | 8.96 | 10 | 10 | 100 |
| 4.48 | — | " | 2.24 | 0 | 10 | 100 |
| 8.96 | — | " | 8.96 | 0 | 15 | 100 |
| 8.96 | — | " | 2.24 | 0 | 30 | 100 |
| — | 1.12 | " | 8.96 | 0 | 90 | 95 |
| — | 1.12 | " | 2.24 | 0 | 100 | 100 |
| — | 2.24 | " | 8.96 | 20 | 100 | 95 |
| — | 2.24 | " | 2.24 | 15 | 100 | 95 |
| 4.48 | 1.12 | 32 | 8.96 | 25 | 100 | 100 |
| 4.48 | 2.24 | " | " | 80 | 100 | 100 |
| 8.96 | 1.12 | " | " | 65 | 100 | 100 |
| 8.96 | 2.24 | " | " | 80 | 95 | 100 |
| 4.48 | 1.12 | " | 2.24 | 45 | 100 | 100 |
| 4.48 | 2.24 | " | " | 45 | 100 | 100 |
| 8.96 | 1.12 | " | " | 50 | 100 | 100 |
| 8.96 | 2.24 | " | " | 45 | 100 | 100 |
| — | — | 45 | 8.96 | 0 | 0 | 95 |
| 4.48 | — | " | " | 5 | 10 | 100 |
| 4.48 | — | " | 2.24 | 0 | 85 | 100 |
| 8.96 | — | " | 8.96 | 25 | 90 | 100 |
| 8.96 | — | " | 2.24 | 25 | 95 | 100 |
| — | 1.12 | " | 8.96 | 5 | 100 | 90 |
| — | " | " | 2.24 | 10 | 100 | 100 |
| — | 2.24 | " | 8.96 | 30 | 100 | 95 |
| — | " | " | 2.24 | 25 | 100 | 90 |
| 4.48 | 1.12 | " | 8.96 | 60 | 95 | 100 |
| " | 2.24 | " | " | 55 | 100 | 100 |
| 8.96 | 1.12 | " | " | 60 | 95 | 100 |
| " | 2.24 | " | " | 75 | 100 | 100 |
| 4.48 | 1.12 | " | 2.24 | 55 | 100 | 100 |
| 4.48 | 2.24 | " | " | 60 | 100 | 100 |
| 8.96 | 1.12 | " | " | 50 | 100 | 100 |
| " | 2.24 | " | " | 50 | 100 | 100 |
| — | — | 67 | 8.96 | 0 | 10 | 85 |
| 4.48 | — | " | " | 20 | 25 | 100 |
| " | — | " | 2.24 | 0 | 35 | 100 |
| 8.96 | — | " | 8.96 | 50 | 95 | 100 |
| 8.96 | — | " | 2.24 | 45 | 80 | 100 |
| — | 1.12 | " | 8.96 | 10 | 100 | 90 |
| — | " | " | 2.24 | 25 | 100 | 95 |
| — | 2.24 | " | 8.96 | 30 | 85 | 90 |
| — | " | " | 2.24 | 60 | 100 | 80 |
| 4.48 | 1.12 | 67 | 8.96 | 60 | 100 | 100 |
| " | 2.24 | " | " | 75 | 100 | 100 |
| 8.96 | 1.12 | " | " | 30 | 100 | 100 |
| " | 2.24 | " | " | 90 | 100 | 100 |

TABLE VI-continued

| Herbicide | | Antidote | | % Injury | | |
|---|---|---|---|---|---|---|
| Acetochlor Rate | Dicamba Rate | No. | Rate | Corn | VL | BYG |
| 4.48 | 1.12 | " | 2.24 | 80 | 100 | 100 |
| " | 2.24 | " | " | 65 | 100 | 100 |
| 8.96 | 1.12 | " | " | 70 | 95 | 100 |
| " | 2.24 | " | " | 90 | 95 | 100 |
| — | — | 71 | 8.96 | 0 | 0 | 90 |
| 4.48 | — | " | " | 5 | 10 | 100 |
| " | — | " | 2.24 | 5 | 10 | 100 |
| 8.96 | — | " | 8.96 | 30 | 20 | 100 |
| " | — | " | 2.24 | 0 | 10 | 100 |
| — | 1.12 | " | 8.96 | 10 | 85 | 90 |
| — | 1.12 | " | 2.24 | 10 | 100 | 95 |
| — | 2.24 | " | 8.96 | 35 | 100 | 95 |
| — | " | " | 2.24 | 5 | 100 | 95 |
| 4.48 | 1.12 | " | 8.96 | 45 | 100 | 100 |
| " | 2.24 | " | " | 35 | 95 | 100 |
| 8.96 | 1.12 | " | " | 55 | 100 | 100 |
| " | 2.24 | " | " | 75 | 100 | 100 |
| 4.48 | 1.12 | " | 2.24 | 60 | 100 | 100 |
| " | 2.24 | " | " | 55 | 100 | 100 |
| 8.96 | 1.12 | " | " | 45 | 100 | 100 |
| " | 2.24 | " | " | 80 | 100 | 100 |
| — | — | 74 | 8.96 | 0 | 0 | 90 |
| 4.48 | — | " | " | 20 | 70 | 100 |
| " | — | " | 2.24 | 5 | 15 | 100 |
| 8.96 | — | " | 8.96 | 10 | 20 | 100 |
| " | — | " | 2.24 | 10 | 60 | 100 |
| — | 1.12 | " | 8.96 | 15 | 100 | 90 |
| — | " | " | 2.24 | 10 | 90 | 80 |
| — | 2.24 | " | 8.96 | 20 | 90 | 90 |
| — | " | " | 2.24 | 35 | 100 | 100 |
| 4.48 | 1.12 | " | 8.96 | 45 | 100 | 100 |
| " | 2.24 | " | " | 60 | 100 | 100 |
| 8.96 | 1.12 | " | " | 55 | 95 | 100 |
| " | 2.24 | " | " | 35 | 90 | 100 |
| 4.48 | 1.12 | " | 2.24 | 10 | 100 | 100 |
| " | 2.24 | " | " | 75 | 90 | 100 |
| 8.96 | 1.12 | " | " | 40 | 100 | 100 |
| " | 2.24 | " | " | 55 | 100 | 100 |

All test compounds exhibited activity for each of the herbicides alone and for mixtures of the two together. Antidote No. 74 was the most active compound overall, reducing injury to corn from 75% with the combination of 4.48 kg/ha of acetochlor and 1.12 kg/ha of dicamba without the antidote to 10% with 2.24 kg/ha with the antidote.

EXAMPLE 12

The test procedure described in Example 11 was used to determine the antidotal efficacy of several compounds as safeners for the herbicides alachlor, dicamba and mixtures thereof in grain sorghum ("GrSO"). The broadleaf weed velvetleaf ("VL") was the test weed. Test results are shown in Table VII. Percent inhibition values for the herbicides without an antidote are averages of three replications, while values shown with the antidote are from a single replicate.

TABLE VII

| Herbicide | | Antidote | | % Injury | |
|---|---|---|---|---|---|
| Alachlor Rate | Dicamba Rate | No. | Rate | GrSO | VL |
| 0.56 | — | — | — | 93 | 0 |
| 2.24 | — | — | — | 93 | 0 |
| — | 1.12 | — | — | 60 | 79 |
| 0.56 | " | — | — | 97 | 100 |
| 2.24 | " | — | — | 99 | 100 |
| — | — | 9 | 8.96 | 25 | 0 |
| 0.56 | — | " | 0.56 | 10 | 0 |
| " | — | " | 2.24 | 20 | 10 |
| " | — | " | 8.96 | 30 | 0 |
| 2.24 | — | " | 0.56 | 50 | 0 |

TABLE VII-continued

| Herbicide | | Antidote | | % Injury | |
|---|---|---|---|---|---|
| Alachlor Rate | Dicamba Rate | No. | Rate | GrSO | VL |
| " | — | " | 2.24 | 20 | 0 |
| " | — | " | 8.96 | 5 | 0 |
| — | 1.12 | " | 0.56 | 35 | 100 |
| — | " | " | 2.24 | 35 | 95 |
| — | " | " | 8.96 | 45 | 70 |
| 0.56 | " | " | 0.56 | 55 | 100 |
| " | " | " | 2.24 | 55 | 100 |
| " | " | " | 8.96 | 95 | 100 |
| 2.24 | " | " | 0.56 | 95 | 100 |
| " | " | " | 2.24 | 75 | 100 |
| " | " | " | 8.96 | 85 | 100 |
| — | — | 11 | " | 10 | 0 |
| 0.56 | — | " | 0.56 | 25 | 0 |
| " | — | " | 2.24 | 0 | 0 |
| " | — | " | 8.96 | 30 | 0 |
| 2.24 | — | " | 0.56 | 70 | 0 |
| " | — | " | 2.24 | 60 | 0 |
| " | — | " | 8.96 | 25 | 0 |
| — | 1.12 | " | 0.56 | 60 | 100 |
| — | " | " | 2.24 | 65 | 50 |
| — | " | " | 8.96 | 50 | 30 |
| 0.56 | " | " | 0.56 | 40 | 50 |
| " | " | " | 2.24 | 80 | 100 |
| " | " | " | 8.96 | 25 | 100 |
| 2.24 | 1.12 | 11 | 0.56 | 90 | 40 |
| " | " | " | 2.24 | 95 | 100 |
| " | " | " | 8.96 | 90 | 100 |
| — | — | 13 | " | 0 | 0 |
| 0.56 | — | " | 0.56 | 20 | 0 |
| " | — | " | 2.24 | 0 | 0 |
| " | — | " | 8.96 | 20 | 0 |
| 2.24 | — | " | 0.56 | 30 | 0 |
| " | — | " | 2.24 | 15 | 0 |
| " | — | " | 8.96 | 15 | 0 |
| — | 1.12 | " | 0.56 | 55 | 100 |
| — | " | " | 2.24 | 65 | 90 |
| — | " | " | 8.96 | 50 | 100 |
| 0.56 | " | " | 0.56 | 55 | 90 |
| " | " | " | 2.24 | 80 | 50 |
| " | " | " | 8.96 | 55 | 100 |
| 2.24 | " | " | 0.56 | 95 | 100 |
| " | " | " | 2.24 | 75 | 100 |
| " | " | " | 8.96 | 70 | 100 |
| — | — | 29 | " | 0 | 0 |
| 0.56 | — | " | 0.56 | 45 | 0 |
| " | — | " | 2.24 | 15 | 100 |
| " | — | " | 8.96 | 10 | 10 |
| 2.24 | — | " | 0.56 | 75 | 0 |
| " | — | " | 2.24 | 70 | 0 |
| " | — | " | 8.96 | 45 | 85 |
| — | 1.12 | " | 0.56 | 40 | 100 |
| — | " | " | 2.24 | 45 | 100 |
| — | " | " | 8.96 | 30 | 100 |
| 0.56 | " | " | 0.56 | 90 | 100 |
| " | " | " | 2.24 | 50 | 60 |
| " | " | " | 8.96 | 60 | 100 |
| 2.24 | " | " | 0.56 | 95 | 100 |
| " | " | " | 2.24 | 95 | 100 |
| 2.24 | 1.12 | 29 | 8.96 | 90 | 100 |
| " | — | 32 | " | 0 | 0 |
| 0.56 | — | " | 0.56 | 80 | 100 |
| " | — | " | 2.24 | 60 | 0 |
| " | — | " | 8.96 | 25 | 0 |
| 2.24 | — | " | 0.56 | 95 | 0 |
| " | — | " | 2.24 | 95 | 0 |
| " | — | " | 8.96 | 70 | 0 |
| — | 1.56 | " | 0.56 | 70 | 100 |
| — | " | " | 2.24 | 50 | 80 |
| — | " | " | 8.96 | 55 | 100 |
| 0.56 | " | " | 0.56 | 95 | 100 |
| " | " | " | 2.24 | 95 | 100 |
| " | " | " | 8.96 | 85 | 50 |
| 2.24 | 1.12 | " | 0.56 | 100 | 100 |
| " | " | " | 2.24 | 95 | 100 |
| " | " | " | 8.96 | 95 | 25 |
| — | — | 74 | " | 10 | 0 |
| 0.56 | — | " | 0.56 | 10 | 0 |
| " | — | " | 2.24 | 0 | 0 |
| " | — | " | 8.96 | 25 | 0 |
| 2.24 | — | " | 0.56 | 50 | 0 |
| " | — | " | 2.24 | 35 | 100 |
| " | — | " | 8.96 | 35 | 0 |
| — | 1.12 | " | 0.56 | 55 | 85 |
| — | " | " | 2.24 | 50 | 90 |
| — | " | " | 8.96 | 60 | 100 |
| 0.56 | " | " | 0.56 | 65 | 80 |
| " | " | " | 2.24 | 70 | 100 |
| " | " | " | 8.96 | 75 | 90 |
| 2.24 | " | " | 0.56 | 95 | 100 |
| " | " | " | 2.24 | 90 | 100 |
| " | " | " | 8.96 | 80 | 100 |

The above indicate that the safening effects of the antidotes against the herbicides alachlor, dicamba and mixtures thereof under the given test conditions is not altogether consistent at the rates used in the test using sorghum as the test crop, which is highly sensitive to those herbicides. Some antidotal improvement may be suggested for other test modes, e.g., by use of a different mode of antidote application, e.g., as a crop seed coating as exemplified in the following example.

EXAMPLE 13

The following procedure was used to determine the interaction between a herbicide and antidote when the herbicide is topically applied to the soil surface and the antidote is applied to crop seed. Crop plant seed may be treated with the antidote either by contacting the seed with antidote in powder form or by contacting the seed with a solution or suspension of antidote compound dissolved or suspended in a suitable solvent, typically methylene chloride or toluene. Relative amounts of antidote compound and seed are used to provide an antidote-on-seed concentration, on a percent weight/weight basis, typically within the range of about 0.03 to 0.13%. Containers were filled and compacted with fumigated silt loam type soil to a depth of about 1.3 cm from the top of the container. A first container was designated as an untreated control, a second container was designated as a herbicide control, and a third container was designated as a herbicide +antidote test container. Untreated crop seed was placed in the first an second containers. Antidote-treated crop seed was placed in the third container. Then, each of the second and third containers was filled and leveled with a cover layer of soil having incorporated therein the selected herbicide at a pre-determined concentration. The first container was filled and leveled with soil containing no herbicide. All containers were given about 0.6 cm of overhead water to simulate an activating rainfall. The containers were placed on a greenhouse bench and sub-irrigated as required for the duration of the test. Plant response was observed about three weeks after initial treatment.

In this example, Antidotes No. 9 (common name "flurazole") and No. 12 (common name "cyometrinil") were coated onto sorghum seed for testing with the herbicides alachlor, dicamba and mixtures thereof. Green foxtail (GrFt) was present as the test weed. Test results are shown in Table VIII. The percent injury values shown for the herbicide treatment only (no antidote) are averages of six replications for the sorghum and three replications for the weed, while the values for the antidote-containing formulations are averages of four replicates for sorghum and two replicates for the weed.

TABLE VIII

| Antidote No. | Herbicide Alachlor Rate | Herbicide Dicamba Rate | % Injury GrSO | % Injury GrFt |
|---|---|---|---|---|
| Check | — | — | — | — |
| — | 0.56 | — | 63 | 100 |
| — | — | 1.12 | 14 | 6 |
| — | — | 0.56 | 20 | 16 |
| — | 0.56 | 1.12 | 89 | 100 |
| — | " | 0.56 | 54 | 100 |
| 9 | — | — | 7 | 0 |
| " | 0.56 | — | 10 | 100 |
| " | — | 0.56 | 0 | 8 |
| " | — | 1.12 | 20 | 72 |
| " | 0.56 | 0.56 | 17 | 100 |
| " | " | 1.12 | 12 | 100 |
| 12 | — | — | 10 | 0 |
| " | 0.56 | — | 4 | 100 |
| " | — | 0.56 | 7 | 20 |
| " | — | 1.12 | 17 | 65 |
| " | 0.56 | 0.56 | 33 | 100 |
| " | 0.56 | 1.12 | 15 | 98 |

The data in Table VIII show the reduced sorghum injury when the antidotes are applied as a seed dressing on the sorghum seed. These data may be contrasted with that in Table VII showing a generally less consistent safening effect when the herbicides and antidote are applied by soil incorporation in a cover layer. The data in Table VIII illustrate the efficacious safening of sorghum against alachlor and dicamba when the herbicides are applied separately or in combination to the sorghum seed coated with the antidotes.

EXAMPLE 14

This test was conducted to evaluate the antidotal (safening) effect of a number of antidotes against dicamba, metolachlor and combinations thereof in corn in the presence of the weeds velvetleaf (VL) and barnyardgrass (BYG).

The test procedure here was the same as that described in Examples 11 and 12. The concentration of the herbicidally active ingredients is shown earlier herein. Percent injury values to the plants treated with herbicide formulations containing no antidote represent averages of three replications, while percent injuries resulting from antidote-containing formulations are based on one replicate. Test results are shown in Table IX.

TABLE IX

| Herbicide Metolachlor Rate | Herbicide Dicamba Rate | Antidote No. | Antidote Rate | % Injury Corn | % Injury VL | % Injury BYG |
|---|---|---|---|---|---|---|
| 4.48 | — | — | — | 7 | 5 | 100 |
| 8.96 | — | — | — | 8 | 33 | 100 |
| — | 2.24 | — | — | 12 | 13 | 38 |
| 4.48 | " | — | — | 35 | 82 | 100 |
| 8.96 | " | — | — | 55 | 88 | 100 |
| — | — | 3 | 8.96 | 0 | 0 | 0 |
| 4.48 | — | " | 2.24 | 0 | 0 | 0 |
| 4.48 | — | " | 8.96 | 0 | 10 | 100 |
| 8.96 | — | " | 2.24 | 0 | 0 | 100 |
| 8.96 | — | " | 8.96 | 0 | 5 | 100 |
| — | 2.24 | " | 2.24 | 0 | 80 | 20 |
| — | " | " | 8.96 | 20 | 65 | 15 |
| 4.48 | " | " | 2.24 | 5 | 100 | 100 |
| 4.48 | " | " | 8.96 | 15 | 100 | 100 |
| 8.96 | " | " | 2.24 | 70 | 100 | 100 |
| 8.96 | " | " | 8.96 | 55 | 100 | 100 |
| — | — | 8 | 8.96 | 10 | 0 | 0 |
| 4.48 | — | " | 2.24 | 0 | 0 | 100 |
| " | — | " | 8.96 | 0 | 0 | 100 |
| 8.96 | — | " | 2.24 | 5 | 10 | 100 |
| " | — | " | 8.96 | 15 | 0 | 100 |
| — | 2.24 | " | 2.24 | 5 | 65 | 90 |
| — | " | " | 8.96 | 25 | 80 | 85 |
| 4.48 | " | " | 2.24 | 25 | 85 | 100 |
| 4.48 | " | " | 8.96 | 20 | 75 | 100 |
| 8.96 | " | " | 2.24 | 40 | 25 | 100 |
| " | " | " | 8.96 | 5 | 100 | 100 |
| — | — | 11 | 8.96 | 0 | 0 | 5 |
| 4.48 | — | " | 2.24 | 0 | 0 | 100 |
| " | — | " | 8.96 | 0 | 5 | 100 |
| 8.96 | — | " | 2.24 | 0 | 70 | 100 |
| 8.96 | — | " | 8.96 | 15 | 40 | 100 |
| — | 2.24 | " | 2.24 | 0 | 60 | 65 |
| — | " | " | 8.96 | 0 | 100 | 90 |
| 4.48 | " | " | 2.24 | 55 | 100 | 100 |
| " | " | " | 8.96 | 55 | 100 | 100 |
| 8.96 | " | " | 2.24 | 70 | 100 | 100 |
| " | " | " | 8.96 | 25 | 100 | 100 |
| — | — | 22 | 8.96 | 5 | 0 | 0 |
| 4.48 | — | " | 2.24 | 0 | 0 | 100 |
| " | — | " | 8.96 | 0 | 0 | 100 |
| 8.96 | — | " | 2.24 | 5 | 10 | 100 |
| " | — | " | 8.96 | 35 | 25 | 100 |
| — | 2.24 | " | 2.24 | 5 | 85 | 90 |
| — | " | " | 8.96 | 0 | 30 | 100 |
| 4.48 | " | " | 2.24 | 35 | 55 | 100 |
| " | " | " | 8.96 | 10 | 90 | 100 |
| 8.96 | " | " | 2.24 | 10 | 100 | 100 |
| " | " | " | 8.96 | 15 | 100 | 100 |
| — | — | 32 | 8.96 | 0 | 0 | 0 |
| 4.48 | — | " | 2.24 | 0 | 25 | 100 |
| " | — | " | 8.96 | 0 | 0 | 100 |
| 8.96 | — | " | 2.24 | 5 | 80 | 100 |
| 8.96 | — | 32 | 8.96 | 0 | 100 | 100 |
| — | 2.24 | " | 2.24 | 0 | 80 | 60 |
| — | " | " | 8.96 | 10 | 90 | 75 |
| 4.48 | " | " | 2.24 | 15 | 100 | 100 |
| " | " | " | 8.96 | 5 | 80 | 100 |
| 8.96 | " | " | 2.24 | 20 | 90 | 100 |
| " | " | " | 8.96 | 50 | 100 | 100 |
| — | — | 45 | 8.96 | 0 | 100 | 0 |
| 4.48 | — | " | 2.24 | 0 | 75 | 100 |
| " | — | " | 8.96 | 0 | 20 | 100 |
| 8.96 | — | " | 2.24 | 0 | 15 | 100 |
| " | — | " | 8.96 | 20 | 25 | 100 |
| — | 2.24 | " | 2.24 | 10 | 85 | 85 |
| — | " | " | 8.96 | 15 | 100 | 25 |
| 4.48 | " | " | 2.24 | 45 | 80 | 100 |
| " | " | " | 8.96 | 15 | 95 | 100 |
| 8.96 | " | " | 2.24 | 15 | 95 | 100 |
| " | " | " | 8.96 | 70 | 100 | 100 |
| — | — | 67 | 8.96 | 0 | 0 | 0 |
| 4.48 | — | " | 2.24 | 15 | 0 | 100 |
| " | — | " | 8.96 | 15 | 25 | 100 |
| 8.96 | — | " | 2.24 | 5 | 0 | 100 |
| " | — | " | 8.96 | 5 | 40 | 100 |
| — | 2.24 | " | 2.24 | 0 | 20 | 0 |
| — | " | " | 8.96 | 35 | 80 | 70 |
| 4.48 | " | " | 2.24 | 35 | 85 | 100 |
| " | " | " | 8.96 | 30 | 50 | 100 |
| 8.96 | " | " | 2.24 | 30 | 80 | 100 |
| " | " | " | 8.96 | 50 | 85 | 100 |
| — | — | 71 | 8.96 | 0 | 10 | 0 |
| 4.48 | — | " | 2.24 | 5 | 10 | 100 |
| " | — | " | 8.96 | 0 | 0 | 100 |
| 8.96 | — | " | 2.24 | 15 | 0 | 100 |
| " | — | " | 8.96 | 5 | 65 | 100 |
| — | 2.24 | 71 | 2.24 | 10 | 50 | 80 |
| — | " | " | 8.96 | 25 | 90 | 80 |
| 4.48 | " | " | 2.24 | 0 | 60 | 100 |
| " | " | " | 8.96 | 0 | 100 | 100 |
| 8.96 | " | " | 2.24 | 55 | 80 | 100 |
| " | " | " | 8.96 | 75 | 100 | 100 |
| — | — | 74 | 8.96 | 0 | 0 | 40 |
| 4.48 | — | " | 2.24 | 15 | 60 | 100 |

TABLE IX-continued

| Herbicide | | Antidote | | % Injury | | |
|---|---|---|---|---|---|---|
| Metolachlor Rate | Dicamba Rate | No. | Rate | Corn | VL | BYG |
| " | — | " | 8.96 | 0 | 0 | 100 |
| 8.96 | — | " | 2.24 | 0 | 45 | 100 |
| " | — | " | 8.96 | 0 | 60 | 100 |
| — | 2.24 | " | 2.24 | 20 | 85 | 75 |
| — | " | " | 8.96 | 15 | 85 | 80 |
| 4.48 | " | " | 2.24 | 25 | 85 | 100 |
| " | " | " | 8.96 | 45 | 100 | 100 |
| 8.96 | " | " | 2.24 | 25 | 100 | 100 |
| " | " | " | 8.96 | 15 | 100 | 100 |

In the above tests, all antidotal compounds safened corn from the combinations of dicamba and metolachlor. Antidote No. 22 was the most active compound reducing injury to corn by the 8.96:2.24 kg/ha metolachlor:dicamba combination without the antidote from 55% to 10% with addition of 2.24 kg/ha of the antidote.

EXAMPLE 15

This example illustrates the safening effect of Antidote No. 78 against dicamba in combination with metolachlor. The antidote was supplied in the form of Dual II ® herbicide containing 89.3 wt.% of metolachlor, 2.7 wt.% of Antidote No. 78 and 13.4 wt.% inerts.

The procedure of this example was the same as described in the preceding example, including the number of replications to obtain the stated percent injury average values. The test weed was velvetleaf; barnyardgrass was not present in this test. Test results are shown in Table X.

TABLE X

| Herbicide | | Antidote | | % Injury | |
|---|---|---|---|---|---|
| Metolachlor Rate | Dicamba Rate | No. | Rate | Corn | VL |
| 8.96 | — | 78 | — | 95 | 0 |
| 4.48 | — | " | — | 18 | 0 |
| 2.24 | — | " | — | 0 | 0 |
| — | 4.48 | " | — | 25 | 43 |
| — | 2.24 | " | — | 7 | 11 |
| — | 1.12 | " | — | 2 | 7 |
| 8.96 | — | " | 0.28 | 0 | 27 |
| 4.48 | — | " | 0.14 | 0 | 0 |
| 2.24 | — | " | 0.07 | 0 | 2 |
| 8.96 | 4.48 | " | — | 93 | 100 |
| 4.48 | " | " | — | 70 | 100 |
| 2.24 | " | " | — | 65 | 100 |
| 8.96 | 2.24 | " | — | 83 | 98 |
| 4.48 | " | " | — | 58 | 65 |
| 2.24 | " | " | — | 40 | 70 |
| 8.96 | 1.12 | " | — | 85 | 90 |
| 4.48 | " | " | — | 30 | 40 |
| 2.24 | " | " | — | 13 | 13 |
| 8.96 | 4.48 | " | 0.28 | 82 | 100 |
| 4.48 | " | " | 0.14 | 30 | 100 |
| 2.24 | " | " | 0.07 | 10 | 60 |
| 8.96 | 2.24 | " | 0.28 | 30 | 80 |
| 4.48 | " | " | 0.14 | 15 | 90 |
| 2.24 | " | " | 0.07 | 10 | 62 |
| 8.96 | 1.12 | " | 0.28 | 22 | 55 |
| 4.48 | " | " | 0.14 | 5 | 18 |
| 2.24 | " | " | 0.07 | 0 | 5 |

It is noted in Table X that neither metolachlor nor dicamba alone provided adequate weed control at maximum test rates up to 8.96 kg/ha for metolachlor and 4.48 kg/ha for dicamba. However, combinations of these herbicides did provide adequate control. Antidote 78 reduced corn injury from 8.96 metolachlor plus 1.12 Dicamba from 85 to 22% at 0.28 kg/ha.

EXAMPLE 16

This example describes the antidotal effect of various antidotal compounds against dicamba in wheat and in corn. The test weed in these tests was redroot pigweed (Amaranthus retroflexus, Rrpw in Table 11).

The test procedure used in this example was the same as described in Example 11, except using a single herbicide rather than a combination of dicamba and a co-herbicide. Test data for the wheat experiments are shown in Table XI and for the corn experiments in Table XII.

TABLE XI

| | | | | % Plant Inhibition | |
|---|---|---|---|---|---|
| Antidote No. | Rate Kg/Ha | Herbicide | Rate Kg/Ha | Wheat | Rrpw |
| — | — | Dicamba | 0.56 | 12 | 95 |
| — | — | " | 2.24 | 65 | 100 |
| 1 | 8.96 | " | 2.24 | 40 | 100 |
| 1 | " | " | 0.56 | 15 | 80 |
| 1 | " | " | | 0 | 0 |
| 1 | 2.24 | " | 2.24 | 55 | 85 |
| 1 | " | " | 0.56 | 0 | 100 |
| 1 | 0.56 | " | 2.24 | 85 | 100 |
| 1 | " | " | 0.56 | 0 | 100 |
| 4 | 8.96 | " | 2.24 | 90 | 100 |
| 4 | " | " | 0.56 | 0 | 90 |
| 4 | " | " | | 0 | 0 |
| 4 | 2.56 | " | 2.24 | 15 | 100 |
| 4 | " | " | 0.56 | 5 | 55 |
| 4 | 0.56 | " | 2.24 | 50 | 100 |
| 4 | " | " | 0.56 | 10 | 100 |
| 5 | 8.96 | " | 2.24 | 30 | 100 |
| 5 | " | " | 0.56 | 5 | 90 |
| 5 | " | " | | 0 | 0 |
| 5 | 2.24 | " | 2.24 | 15 | 100 |
| 5 | " | " | 0.56 | 0 | 80 |
| 5 | 0.56 | " | 2.24 | 10 | 100 |
| 5 | " | " | 0.56 | 0 | 100 |
| 7 | 8.96 | " | 2.24 | 10 | 100 |
| 7 | " | " | 0.56 | 0 | 95 |
| 7 | " | " | | 0 | 0 |
| 7 | 2.24 | " | 2.24 | 20 | 75 |
| 7 | " | " | 0.56 | 10 | 80 |
| 7 | 0.56 | " | 2.24 | 30 | 100 |
| 7 | " | " | 0.56 | 0 | 100 |
| 9 | 8.96 | " | 2.24 | 10 | 85 |
| 9 | " | " | 0.56 | 0 | 95 |
| 9 | " | " | | 10 | 0 |
| 9 | 2.24 | " | 2.24 | 15 | 90 |
| 9 | 2.24 | Dicamba | 0.56 | 10 | 25 |
| 9 | 0.56 | " | 2.24 | 45 | 100 |
| 9 | " | " | 0.56 | 0 | 100 |
| 11 | 8.96 | " | 2.24 | 15 | 100 |
| 11 | " | " | 0.56 | 0 | 85 |
| 11 | " | " | | 0 | 0 |
| 11 | 2.24 | " | 2.24 | 10 | 70 |
| 11 | " | " | 0.56 | 0 | 95 |
| 11 | 0.56 | " | 2.24 | 60 | 100 |
| 11 | " | " | 0.56 | 5 | 100 |
| 12 | 8.96 | " | 2.24 | 40 | 100 |
| 12 | " | " | 0.56 | 10 | 90 |
| 12 | " | " | | 0 | 100 |
| 12 | 2.24 | " | 2.24 | 15 | 85 |
| 12 | " | " | 0.56 | 10 | 95 |
| 12 | 0.56 | " | 2.24 | 10 | 100 |
| 12 | " | " | 0.56 | 10 | 100 |
| 13 | 8.96 | " | 2.24 | 20 | 100 |
| 13 | " | " | 0.56 | 0 | 100 |
| 13 | " | " | | 0 | 95 |
| 13 | 2.24 | " | 2.24 | 0 | 100 |
| 13 | " | " | 0.56 | 0 | 60 |
| 13 | 0.56 | " | 2.24 | 15 | 100 |
| 13 | " | " | 0.56 | 0 | 100 |
| 29 | 8.96 | " | 2.24 | 45 | 100 |
| 29 | " | " | 0.56 | 0 | 100 |
| 29 | " | " | | 0 | 80 |

TABLE XI-continued

| Antidote No. | Rate Kg/Ha | Herbicide | Rate Kg/Ha | Wheat | Rrpw |
|---|---|---|---|---|---|
| 29 | 2.24 | " | 2.24 | 10 | 85 |
| 29 | " | " | 0.56 | 10 | 65 |
| 29 | 0.56 | " | 2.24 | 0 | 70 |
| 29 | " | " | 0.56 | 20 | 90 |
| 76 | 8.96 | " | 2.24 | 100 | 100 |
| 76 | " | " | 0.56 | 100 | 100 |
| 76 | " | " |  | 95 | 100 |
| 76 | 2.24 | Dicamba | 2.24 | 100 | 100 |
| 76 | " | " | 0.56 | 90 | 100 |
| 76 | 0.56 | " | 2.24 | 35 | 100 |
| 76 | " | ' | 0.56 | 60 | 100 |
| 32 | 8.96 | " | 2.24 | 0 | 100 |
| 32 | " | " | 0.56 | 0 | 90 |
| 32 | " | " |  | 0 | 0 |
| 32 | 2.24 | " | 2.24 | 30 | 100 |
| 32 | " | " | 0.56 | 0 | 100 |
| 32 | 0.56 | " | 2.24 | 10 | 100 |
| 32 | " | " | 0.56 | 0 | 100 |
| 32 | 8.96 | " | 2.24 | 30 | 100 |
| 32 | " | " | 0.56 | 0 | 100 |
| 32 | 8.96 | " |  | 5 | 80 |
| 32 | 2.24 | " | 2.24 | 15 | 100 |
| 32 | " | " | 0.56 | 0 | 100 |
| 32 | 0.56 | " | 2.24 | 65 | 100 |
| 32 | " | " | 0.56 | 0 | 95 |
| 39 | 8.96 | " | 2.24 | 10 | 100 |
| 39 | " | " | 0.56 | 0 | 100 |
| 39 | " | " |  | 0 | 0 |
| 39 | 2.24 | " | 2.24 | 15 | 100 |
| 39 | " | " | 0.56 | 0 | 95 |
| 39 | 0.56 | " | 2.24 | 10 | 100 |
| 39 | " | " | 0.56 | 10 | 100 |
| 40 | 8.96 | " | 2.24 | 5 | 100 |
| 40 | " | " | 0.56 | 0 | 100 |
| 40 | " | " |  | 0 | 0 |
| 40 | 2.24 | " | 2.24 | 10 | 100 |
| 40 | " | " | 0.56 | 0 | 85 |
| 40 | 0.56 | " | 2.24 | 45 | 100 |
| 40 | " | " | 0.56 | 35 | 100 |
| 45 | 8.96 | " | 2.24 | 10 | 100 |
| 45 | " | " | 0.56 | 0 | 100 |
| 45 | 8.96 | Dicamba |  | 5 | 100 |
| 45 | 2.24 | " | 2.24 | 25 | 100 |
| 45 | " | " | 0.56 | 10 | 100 |
| 45 | 0.56 | " | 2.24 | 20 | 100 |
| 45 | " | " | 0.56 | 0 | 95 |
| 74 | 8.96 | " | 2.24 | 40 | 100 |
| 74 | " | " | 0.56 | 0 | 100 |
| 74 | " | " |  | 0 | 0 |
| 74 | 2.24 | " | 2.24 | 35 | 100 |
| 74 | " | " | 0.56 | 0 | 95 |
| 74 | 0.56 | " | 2.24 | 70 | 100 |
| 74 | " | " | 0.56 | 10 | 100 |

It is noted from the data in Table XI that the herebicidal effect of dicamba against wheat was reduced by a number of the test antidotes. Antidote No. 39 was most active in this test, reducing injury to wheat by dicamba from 65% at 2.24 kg/ha to 0% with only 0.56 kg/ha of the antidote.

TABLE XII

| Antidote No. | Rate Kg/Ha | Herbicide | Rate Kg/Ha | Corn | Rrpw |
|---|---|---|---|---|---|
| — | — | Dicamba | 4.48 | 35 | 50 |
| — | — | " | 1.12 | 10 | 50 |
| 40 | 8.96 | " | 4.48 | 5 | 60 |
| 40 | " | " | 1.12 | 0 | 35 |
| 40 | " | " |  | 0 | 0 |
| 40 | 2.24 | " | 4.48 | 15 | 95 |
| 40 | " | " | 1.12 | 5 | 65 |
| 40 | 0.56 | " | 4.48 | 35 | 100 |
| 40 | " | " | 1.12 | 10 | 60 |
| 74 | 8.96 | " | 4.48 | 0 | 30 |
| 74 | " | " | 1.12 | 0 | 25 |
| 74 | " | " |  | 5 | 50 |
| 74 | 2.24 | " | 4.48 | 25 | 90 |
| 74 | " | " | 1.12 | 0 | 75 |
| 74 | 0.56 | " | 4.48 | 15 | 75 |
| 74 | " | ' | 1.12 | 10 | 60 |
| 75 | 8.96 | " | 4.48 | 10 | 95 |
| 75 | " | " | 1.12 | 10 | 90 |
| 75 | " | " |  | 0 | 0 |
| 75 | 2.24 | " | 4.48 | 10 | 85 |
| 75 | " | " | 1.12 | 0 | 95 |
| 75 | 0.56 | " | 4.48 | 10 | 95 |
| 75 | 0.56 | " | 1.12 | 0 | 55 |

From the data in Table XII it is noted that the herbicidal effect of dicamba against corn was reduced by all of the test antidotes at 8.96 kg/ha. For example, corn injury by dicamba alone was 35% at 4.48 kg/ha. That degree of injury at the same dicamba rate was reduced to 5%, 0% and 10%, respectively, by antidote nos. 40, 74 and 75 at a rate of 8.96 kg/ha.

While the invention herein has been specifically exemplified with the commercial herbicidal compound dicamba as representative of the compounds of Formula I, by alachlor, acetochlor and metolachlor as representative of the compounds of Formula V and by various dichloroacetamide antidotes such as AD-67 and the safener of formulation V as representative of the compounds according to Formulae II and III, as well as a multiplicity of other antidotes having a variety of chemical structures, it is to be understood that other compounds within the scope of the above formulae and other chemical classes are specifically contemplated as within the scope of this invention For example, other benzoic acid derivatives contemplated herein include the compounds described in U.S. Pat. No. 3,013,054.

The above specifically mentioned herbicidal compounds used as co-herbicides herein are intended merely as exemplary of the classes of herbicides which they represent. However, it is expressly contemplated that many other herbicidal compounds analogous to those represented herein having a variety of equivalent radicals substituted on the central nucleus may similarly be safened to various crop plants to a greater or lesser extent with the antidotal compounds of this invention. For example, other α-haloacetamide and α-haloacetanilide compounds useful as herbicides are described in U.S. Pat. Nos. 3,442,945, 3,547,620, 3,574,746, 3,586,496, 3,830,841, 3,901,768, 4,249,935, 4,319,918, 4,517,011, 4,601,745, 4,657,579 and 4,666,502 and Australian Patent No. AU-A1-18044/88.

Herbicidally-useful thiocarbamate compounds are described in U.S. Pat. Nos. 2,913,327, 3,330,643 and 3,330,821.

Other herbicidal pyridine compounds are described in U.S. Pat. No. 4,692,184 and copending U.S. Pat. No. 4,826,532 and U.S. Pat. No. 4,826,532, both of common assignment herewith.

Herbicidally-useful heterocycyl phenyl ethers (especially pyrazolyl aryl ethers) are described, e.g., in U.S. Pat. No. 4,298,749.

Herbicidal diphenyl ethers and nitrophenyl ethers include 2,4-dichlorophenyl 4'-nitrophenyl ether ("nitrofen"), 2-chloro-1-(3'-ethoxy-4'-nitrophenoxy)-4-trifluoromethylbenzene ("Oxyfluorfen"), 2',4'- dichlorophenyl 3-methoxy-4-nitrophenyl ether ("Chlormethoxynil"), methyl 2-[4'-(2",4"-dichlorophenoxy)-phenoxy]propionate, N-(2'-phenoxyethyl)-2-[5'-(2"-chloro-4"-trifluoromethylphenoxy)-phenoxy]-propionamide, 2-methoxyethyl 2-[nitro-5-(2-chloro-4-trifluoromethylphenoxy)-phenoxyl-propionate and 2-chloro-4-trifluoromethylphenyl 3'-oxazolin-2'-yl-4'-nitrophenylether.

Another generic class of agrichemically-important herbicidal compounds specifically contemplated for use as co-herbicidal compounds in combination with the antidotal compounds of this invention are the ureas and sulfonylurea derivatives. Important herbicidal ureas include 1-(benzothiazol-2-yl)-1,3-dimethylurea; phenylureas, for example: 3-(3-chloro-p-tolyl)-1,1-dimethylurea ("chlorotoluron"), 1,1-dimethyl-3-(α, α, α-trifluoro-m-tolyl)urea ("fluometuron"), 3-(4-bromo-3-chlorophenyl)-methoxy-1-methylurea ("chlorbromuron"), 3-(4-bromophenyl)-1-methoxy-1-methylurea ("metobromuron"), 3-(3,4-dichlorophenyl)-1-methoxy-1-methylurea ("linuron"), 3-(4-chlorophenyl)-1-methoxy-1-methylurea ("monolinuron"), 3-(3,4-dichlorophenyl)-1,1-dimethyllurea ("diuron"), 3-(4-chlorophenyl)-1,1-dimethylurea ("monuron") and 3-(3-chloro-4-methoxyphenyl)-1,1-dimethylurea ("metoxuron");

Important herbicidal sulfonylureas and sulfonamides specifically contemplated as useful as coherbicides in compositions with the antidotal compounds of this invention include those disclosed in the following patents: U.S. Pat. Nos. 4,383,113, 4,127,405, 4,479,821, 4,481,029, 4,514,212, 4,420,325, 4,638,004, 4,675,046, 4,681,620, 4,741,760, 4,723,123, 4,411,690, 4,718,937, 4,620,868, 4,668,277, 4,592,776, 4,666,508, 4,696,695, 4,731,446, 4,678,498, 4,786,314, 4,889,550 and 4,668,279; EP Numbers 084224, 173312, 190105, 256396, 264021, 264672, 142152, 244847, 176304, 177163, 187470, 187489, 184385, 232067, 234352, 189069, 224842, 249938, 246984 and 246984 and German Offen. DE 3,618,004.

Among the herbicidal sulfonylureas disclosed in one or more of the above patents which are of particular interest are mentioned the species N-[(4-methoxy-6-methylpyrimidin-2-yl)aminocarbonyl]-3-chloro-4-methoxy-carbonyl-1-methylpyrazole-5-sulfonamide; N-[(4,6-dimethoxypyrimidin-2-yl)aminocarbonyl]-3-chloro-4-methoxycarbonyl-1-methylpyrazole-5-sulfonamide; N-[(4-methoxy-6-methylpyrimidin-2-yl)aminocarbonyl]-3-chloro-4-ethoxycarbonyl-1-methylpyrazole-5-sulfonamide; N-[(4,6-dimethoxypyrimidin-2-yl)aminocarbonyl]-3-chloro-4-ethoxycarbonyl-1-methylpyrazole-5-sulfonamide; N-[(4-methoxy-6-methylpyrimidin-2-yl)aminocarbonyl]-3-bromo-4-ethoxycarbonyl-1-methylpyrazole-5-sulfonamide; N-[(4,6-dimethoxypyrimidin-2-yl)aminocarbonyl]-3-bromo-4-ethoxy-carbonyl-1-methylpyrazole-5-sulfonamide; N-(methoxycarbonyl-1-phenyl sulfonyl-N'-(bis-difluoromethoxypyrimidin-2-yl)urea and N-[(4,6-dimethoxypyrimidin-2-yl)-aminocarbonyl]-4-ethoxycarbonyl-1-methylpyrazole-5-sulfonamide.

Other herbicidal imidazolinone or imidazolidinone or -dione compounds within the purview of this invention as co-herbicides which may be safened for use in various crops include the compounds disclosed in the following exemplary publications: EP Numbers 041623, 133310, 198552, 216360 and 298029; JA 1109-790, JA 1197-580A, J6 1183-272A and J6 3196-750A; and Australian published Application No. AU 8661-073A, GB 2 172 886A and U.S. Pat. Nos. 4,188,487, 4,297,128, 4,562,257, 4,554,013, 4,647,301, 4,638,068, 4,650,514, 4,709,036, 4,749,403, 4,749,404, 4,776,619, 4,798,619 and 4,741,767.

Still other classes of herbicidal compounds contemplated for combination with benzoic acid derivatives and the antidotes of this invention include the following representative species:

Triazines and triazinones: 2,4-bis-(isopropylamino)-6-methylthio-1,3,5-triazine ("prometryn"), 2,4-bis-(ethylamino)-6-methylthio-1,3,5-triazine ("simetryn"), 2-(1',2'-dimethylpropylamino)-4-ethylamino-6-methylthio-1,3,5-triazine ("dimethametryn"), 2-(chloro-4,6-bis(ethylamino)-1,3,5-triazine ("simazine"), 2-tert-butylamino-4-chloro-6-ethylamino-1,3,5-triazine ("terbuthylazine"), 2-tert-butylamino-4-ethylamino-6-methoxy-1,3,5-triazine ("terbumeton"), 2-tert-butylamino-4-ethylamino-6-methylthio-1,3,5-triazine ("terbutryn"), 2-ethylamino-4-isopropylamino-6-methylthio-1,3,5-triazine ("ametryn") and 3,4-bis-(methylamino)-6-tert-butyl-4,4-dihydro-1,2,4-triazin-5-one.

Oxadiazolones: 5-tert-butyl-3-(2',4'-dichloro-5'-isopropoxyphenyl)-1,3,4-oxadiazol-2-one ("Oxadiazon").

Phosphates: S-2-methylpiperidinocarbonylmethyl O,O-dipropyl phosphorodithioate ("Piperophos").

Pyrazoles: 1,3-dimethyl-4-(2',4'-dichlorobenzolyl)-5-(4-'-tolylsulfonyloxy)-pyrazole; aryl- and heterocyclic-substituted pyrazoles, e.g., as exemplified in EP No. 0361114; Japanese Kokai No. JP 50137061 and U.S. Pat. No. 4,008,249, preferred species of such substituted-pyrazole compounds include 4-chloro-3-(4-chloro-2-fluoro-5-(2-propynyloxy)phenyl)-1-methyl-5-(methylsulfonyl)-1H pyrazole and analogs thereof, e.g., where the substituent in the 5-position of the pyrazole ring is a haloalkyl radical, preferably $CF_3$.

Also α-(phenoxyphenoxy)-propionic acid derivatives and α-pyridyl-2-oxyphenoxy)-propionic acid derivatives.

Other herbicidal compounds useful as coherbicides with the benzoic acid compounds of Formula I include aromatic and heterocyclic di- and triketones exemplified in U.S. Pat. Nos. 4,797,147, 4,853,028, 4,854,966, 4,855,477 and 4,869,748.

Still other co-herbicidal compounds contemplated herein are pyrrolidinones, e.g, the 1-phenyl-3-carboxyamidopyrrolidinones disclosed in U.S. Pat. No. 4,874,422, etc.

Still other herbicidal compounds useful as coherbicides herein include imidazolopyrimidine sulfonamides of the type exemplified by and disclosed in U.S Pat. Nos. 4,731,446 and 4,799,952; triazolopyrimidine aminosulfones of the type disclosed in U.S. Pat. Nos. 4,685,958, 4,822,404 and 4,830,663; triazolopyrimidine sulfonamides of the type disclosed in EP 340828 and EP 343752 and U.S. Pat. Nos. 4,755,212, 4,818,273, 4,886,883, 4,904,301, 4,889,553 and 4,910,306.

In addition to the antidotal compounds exemplified herein, other representative antidotal compounds according to Formula II or other structure are expressly disclosed in various patents, e.g., U.S. Pat. Nos. 3,959,304, 4,072,688, 4,137,070, 4,124,372, 4,124,376, 4,483,706, 4,636,244, 4,033,756, 4,493,726, 4,708,735, 4,256,481, 4,199,506, 4,251,261, 4,070,389, 4,231,783, 4,269,775, 4,152,137 and 4,294,764, and EP Nos. 0253291, 0007588, 190105, 0229649, 16618 and W. German Patent Application Nos. 28 28 222, 28 28 293.1, and 29 30 450.5, South African Patent No. 82/7681 and PRC Application No. 102 879-87.

As will be appreciated by those skilled in the art, the practice of this invention comprises the use of the antidotal compounds disclosed and claimed herein with any herbicidally-active benzoic acid or derivative compound which may optionally be combined with coherbicides from many different classes of chemistry. Obviously, the above listings of exemplary compounds is not intended to be exhaustive, but representative. Again, as noted earlier herein, it is expected that not every combination of herbicide and antidote will result in safening of all crops, but is within the skill of the art to test any given herbicide with an invention antidote in plant screens of any spectrum of plants and note the results.

The foregoing embodiments illustrate that the combinations of herbicide and antidote of this invention are useful in controlling weeds while reducing herbicidal injury to crop plants under greenhouse and field test conditions.

In field applications, the herbicide, antidote, or a mixture thereof, may be applied to the plant locus without any adjuvants other than a solvent. Usually, the herbicide, antidote, or a mixture thereof, is applied in conjunction with one or more adjuvants in liquid or solid form. Compositions or formulations containing mixtures of an appropriate herbicide(s) and antidote usually are prepared by admixing the herbicide and antidote with one or more adjuvants such as diluents, solvents, extenders, carriers, conditioning agents, water, wetting agents, dispersing agents, or emulsifying agents, or any suitable combination of these adjuvants. These mixtures may be in the form of emulsifiable concentrates, microencapsulates, particulate solids, granules of varying particle size, e.g., water-dispersible or water-soluble granules or larger dry granules, pellets, wettable powders, dusts, solutions, aqueous dispersions, or emulsions.

Examples of suitable adjuvants are finelydivided solid carriers and extenders including talcs, clays, pumice, silica, diatomaceous earth, quartz, Fuller's earth, sulfur, powdered cork, powdered wood, walnut flour, chalk, tobacco dust, charcoal, and the like. Typical liquid diluents include Stoddard's solvent, acetone, methylene chloride, alcohols, glycols, ethyl acetate, benzene, and the like. Liquids and wettable powdersusually contain as a conditioning agent one or more surface-active agents in amounts sufficient to make a composition readily dispersible in water or in oil. The term "surface-active agent" includes wetting agents, dispersing agents, suspending agents, and emulsifying agents. Typical surface-active agents are mentioned in U.S. Pat. No. 2,547,724.

Compositions of this invention generally contain from about 5 to 95 parts herbicide-and-antidote, about 1 to 50 parts surface-active agent, and about 4 to 94 parts solvent, all parts being by weight based on the total weight of the composition.

Application of the herbicide, antidote, or mixture thereof, can be carried out by conventional techniques utilizing, for example, hand-carried or tractor-mounted spreaders, power dusters, boom and hand sprayers, spray dusters, and granular applicators. If desired, application of the compositions of the invention to plants can be accomplished by incorporating the compositions in the soil or other media.

The crop may be protected by treating the crop seed with an effective amount of antidote prior to planting. Generally, smaller amounts of antidote are required to treat such seeds. A weight ratio of as little as 0.6 parts of antidote per 1000 parts of seed may be effective. The amount of antidote utilized in treating the seed may be increased if desired. Generally, however, a weight ratio of antidote-to-seed weight may range from 0.1 to 10.0 parts of antidote per 1000 parts of seed. Since only a very small amount of active antidote is usually required for the seed treatment, the compound preferably is formulated as an organic solution, powder, emulsifiable concentrate, water solution, or flowable formulation, which can be diluted with water by the seed treater for use in seed treating apparatus. Under certain conditions, it may be desirable to dissolve the antidote in an organic solvent or carrier for use as a seed treatment or the pure compound alone may be used under properly controlled conditions.

For antidote seed-coating for antidotes applied to soil in granular or liquid formulations, suitable carriers may be either solids, such as talc, sand, clay, diatomaceous earth, sawdust, calcium carbonate, and the like, or liquids, such as water, kerosene, acetone, benzene, toluene, xylene and the like, in which the active antidote may be either dissolved or dispersed. Emulsifying agents are used to achieve a suitable emulsion if two immiscible liquids are used as a carrier. Wetting agents may also be used to aid in dispersing the active antidote in liquids used as a carrier in which the antidote is not completely soluble. Emulsifying agents and wetting agents are sold under numerous tradenames and trademarks and may be either pure compounds, mixtures of compounds of the same general groups, or they may be mixtures of compounds of different classes. Typical satisfactory surface active agents which may be used are alkali metal higheralkylarylsulfonates such as sodium dodecylbenzenesulfonate and the sodium salts of alkylnaphthalenesulfonic acids, fatty alcohol sulfates such as the sodium salts of monoesters of sulfuric acid with naliphatic alcohols containing 8-18 carbon atoms, longchain quaternary ammonium compounds, sodium salts of petroleum-derived alkylsulfonic acids, polyethylene sorbitan monooleate, alkylaryl polyether alcohols, water-soluble lignin sulfonate salts, alkali casein compositions, long-chain alcohols usually containing 10-18 carbon atoms, and condensation products of ethylene oxide with fatty acids, alkylphenols and mercaptans.

Although this invention has been described with respect to specific embodiments, the details of these embodiments are not to be construed as limitations. Various equivalents, changes and modifications may be made without departing from the spirit and scope of this invention, and it is understood that such equivalent embodiments are part of this invention.

We claim:
1. Composition consisting essentially of
(a) a herbicidally-effective amount of one or more compounds of the formula

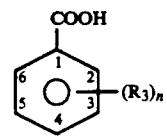

agriculturally-acceptable salts thereof wherein
$R_3$ is halogen, $C_{1-5}$ alkoxy or $C_{1-4}$ alkyl-substituted amino and n is 0–5 and
(b) an antidotally-effective amount of
(i) a compound of the formula

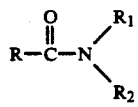

wherein R can be selected from the group consisting of haloalkyl; haloalkenyl; alkyl; alkenyl; cycloalkyl; cycloalkylalkyl; halogen; hydrogen; carboalkoxy; N-alkenylcarbamylalkyl; N-alkenylcarbamyl; N-alkyl-N-alkynylcarbamyl; N-alkyl-N-alkynylcarbamylalkyl; N-alkenylcarbamylalkoxyalkyl; N-alkyl-N-alkynylcarbamylalkoxyalkyl; alkynoxy; haloalkoxy; thiocyanatoalkyl; alkenylaminoalkyl; alkylcarboalkyl; cyanoalkyl; cyanatoalkyl; alkenylaminosulfonoalkyl; alkylthioalkyl; haloalkylcarbonyloxyalkyl; alkoxycarboalkyl; haloalkenylcarbonyloxyalkyl; hydroxyhaloalkyloxyalkyl; hydroxyalkylcarboalkyoxyalkyl; hydroxyalkyl; alkoxysulfonoalkyl; furyl, thienyl; alkyldithiolenyl; thienalkyl; phenyl and substituted phenyl wherein said substituents can be selected from halogen, alkyl, haloalkyl, alkoxy, carbamyl, nitro, carboxylic acids and their salts, haloalkylcarbamyl; phenylalkyl; phenylhaloalkyl; phenylalkenyl; substituted phenylalkenyl wherein said substituents can be selected from halogen, alkyl, alkoxy, halophenoxy, phenylalkoxy; phenylalkylcarboxyalkyl; phenylcycloalkyl; halophenylalkenoxy; halothiophenylalkyl; halophenoxyalkyl; bicycloalkyl; alkenylcarbamylpyridinyl; alkynylcarbamylpyridinyl; dialkenylcarbamylbicycloalkenyl; alkynylcarbamylbicycloalkenyl;

R$_1$ and R$_2$ can be the same or different and can be selected from the group consisting of alkenyl; haloalkenyl; hydrogen; alkyl; haloalkyl; alkynyl; cyanoalkyl; hydroxyalkyl; hydroxyhaloalkyl; haloalkylcarboxyalkyl; alkylcarboxyalkyl; alkoxycarboxyalkyl; thioalkylcarboxyalkyl; alkoxycarboalkyl; alkylcarbamyloxyalkyl; amino; formyl; haloalkyl-N-alkylamido; haloalkylamido; haloalkylamidoalkyl; haloalkyl-N-alkylamidoalkyl; haloalkylamidoalkenyl; alkylimino; cycloalkyl; alkylcycloalkyl; alkoxyalkyl; alkylsulfonyloxyalkyl; mercaptoalkyl; alkylaminoalkyl; alkoxycarboalkenyl; haloalkylcarbonyl; alkylcarbonyl; alkenylcarbamyloxyalkyl; cycloalkylcarbamyloxyalkyl; alkoxycarbonyl; haloalkoxycarbonyl; halophenylcarbamyloxyalkyl; cycloalkenyl; phenyl; substituted phenyl wherein said substituents can be selected from alkyl, halogen, haloalkyl, alkoxy, haloalkylamido, phthalamido, hydroxy, alkylcarbamyloxy, alkenylcarbamyloxy, alkylamido, haloalkylamido or alkylcarboalkenyl; phenylsulfonyl; substituted phenylalkyl wherein said substituents can be selected from halogen or alkyl; dioxyalkylene, halophenoxyalkylamidoalkyl; alkylthiodiazolyl; piperidyl; piperidylalkyl; dioxolanylalkyl, thiazolyl; alkylthiazolyl; benzothiazolyl; halobenzothiazolyl; furyl; alkyl-substituted furyl; furylalkyl; pyridyl; alkylpyridyl; alkyloxazolyl; tetrahydrofurylalkyl; 3-cyano, thienyl; alkyl-substituted thienyl; 4,5-polyalkylenethienyl; α-haloalkylacetamidophenylalkyl; α-haloalkylacetamidonitrophenylalkyl; α-haloalkylacetamidohalophenylalkyl; cyanoalkenyl;

R$_1$ and R$_2$ when taken together can form a structure consisting of piperidinyl; alkylpiperidinyl; pyridyl; di- or tetrahydropyridinyl; alkyltetrahydropyridyl; morpholyl; alkylmorpholyl; azabicyclononyl; diazacycloalkanyl; benzoalkylpyrrolidinyl; oxazolidinyl; perhydrooxazolidinyl; alkyloxazolidyl; pyrimidinyloxazolidinyl; benzooxazolidinyl; C$_{3-7}$ spirocycloalkyloxazolidinyl; alkylaminoalkenyl; alkylideneimino; pyrrolidinyl; piperidonyl; perhydroazepinyl; perhydroazocinyl; pyrazolyl; dihydropyrazolyl; piperazinyl; perhydro-1,4-diazepinyl; quinolinyl; isoquinolinyl; dihydro-, tetra- hydro- and perhydroquinolyl- or -isoquinolyl; indolyl and di- and perhydroindolyl and said combined R$_1$ and R$_2$ members substituted with those independent R$_1$ and R$_2$ radicals enumerated above; or (ii) one of the following compounds
α-[(Cyanomethoxy)imino]benzeneacetonitrile,
α-[(1,3-Dioxolan-2-yl-methoxy)imino]benzeneacetonitrile,
O-[1,3-Dioxolan-2-ylmethyl]-2,2,2-trifluoromethyl-4'-chloroacetophenone oxime,
Benzenemethamine, N-[4-(dichloromethylene)-1,3-dithiolan-2-ylidene]-α-methyl, hydrochloride,
Diphenylmethoxy acetic acid, methyl ester,
1,8-Naphthalic anhydride,
4,6-Dichloro-2-phenyl-pyrimidine,
2-Chloro-N-[1-(2,4,6-trimethylphenyl)ethenyl]acetamide,
Ethylene glycol acetal of 1,1-dichloroacetone.

2. Composition according to claim 1 wherein n in Formula I is 3, and two of the R$_3$ members are halogen and the third R$_3$ member is C$_{1-5}$ alkoxy or C$_{1-4}$-alkyl-substituted amino.

3. Composition according to claim 2 wherein said two halogen members are chlorine and said third R$_3$ member is a C$_{1-5}$ alkoxy radical.

4. Composition according to claim 3 wherein said compound of component (a) is 3,6-dichloro-2-methoxybenzoic acid.

5. Composition according to claim 1 wherein component (a) is an alkali metal salt, or dimethyl- or diethylamine-, morpholinyl or ammonium salt of 3,6-dichloro-2-methoxybenzoic acid.

6. Composition according to claim 5 wherein component (a) is the sodium or potassium salt of 3,6-dichloro-2-methoxybenzoic acid.

7. Composition according to claim 5 wherein component (a) is the dimethylammonium salt of 3,6-dichloro-2-methoxybenzoic acid.

8. Composition according to claim 5 wherein component (a) is the diethylamine salt of 3,6-dichloro-2-methoxybenzoic acid.

9. Composition according to any of claims 1–7 or 8 wherein in Formula II for the antidote of component (b)
R is C$_{1-3}$ haloalkyl;
R$_1$ and R$_2$ are independently C$_{2-4}$ alkenyl, haloalkenyl or 1,3-dioxolan-2-yl-methyl or
R$_1$ and R$_2$ when combined form a C$_{4-10}$ saturated or unsaturated heterocyclic ring containing from 1 to 4 ring hetero atoms selected independently from O, S or N atoms and which may be substituted with C$_{1-5}$ alkyl, haloalkyl, alkoxy, or alkoxyalkyl or haloacyl groups.

10. Composition according to claim 1 wherein R is dichloromethyl.

11. Composition according to claim 10 wherein said compound of component (b) is N,N-diallyl-dichloroacetamide.

12. Composition according to claim 10 wherein said compound of component (b) is N-(2-propenyl)-N-(1,3-dioxolanylmethyl)dichloroacetamide.

13. Composition according to claim 1, 7 or 8 wherein said compound of component (b) is a substituted 1,3-oxazolidinyl dichloroacetamide having the formula

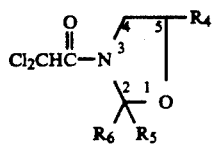

wherein $R_4$ is hydogen, $C_{1-4}$ alkyl, alkylol, haloalkyl or alkoxy, $C_{2-6}$ alkoxyalkyl, a bicyclic hydrocarbon radical having up to 10 carbon atoms, phenyl or phenyl heterocyclic substituted with one or more $C_{1-4}$ alkyl, haloalkyl, alkoxy, alkoxyalkyl, halogen or nitro radicals, and $R_5$ and $R_6$ are independently hydrogen, $C_{1-4}$ alkyl or haloalkyl, phenyl or a heterocyclic $R_4$ member or together with the carbon atom to which they are attached may form a $C_3$-$C_7$ spirocycloalkyl group.

14. Composition according to claim 13 wherein said compound of Formula III is oxazolidine, 3-(dichloroacetyl)-2,2,5-trimethyl-.

15. Composition according to claim 13 wherein said compound of Formula III is 4-(dichloroacetyl)-1-oxa-4-azaspiro-(4,5)decane.

16. Composition according to claim 13 wherein said compound of Formula III is oxazolidine, 3-(dichloroacetyl)-2,2-dimethyl-5-phenyl-.

17. Composition according to claim 10 wherein said compound of Formula II is 4-(dichloroacetyl)-3,4-dihydro-3-methyl-2H-1,4-benzoxazine.

18. Composition according to claim 10 wherein said compound of Formula II is ethanone, 2,2-dichloro-1-(1,2,3,4-tetrahydro-1-methyl-2-isoquinolinyl)-.

19. Composition according to claim 10 wherein said compound of Formula II is cis/trans-piperazine, 1,4-bis(dichloroacetyl)-2,5-dimethyl.

20. Composition according to claim 10 wherein said compound of Formula II is N-(dichloroacetyl)-1,2,3,4-tetrahydroquinaldine.

21. Composition according to claim 10 wherein said compound of Formula II is 1,5-diazacyclononane, 1,5-bis(dichloroacetyl).

22. Composition according to claim 10 wherein said compound of Formula II is 1-azaspiro[4,4]nonane, 1-dichloroacetyl).

23. A composition comprising a herbicidally-effective amount of a compound according to Formula I or agriculturally-acceptable salts thereof and an antidotally-effective amount of at least one of the groups consisting of:

N-N-diallyl-dichloroacetamide,
N-(2-propenyl)-N-(1,3-dioxolanyl methyl) dichloroacetamide,
Oxazolidine, 3-(dichloroacetyl)-2,2,5-trimethyl,
3-(dichloroacetyl)-2,2-dimethyl-5-,
3-(dichloroacetyl)-3,4-dihydro-3-methyl-2H-1,4-benzoxazine,
α-[(cyanomethoxy)imino]benzene acetonitrile,
α-[(1,3-dioxolan-2-yl-methoxy)imino] benzene acetonitrile,
O-[1,3-Dioxolan-2-ylmethyl]-2,2,2-trifluoromethyl-4'-chloroacetophenone oxime or
4-(dichloroacetyl)-1-oxa-4-azaspiro-(4,5)-decane.

24. A composition comprising a herbicidally-effective amount of dicamba or its agriculturally-acceptable salts and an antidotally-effective amount of at least one of the group consisting of:

N-N-diallyl-dichloroacetamide,
N-(2-propenyl)-N-(1,3-dioxolanyl methyl) dichloroacetamide,
Oxazolidine 3-(dichloroacetyl)-2,2,5-trimethyl,
3-(dichloroacetyl)-2,2-dimethyl-5-,
3-(dichloroacetyl)-3,4-dihydro-3-methyl-2H-1,4-benzoxazine,
α-[(cyanomethoxy)imino]benzene acetonitrile,
α-[(1,3-dioxolan-2-yl-methoxy)imino]-benzene acetonitrile,
O-[1,3-Dioxolan-2-ylmethyl]-2,2,2-trifluoromethyl-4'-chloroacetophenone oxime or
4-(dichloroacetyl)-1-oxa-4-azaspiro-(4,5)-decane.

25. Composition comprising:
(a) a herbicidally-effective amount of a compound of Formula I; as defined in the specification
(b) an antidotally-effective amount of a compound of Formula II or Formula III as these formulae are defined in the specification or one of the following compounds:

α-[(Cyanomethoxy)imino]benzeneacetonitrile,
α-[(1,3-Dioxolan-2-yl-methoxy)imino]benzeneacetonitrile,
O-[1,3-Dioxolan-2-ylmethyl]-2,2,2-trifluoromethyl-4'-chloroacetophenone oxime,
Benzenemethamine, N-[4-(dichloromethylene)-1,3-ditholan-2-ylidene]-α-methyl, hydrochloride,
Diphenylmethoxy acetic acid, methyl ester,
1,8-Naphthalic anhydride,
4,6-Dichloro-2-phenyl-pyrimidine,
2-Chloro-N-[1-(2,4,6-trimethylphenyl)ethenyl]acetamide,
Ethylene glycol acetal of 1,1-dichloroacetone, and (c) a herbicidally-effective amount of one or more additional herbicidal compounds as co-herbicide(s) with said compounds of Formula I; provided that the co-herbicide, when an acetamide, is as defined by Formulae IV or V in the specification.

26. Composition according to claim 25 wherein said co-herbicide is a compound of the formula

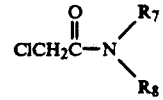

wherein $R_7$ and $R_8$ are independently hydrogen; $C_{1-8}$ alkyl, alkoxy, alkoxyalkyl, acylaminomethyl, acylalkyl-substituted aminomethyl; cycloalkyl, cycloalkylmethyl, alkenyl, alkynyl, cycloalkenyl, cycloalkenylmethyl having up to 8 carbon atoms; phenyl; or $C_{4-10}$ heterocyclyl or heterocyclylmethyl containing from 1 to 4 ring hetero atoms selected independently from N, S or O; and wherein said $R_7$ and $R_8$ members may be substituted with alkyl, alkenyl, alkynyl, alkenyloxy, alkynyloxy, alkoxy, alkoxyalkyl, alkoxycarbomethyl or -ethyl having up to 8 carbon atoms; nitro; halogen; cyano; amino or C$_{1-4}$ alkyl-substituted amino; and wherein R$_7$ and R$_8$ may be combined together with the N atom to which attached to form one of said heterocyclyl or substituted-heterocyclyl members; provided that:
(a) R$_7$ and R$_8$ are not simultaneously hydrogen;
(b) when R$_7$ is substituted-phenyl, the positions on the phenyl ring ortho to the N atom are other than alkoxy or trifluoromethyl and when the ortho positions contain an alkyl radical, R$_8$ is other than alkyl or acylaminomethyl;
(c) when R$_7$ is cycloalkenyl or substituted cycloalkenyl or phenyl, R$_8$ is other than an (un)substituted (2-oxo-3(2H)benzothiazolyl)methyl radical;
(d) when R$_7$ is an alkenyl or substituted alkenyl radical, R$_8$ is other than a substituted-alkylene radical.

27. Composition according to claim 26 wherein R$_7$ is an alkoxyalkyl radical or a substituted or unsubstituted heterocyclyl or heterocyclylmethyl radical and R$_8$ is a substituted or unsubstituted heterocyclyl or heterocyclylmethyl radical or an alkyl-substituted phenyl radical.

28. Composition according to claim 27 wherein said compound of Formula IV is acetochlor, alachlor, butachlor, metolachlor, pretilachlor or metazachlor.

29. Composition according to claim 31 wherein said compound of Formula IV is N-(2,4-dimethylthien-3-yl)-N-(1-methoxyprop-2-yl)-2-chloroacetamide, N-(1H-(pyrazol-1-ylmethyl)-N-(2,4-dimethylthien-3-yl)-2-chloroacetamide or N-(1-pyrazol-1-ylmethyl)N-(4,6-dimethoxypyrimidin-5-yl)-2-chloroacetamide.

30. Composition according to claim 29 wherein said compound of Formula IV is N-(2,4-diamethylthien-3-yl)-N-(1-methoxyprop-2-yl) chloroacetamide 31. Composition according to claim 27 wherein in said compound of Formula IV R$_7$ is a substituted or unsubstituted pyrazolyl or pyrazolylmethyl radical.

32. Composition according to claim 31 wherein said compound of Formula IV is N-(1H-pyrazol-1-ylmethyl)-N-(2,4-dimethylthien-3-yl)-2-chloroacetamide, or N-(1-pyrazol-1-ylmethyl)-N-(4,6-dimethoxypyrimidin-5-yl)-2-chloroacetamide.

33. Composition according to claim 25 wherein said co-herbicide is an α-chloroacetanilide according to Formula V

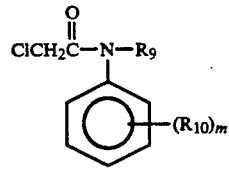

wherein
R$_9$ is hydrogen, C$_{1-6}$ alkyl, haloalkyl, alkoxy or alkoxyalkyl, alkenyl, haloalkenyl, alkynyl or haloalkynyl having up to 6 carbon atoms, C$_{5-10}$ heterocyclyl or heterocyclylmethyl having O, S and/or N atoms and which may be substituted with halogen, C$_{1-4}$ alkyl, carbonylalkyl or carbonylalkoxyalkyl, nitro, amino or cyano groups;
R$_{10}$ is hydrogen, halogen, nitro, amino, C$_{1-6}$ alkyl, alkoxy or alkoxyalkyl, and
m is 0-5. provided that when m is O, R$_9$ is not an (un)substituted (2-oxo-3(2H)benzothiazolyl)methyl radical; when m is other than O, R$_{10}$ is not an alkoxy or trifluoromethyl radical in an ortho position and when R$_{10}$ is an alkyl in the ortho positions R$_9$ is not an alkyl or acylaminomethyl radical.

34. Composition according to claim 33 wherein said α-chloroacetanilide is acetochlor, alachlor, butachlor, metolachlor, pretilachlor or metazachlor.

35. Composition according to any of claims 25 37 or 38 wherein the compound of Formula I is dicamba or its agriculturally-acceptable salts.

36. Composition according to claim 35 wherein the compound of Formula II is N,N-diallyldichloroacetamide, N-(2-propenyl)-N-(1,3-dioxolan-2-yl-methyl)dichloroacetamide or a 1,3-oxazolidinyl dichloroacetamide compound according to the formula

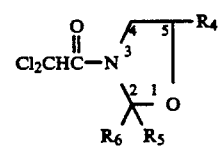

wherein
R$_4$ is hydogen, C$_{1-4}$ alkyl, alkylol, haloalkyl or alkoxy, C$_{2-6}$ alkoxyalkyl, a bicyclic hydrocarbon radical having up to 10 carbon atoms, phenyl or a saturated or unsaturated heterocyclic radical having C$_{5-10}$ ring atoms and containing from 1 to 4 ring hetero atoms selected independently from O, S and/or N atoms, or said phenyl and heterocyclic radical substituted with one or more C$_{1-4}$ alkyl, haloalkyl, alkoxy, alkoxyalkyl, halogen or nitro radicals, and R$_5$ and R$_6$ are independently hydrogen, C$_{1-4}$ alkyl or haloalkyl, phenyl or a heterocyclic R$_4$ member or together with the carbon atom to which they are attached may form a C$_3$-C$_7$ spirocycloalkyl group.

37. Composition according to claim 36 wherein said compound of Formula III is oxazolidine, 3-(dichloroacetyl)-2,2,5-trimethyl-.

38. Composition according to claim 36 wherein said compound of Formula III is 4-(dichloroacetyl)-1-oxa-azaspiro-(4,5)-decane.

39. Composition according to claim 36 wherein said compound of Formula III is oxazolidine, 3-dichloroacetyl)-2,2-dimethyl-5-phenyl-.

40. Composition according to claim 36 wherein said compound of Formula III is oxazolidine, 3-(dichloroacetyl)-2,2-dimethyl-5-(2-furanyl)-.

41. Composition according to claim 36 wherein said compound of Formula III is oxazolidine, 3-(dichloroacetyl)-2,2-dimethyl-5-(2-thienyl)-.

42. Composition according to claim 36 wherein said compound of Formula III is pyridine, 3-[3-(dichloroacetyl)-2,2-dimethyl-5-oxazolidinyl]-.

43. Composition according to claim 35 comprising as the compound of Formula II an antidotally-effective amount of one of the following compounds:
4-(Dichloroacetyl)3,4-dihydro-3-methyl-2H-1,4-benzoxazine,
Ethanone, 2,2-dichloro-1-(1,2,3,4-tetrahydro-1-methyl-2-isoquinolinyl)-,
Cis/trans-piperazine, 1,4-bis(dichloroacetyl)-2,5-dimethyl-,
N-(Dichloroacetyl)-1,2,3,4-tetrahydroquinaldine,
1,5-Diazacyclononane, 1,5-bis(dichloroacetyl,
1-Azaspiro[4,4]nonane, 1-(dichloroacetyl).

44. Composition according to claim 43 wherein said compound of Formula II is 4-(dichloroacetyl)-3,4-dihydro-3-methyl-2H-1,4-benzoxazine.

45. Composition according to claim 43 wherein said compound of Formula II is ethanone, 2,2-dichloro-(1,2,3,4-tetrahydro-1-methyl-2-isoquinol)-.

46. Composition according to claim 43 wherein said compound of Formula II is cis/trans-piperazine, 1,4-bis(dichloroacetyl)-2,5-dimethyl-.

47. Composition according to claim 43 wherein said compound of Formula II is N-(dichloroacetyl)-1,2,3,4-tetrahydroquinaldine.

48. Composition according to claim 43 wherein said compound of Formula II is 1,5-diazacyclononane, 1,5-bis(dichloroacetyl).

49. Composition according to claim 43 wherein said compound of Formula II is 1-azaspiro[4,4]nonane, 1-(dichloroacetyl).

50. Composition according to claim 35 comprising an antidotally-effective amount of one of the following compounds:
α-[(Cyanomethoxy)imino]benzeneaceto-nitrile,
α-[(1,3-Dioxolan-2-yl-methoxy)imino]benzeneacetonitrile,
O-[1,3-Dioxolan-2-ylmethyl]-2,2,2-tri fluoromethyl-4′-chloroacetophenone oxime,
Benzenemethamine, N-[4-(dichloromethylene]-1,3-dithiolan-2-ylidene]-α-methyl, hydrochloride,
Diphenylmethoxy acetic acid, methyl ester,
1,8-Naphthalic anhydride,
4,6-Dichloro-2-phenyl-pyrimidine,
2-Chloro-N-[1-(2,4,6-trimethylphenyl)ethenyl]acetamide,
Ethylene glycol acetal of 1,1-dichloroacetone.

51. Composition comprising a herbicidally-effective amount of benzoic acid substituted with only chlorine atoms or $C_{1-5}$ alkoxy radicals or agriculturally-acceptable salts thereof and a co-herbicidal compound according to Formulae IV or V and an antidotally-effective amount of at least one of the following:
N,N-diallyl-dichloroacetamide,
N-(2-propenyl)-N-(1,3-dioxolanylmethyl)dichloroacetamide,
Oxazolidine 3-(dichloroacetyl)-2,2,5-trimethyl,
Oxazolidine 3-(dichloroacetyl)-2,2-dimethyl-5-(-2-furanyl)-,
3-(dichloroacetyl)3,4-dihydro-3-methyl-2H-1,4-benzoxazine,
α-[(cyanomethoxy)imino]benzene acetonitrile,
α-[(1,3-dioxolan-2-yl-methoxy)imino]benzene acetonitrile,
O-[1,3-Dioxolan-2-ylmethyl]-2,2,2-trifluoromethyl-4′-chloroacetophenone oxime, or
4-(dichloroacetyl)-1-oxa-4-azaspiro-(4,5-decane.

52. Composition according to claim 51 wherein said compound of Formula IV is selected from the group consisting of acetochlor, alachlor, butachlor, metazachlor, metolachlor, pretilachlor, N-(2,4-dimethylthien-3-yl)-N-(1-methoxyprop-2-yl)-2-chloroacetamide, N-(1H-pyrazol-1-ylmethyl)-N-(2,4-dimethylthien-3-yl)-2-chloroacetamide, and N-(1-pyrazol-1-ylmethyl)-N-(4,6-dimethoxypyrimidin-5-yl)-2-chloroacetamide.

53. Composition according to claim 51 wherein said co-herbicide is an α-chloroacetanilide according to Formula V

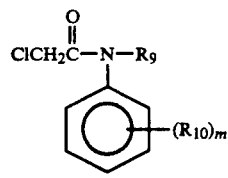

wherein
$R_9$ is hydrogen, $C_{1-6}$ alkyl, haloalkyl, alkoxy or alkoxyalkyl, alkenyl, haloalkenyl, alkynyl or haloalkynyl having up to 6 carbon atoms, $C_{5-10}$ heterocyclyl or heterocyclylmethyl having O, S and/or N atoms and which may be substituted with halogen, $C_{1-4}$ alkyl, carbonylalkyl or carbonylalkoxyalkyl, nitro, amino or cyano groups;
$R_{10}$ is hydrogen, halogen, nitro, amino, $C_{1-6}$ alkyl, alkoxy or alkoxyalkyl, and
m is 0–5; provided that when m is O, $R_9$ is not an (un)substituted (2-oxo-3(2H)benzothiazolyl)methyl radical; when m is other than O, $R_{10}$ is not an alkoxy or trifluoromethyl radical in an ortho position and when $R_{10}$ is an alkyl in the ortho positions $R_9$ is not an alkyl or acylaminomethyl radical.

54. Composition according to claim 53 wherein said α-chloroacetanilide is acetochlor, alachlor, butachlor, metolachlor, pretilachlor or metazachlor.

55. Composition consisting essentially of dicamba or agriculturally-acceptable salts thereof and 4-(dichloroacetyl)-1-oxa-4-azaspiro (4,5)-decane.

56. Composition comprising acetochlor, dicamba or agriculturally-acceptable salts thereof, and 4-(dichloroacetyl)-1-oxa-azaspiro (4,5) decane.

57. Composition comprising acetochlor, dicamba or agriculturally-acceptable salts thereof, and 3-(dichloroacetyl)-2,2-dimethyl-5-(2-furanyl)-oxazolidine.

58. Composition comprising alachlor, dicamba or agriculturally-acceptable salts thereof, and 4-(dichloroacetyl)-1-oxa-4-azaspiro (4,5)-decane.

59. Composition comprising alachlor, dicamba or agriculturally-acceptable salts thereof, and 3-(dichloroacetyl)-2,2-dimethyl-5-(2-furanyl)oxazolidine.

60. Method for reducing phytotoxicity to crop plants due to herbicidal compounds having the formula

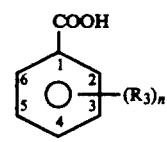

and agriculturally-acceptable salts thereof wherein
$R_3$ is halogen, $C_{1-5}$ alkoxy or $C_{1-4}$ alkyl-substituted amino and
n is 0–5
in admixture with one or more additional herbicidal compounds as co-herbicide(s) with said compound of Formula I provided that the co-herbicide, when an acetamide, is as defined by Formulae IV or V which comprises applying to the locus of the crop plant an antidotally-effective amount of
(i) a compound of the formula

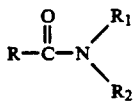

wherein R can be selected from the group consisting of haloalkyl; haloalkenyl; alkyl; alkenyl; cycloalkyl; cycloalkylalkyl; halogen; hydrogen; carboalkoxy; N-alkenylcarbamylalkyl; N-alkenylcarbamyl; N-alkyl-N-alkynylcarbamyl; N-alkyl-N-alkynylcarbamylalkyl; N-alkenylcarbamylalkoxyalkyl; N-alkyl-N-alkynylcarbamylalkoxyalkyl; alkynoxy; haloalkoxy; thiocyanatoalkyl; alkenylaminoalkyl; alkylcarboalkyl; cyanoalkyl; cyanatoalkyl; alkenylaminosulfonoalkyl; alkylthioalkyl; haloalkylcarbonyloxyalkyl; alkoxycarboalkyl; haloalkenylcarbonyloxyalkyl; hydroxyhaloalkyloxyalkyl; hydroxyalkylcarboalkyoxyalkyl; hydroxyalkyl; alkoxysulfonoalkyl; furyl, thienyl; alkyldithiolenyl; thienalkyl; phenyl and substituted phenyl wherein said substituents can be selected from halogen, alkyl, haloalkyl, alkoxy, carbamyl, nitro, carboxylic acids and their salts, haloalkylcarbamyl; phenylalkyl; phenylhaloalkyl; phenylalkenyl; substituted phenylalkenyl wherein said substituents can be selected from halogen, alkyl, alkoxy, halophenoxy, phenylalkoxy; phenylalkylcarboxyalkyl; phenylcycloalkyl; halophenylalkenoxy; halothiophenylalkyl; halophenoxyalkyl; bicycloalkyl; alkenylcarbamylpyridinyl; alkynylcarbamylpyridinyl; dialkenylcarbamylbicycloalkenyl; alkynylcarbamylbicycloalkenyl;

R₁ and R₂ can be the same or different and can be selected from the group consisting of alkenyl; haloalkenyl; hydrogen; alkyl; haloalkyl; alkynyl; cyanoalkyl; hydroxyalkyl; hydroxyhaloalkyl; haloalkylcarboxyalkyl; alkylcarboxyalkyl; alkoxycarboxyalkyl; thioalkylcarboxyalkyl; alkoxycarboalkyl; alkylcarbamyloxyalkyl; amino; formyl; haloalkyl-N-alkylamido; haloalkylamido; haloalkylamidoalkyl; haloalkyl-N-alkylamidoalkyl; haloalkylamidoalkenyl; alkylimino; cycloalkyl; alkylcycloalkyl; alkoxyalkyl; alkylsulfonyloxyalkyl; mercaptoalkyl; alkylaminoalkyl; alkoxycarboalkenyl; haloalkylcarbonyl; alkylcarbonyl; alkenylcarbamyloxyalkyl; cycloalkylcarbamyloxyalkyl; alkoxycarbonyl; haloalkoxycarbonyl; halophenylcarbamyloxyalkyl; bonyl; haloalkoxycarbonyl; halophenylcarbamyloxyalkyl; cycloalkenyl; phenyl; substituted phenyl wherein said substituents can be selected from alkyl, halogen, haloalkyl, alkoxy, haloalkylamido, phthalamido, hydroxy, alkylcarbamyloxy, alkenylcarbamyloxy, alkylamido, haloalkylamido or alkylcarboalkenyl; phenylsulfonyl; substituted phenylalkyl wherein said substituents can be selected from halogen or alkyl; dioxyalkylene, halophenoxyalkylamidoalkyl; alkylthiodiazolyl; piperidyl; piperidylalkyl; dioxolanylalkyl, thiazolyl; alkylthiazolyl; benzothiazolyl; halobenzothiazolyl; furyl; alkyl-substituted furyl; furylalkyl; pyridyl; alkylpyridyl; alkyloxazolyl; tetrahydrofurylalkyl; 3-cyano, thienyl; alkyl-substituted thienyl; 4,5-polyalkylenethienyl; α-haloalkylacetamidophenylalkyl; α-haloalkylacetamidonitrophenylalkyl; α-haloalkylacetamidohalophenylalkyl; cyanoalkenyl;

R₁ and R₂ when taken together can form a structure consisting of piperidinyl; alkylpiperidinyl; pyridyl; di- or tetrahydropyridinyl; alkyltetrahydropyridyl; morpholyl; alkylmorpholyl; azabicyclononyl; diazacycloalkanyl; benzoalkylpyrrolidinyl; oxazolidinyl; perhydrooxazolidinyl; alkyloxazolidyl; furyloxazolidinyl; thienyloxazolidinyl; pyridyloxazolidinyl; pyrimidinyloxazolidinyl; benzooxazolidinyl; C₃₋₇ spirocycloalkyloxazolidinyl; alkylaminoalkenyl; alkylideneimino; pyrrolidinyl; piperidonyl; perhydroazepinyl; perhydroazocinyl; pyrazolyl; dihydropyrazolyl; piperazinyl; perhydro-1,4-diazepinyl; quinolinyl; isoquinolinyl; dihydro-, tetra- hydro- and perhydroquinolyl- or -isoquinolyl; indolyl and di- and perhydroindolyl and said combined R₁ and R₂ members substituted with those independent R₁ and R₂ radicals enumerated above; or (ii) one of the following compounds α-[(Cyanomethoxy)imino]benzeneacetonitrile, α-[(1,3-Dioxolan-2-yl-methoxy)imino]-benzeneacetonitrile, O-[1,3-Dioxolan-2-ylmethyl]-2,2,2-trifluoromethyl-4'-chloroacetophenone oxime, Benzenemethamine, N-[4-(dichloromethylene]-1,3-dithiolan-2-ylidene]-α-methyl, hydrochloride, Diphenylmethoxy acetic acid, methyl ester, 1,8-Naphthalic anhydride, 4,6-Dichloro-2-phenyl-pyrimidine, 2-Chloro-N-[l-(2,4,6-trimethylphenyl)ethenyl]acetamide, Ethylene glycol acetal of 1,1-dichloroacetone.

61. Method according to claim 60 wherein said co-herbicide is a compound of the formula

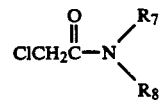

wherein R₇ and R₈ are independently hydrogen; C₁₋₈ alkyl, alkoxy, alkoxyalkyl, acylaminomethyl, acyl-lower alkyl-substituted aminomethyl; cycloalkyl, cycloalkylmethyl, mono- or polyunsaturated alkenyl, alkynyl, cycloalkenyl, cycloalkenylmethyl having up to 8 carbon atoms; phenyl; or C₄₋₁₀ heterocyclyl or heterocyclylmethyl containing from 1 to 4 ring hetero atoms selected independently from N, S or O; and wherein said R₇ and R₈ members may be substituted with alkyl, alkenyl, alkynyl, alkenyloxy, alkynyloxy, alkoxy, alkoxyalkyl, alkoxycarbomethyl or ethyl having up to 8 carbon atoms; nitro; halogen; cyano; amino or C₁₋₄ alkyl-substituted amino; and wherein R₇ and R₈ may be combined together with the N atom to which attached to form one of said heterocyclyl or substituted-heterocyclyl members; provided that:

(a) R₇ and R₈ are not simultaneously hydrogen;

(b) when R₇ is substituted-phenyl, the positions on the phenyl ring ortho to the N atom are other than alkoxy or trifluoromethyl and when the ortho positions contain an alkyl radical, R₈ is other than alkyl or acylaminomethyl;

(c) when R₇ is cycloalkenyl or substituted cycloalkenyl or phenyl, R₈ is other than an (un)substituted (2-oxo-3(2H)benzothiazolyl) methyl radical;

(d) when R₇ is an alkenyl or substituted alkenyl radical, R₈ is other than a substituted-alkylene radical.

62. Method according to claim 61 wherein said compound of Formula I is dicamba or its agriculturally-acceptable salts.

63. Method according to claim 62 wherein in said compound of Formula IV, $R_7$ is an alkoxyalkyl or a (un)substituted heterocyclyl or heterocyclylmethyl radical and $R_8$ is a (un)substituted heterocyclyl or heterocyclylmethyl radical or an alkyl-substituted phenyl radical.

64. Method according to claim 63 wherein said compound of Formula IV is acetochlor, alachlor, butachlor, metazachlor, metolachlor, pretilachlor, N-(2,4-dimethylthien-3-yl)-N-(1-methoxyprop-2-yl)-2-chloroacetamide, N-(1H-pyrazol-1-ylmethyl)-N-(2,4-dimethylthien-3-yl)-2-chloroacetamide or N-(1-pyrazol-1-ylmethyl)-N-(4,6-dimethoxypyrimidin-5-yl)-2-chloroacetamide.

65. Method according to claim 64 wherein said antidotal compound is one of the following compounds:
α-[(Cyanomethoxy)imino]benzeneacetonitrile,
α-[(1,3-Dioxolan-2-yl-methoxy)imino]-benzeneacetonitrile,
O-[1,3-Dioxolan-2-ylmethyl]-2,2,2-trifluoromethyl-4'-chloroacetophenone oxime,
Benzenemethamine, N-[4-(dichloromethylene]-1,3-dithiolan-2-ylidene]-α-methyl, hydrochloride,
Diphenylmethoxy acetic acid, methyl ester,
1,8-Naphthalic anhydride,
4,6-Dichloro-2-phenyl-pyrimidine,
2-Chloro-N-[1-(2,4,6-trimethylphenyl)-ethenyl]acetamide,
Ethylene glycol acetal of 1,1-dichloroacetone.

66. Method according to claim 64 wherein said antidotal compound is one of the following compounds:
4-(Dichloroacetyl)-3,4-dihydro-3-methyl-2H-1,4-benzoxazine,
Ethanone, 2,2-dichloro-1-(1,2,3,4-tetrahydro-1-methyl-2-isoquinolinyl)-,
Cis/trans-piperazine, 1,4-bis(dichloroacetyl)-2,5-dimethyl-,
N-(Dichloroacetyl)-1,2,3,4-tetrahydroquinaldine,
1,5-Diazacyclononane, 1,5-bis(dichloroacetyl,
1-Azaspiro[4,4]nonane, 1-dichloroacetyl).

67. Method according to claim 60 wherein said co-herbicide is an α-chloroacetanilide according to Formula V

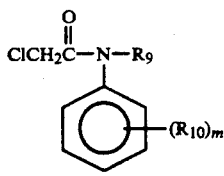

wherein
$R_9$ is hydrogen, $C_{1-6}$ alkyl, haloalkyl, alkoxy or alkoxyalkyl, alkenyl, haloalkenyl, alkynyl or haloalkynyl having up to 6 carbon atoms, $C_{5-10}$ heterocyclyl or heterocyclylmethyl having O, S and/or N atoms and which may be substituted with halogen, $C_{1-4}$ alkyl, carbonylalkyl or carbonylalkoxyalkyl, nitro, amino or cyano groups;
$R_{10}$ is hydrogen, halogen, nitro, amino, $C_{1-6}$ alkyl, alkoxy or alkoxyalkyl, and
m is 0–5; provided that when m is O, $R_9$ is not an (un)substituted (2-oxo-3(2H)benzothiazolyl)methyl radical; when m is other than O, $R_{10}$ is not an alkoxy or trifluoromethyl radical in an ortho position and when $R_{10}$ is an alkyl in the ortho positions $R_9$ is not an alkyl or acylaminomethyl radical.

68. Method according to claim 67 wherein said α-chloroacetanilide is acetochlor, alachlor, butachlor, metolachlor, pretilachlor or metazachlor.

69. Method according to any of claims 60, 64, 67 or 68 wherein said antidotal compound is N,N-diallyldichloroacetamide, N-(2-propenyl)-N-(1,3-dioxolan-2-ylmethyl)dichloroacetamide or 1,3-oxazolidine dichloroacetamide of the formula

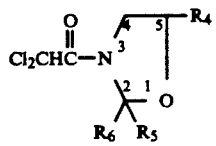

wherein
$R_4$ is hydrogen, $C_{1-4}$ alkyl, alkylol, haloalkyl or alkoxy, $C_{2-6}$ alkoxyalkyl, a bicyclic hydrocarbon radical having up to 10 carbon atoms, phenyl or a saturated or unsaturated heterocyclic radical having $C_{4-10}$ ring atoms and containing from 1 to 4 ring hetero atoms selected independently from O, S or N atoms, or said phenyl and heterocyclic radical substituted with one or more $C_{1-4}$ alkyl, haloalkyl, alkoxy, alkoxyalkyl, halogen or nitro radicals, and
$R_5$ and $R_6$ are independently hydrogen, $C_{1-4}$ alkyl or haloalkyl, phenyl or a heterocyclic $R_4$ member or together with the carbon atom to which they are attached may form a $C_3$–$C_7$ spirocycloalkyl group.

70. Method according to claim 69 wherein said antidotal compound is one of the following compounds:
Oxazolidine, 3-(dichloroacetyl)-2,2,5-trimethyl-,
4-(dichloroacetyl)-1-oxa-4-azaspiro-(4,5)-decane,
Oxazolidine, 3-(dichloroacetyl)-2,2-dimethyl-5-phenyl-,
Oxazolidine, 3-(dichloroacetyl)-2,2-dimethyl-5-(2-furanyl)-,
Oxazolidine, 3-(dichloroacetyl)-2,2-dimethyl-5-(2-thienyl)- or
Pyridine, 3-[3-(dichloroacetyl)-2,2-dimethyl-5-oxazolidinyl]-.

71. A method for reducing phytotoxicity to crop plants due to a compound according to Formula I or agriculturally-acceptable salts thereof which comprises applying to the locus of the crop plant an antidotally-effective amount of at least one of the following:
N,N-diallyl-dichloroacetamide,
N-(2-propenyl)-N-(1,3-dioxolanylmethyl)dichloroacetamide,
Oxazolidine 3-(dichloroacetyl)-2,2,5-trimethyl,
3-(dichloroacetyl)-2,2-dimethyl-5,
3-(dichloroacetyl)3,4-dihydro-3-methyl-2H-1,4-benzoxazine,
α-[(cyanomethoxy)imino]benzene acetonitrile,
α-[(1,3-dioxolan-2-yl-methoxy)imino]benzene acetonitrile,
O-[1,3-Dioxolan-2-ylmethyl]-2,2,2-trifluoromethyl-4'-chloroacetophenone oxime, or
4-(dichloroacetyl)-1-oxa-4-azaspiro-(4,5-decane.

72. Method according to claim 71 wherein in the compound of Formula I the $R_3$ members are chlorine atoms or $C_{1-5}$ alkoxy radicals.

73. A method for reducing phytotoxicity to crop plants due to dicamba or agriculturally-acceptable salts thereof which comprises applying to the locus of the crop plant an antidotally-effective amount of at least one of the following:

N,N-diallyl-dichloroacetamide,
N-(2-propenyl)-N-(1,3-dioxolanylmethyl)dichloroacetamide,
Oxazolidine 3-(dichloroacetyl)-2,2,5-trimethyl,
3-dichloroacetyl)-2,2-dimethyl-5,
3-(dichloroacetyl)3,4-dihydro-3-methyl-2H-1,4-benzoxazine,
α-[(cyanomethoxy)imino]benzene acetonitrile,
α-[(1,3-dioxolan-2-yl-methoxy)imino]benzene acetonitrile,
O-[1,3-Dioxolan-2-ylmethyl]-2,2,2-trifluoromethyl-4'-chloroacetophenone oxime, or
4-(dichloroacetyl)-1-oxa-4-azaspiro-(4,5-decane.

74. Method for reducing phytotoxicity to crop plants which comprises applying to the soil a herbicidal composition consisting essentially of a compound according to Formula I or agriculturally-acceptable salts thereof and an antidote selected from the following:
N,N-diallyl-dichloroacetamide,
N-(2-propenyl)-N-(1,3-dioxolanylmethyl)-dichloroacetamide,
Oxazolidine 3-(dichloroacetyl)-2,2,5-trimethyl,
3-(dichloroacetyl)-2,2-dimethyl-5-,
3-(dichloroacetyl)3,4-dihydro-3-methyl-2H-1,4-benzoxazine,
α-[(cyanomethoxy)imino]benzene acetonitrile,
α-[(1,3-dioxolan-2-yl-methoxy)imino]benzene acetonitrile,
5 0-[I,3-Dioxolan-2-ylmethyl]-2,2,2-trifluoromethyl-4'-chloroacetophenone oxime, or
4-(dichloroacetyl)-1-oxa-4-azaspiro-(4,5-decane.

75. Method according to claim 74 wherein in the compound of Formula I the $R_3$ members are chlorine atoms or $C_{1-5}$ alkoxy radicals.

76. Method for reducing phytotoxicity to crop plants which comprises applying to the soil a herbicidal composition comprising dicamba or its agriculturally-acceptable salts, an acetamide selected from the group consisting of acetochlor, alachlor, butachlor, metazachlor, metolachlor, pretilachlor, N-(2,4-dimethylthien-3-yl)-N-(1-methoxyprop-2-yl)-2-chloroacetamide, N-(1H-pyrazol-1-ylmethyl)-N-(2,4-dimethylthien-3-yl)-2-chloroacetamide, and N-(1-pyrazol-1-ylmethyl)-N-(4,6-dimethoxypyrimidin-5-yl)-2-chloroacetamide and an antidote for said herbicidal composition selected from the group consisting of:
N,N-diallyl-dichloroacetamide,
N-(2-propenyl)-N-(1,3-dioxolanylmethyl)dichloroacetamide,
Oxazolidine 3-(dichloroacetyl)-2,2,5-trimethyl,
Oxazolidine 3-(dichloroacetyl)-2,2-dimethyl-5-(-2-furanyl)-,
3-(dichloroacetyl)3,4-dihydro-3-methyl-2H-1,4-benzoxazine,
α-[(cyanomethoxy)imino]benzene acetonitrile,
α-[(1,3-dioxolan-2-yl-methoxy)imino]benzene acetonitrile, or
O-[1,3-Dioxolan-2-ylmethyl]-2,2,2-trifluoromethyl-4'-chloroacetophenone oxime or
4-(dichloroacetyl)-1-oxa-4-azaspiro-(4,5-decane.

77. Method according to any of claims 60–75 or wherein said crop plant is corn.

78. Method according to claim 69 wherein said crop is corn.

79. Method according to claim 70 wherein said crop is corn.

80. Method according to claim 78 wherein said antidotal compound is N,N-diallyl dichloroacetamide.

81. Method according to claim 79 wherein said compound of Formula III is 4-(dichloroacetyl)-1-oxa-4-azaspiro (4,5)-decane.

82. Method according to claim 79 wherein said compound of Formula III is oxazolidine, 3-(dichloroacetyl)-2,2-dimethyl-5-(2-furanyl).

83. Method according to claim 79 wherein said compound of Formula III is oxazolidine, 3-(dichloroacetyl)-2,2,5-trimethyl.

* * * * *